(12) United States Patent
Ashby

(10) Patent No.: US 7,985,164 B2
(45) Date of Patent: Jul. 26, 2011

(54) METHODS AND SYSTEMS FOR CONTROLLING AN EXERCISE APPARATUS USING A PORTABLE DATA STORAGE DEVICE

(75) Inventor: Darren C. Ashby, Richmond, UT (US)

(73) Assignee: ICON IP, Inc.

( * ) Notice: Subject to any disclaimer, the term of this patent is extended or adjusted under 35 U.S.C. 154(b) by 1022 days.

(21) Appl. No.: 11/315,682

(22) Filed: Dec. 21, 2005

(65) Prior Publication Data

US 2007/0265138 A1   Nov. 15, 2007

Related U.S. Application Data

(63) Continuation-in-part of application No. 10/856,676, filed on May 28, 2004, now Pat. No. 7,628,730, which is a continuation-in-part of application No. 09/776,410, filed on Feb. 2, 2001, now Pat. No. 6,997,852, which is a continuation-in-part of application No. 09/641,220, filed on Aug. 18, 2000, now Pat. No. 6,458,060, which is a continuation-in-part of application No. 09/349,608, filed on Jul. 8, 1999, now Pat. No. 6,312,363, and a continuation-in-part of application No. 09/496,560, filed on Feb. 2, 2000, now Pat. No. 6,447,424, said application No. 09/776,410 is a continuation-in-part of application No. 09/641,627, filed on Aug. 18, 2000, now Pat. No. 7,166,062, which is a continuation-in-part of application No. 09/349,608, filed on Jul. 8, 1999, now Pat. No. 6,312,363, and a continuation-in-part of application No. 09/496,560, filed on Feb. 2, 2000, now Pat. No. 6,447,424, said application No. 09/776,410 is a continuation-in-part of application No. 09/641,600, filed on Aug. 18, 2000, now Pat. No. 7,060,006, which is a continuation-in-part of application No. 09/349,608, filed on Jul. 8, 1999, now Pat. No. 6,312,363, and a continuation-in-part of application No. 09/496,560, filed on Feb. 2, 2000, now Pat. No. 6,447,424.

(51) Int. Cl.
*A63B 71/00* (2006.01)
(52) U.S. Cl. ............... 482/8; 482/1; 482/9; 482/901; 434/247
(58) Field of Classification Search ........... 482/1–9, 482/900–902; 434/247
See application file for complete search history.

(56) References Cited

U.S. PATENT DOCUMENTS 3,518,985 A   7/1970   Quinton
(Continued)

FOREIGN PATENT DOCUMENTS

CN   1162495 A   10/1997
(Continued)

OTHER PUBLICATIONS

Notice of Allowance and Fees Due dated Dec. 30, 2008, 8 pages, U.S. Appl. No. 10/856,676.

(Continued)

*Primary Examiner* — Glenn Richman
(74) *Attorney, Agent, or Firm* — ICON Health & Fitness, Inc.

(57) ABSTRACT

Systems, devices, methods and computer program products for providing an exercise device access to information stored on a portable memory device. An exercise device includes a data port which is adapted to receive the portable memory device, regardless of its format. For instance, either a Secure Digital or multimedia format memory card may be accessed through the same data port. To access the portable memory device, the exercise device stores the access protocols for each of the various formats. Upon determining that the format of the memory device, the exercise device then selectively applies the appropriate protocols, which may allow read and optionally write access to the portable memory device. The enabled communication allows the exercise device to access data stored on the memory card. The accessed data may include personal user information, exercise programs, and motivational content. The data can be delivered to the user.

33 Claims, 14 Drawing Sheets

U.S. PATENT DOCUMENTS

| | | |
|---|---|---|
| 3,602,502 A | 8/1971 | Hampl |
| 3,802,698 A | 4/1974 | Burian et al. |
| 3,845,756 A | 11/1974 | Olsson |
| 3,903,613 A | 9/1975 | Bisberg |
| 4,020,795 A | 5/1977 | Marks |
| 4,112,928 A | 9/1978 | Putsch |
| 4,151,988 A | 5/1979 | Nabinger |
| 4,220,996 A | 9/1980 | Searcy |
| 4,278,095 A | 7/1981 | Lapeyre |
| 4,358,105 A | 11/1982 | Sweeney, Jr. |
| 4,408,613 A | 10/1983 | Relyea |
| 4,504,055 A | 3/1985 | Wells |
| 4,542,897 A | 9/1985 | Melton et al. |
| 4,544,152 A | 10/1985 | Taitel |
| 4,549,044 A | 10/1985 | Durham |
| 4,556,216 A | 12/1985 | Pitkanen |
| 4,571,682 A | 2/1986 | Silverman et al. |
| 4,642,769 A | 2/1987 | Petrofsky |
| 4,659,074 A | 4/1987 | Taitel et al. |
| 4,687,195 A | 8/1987 | Potts |
| 4,702,475 A | 10/1987 | Elstein et al. |
| 4,708,337 A | 11/1987 | Shyu |
| 4,708,837 A | 11/1987 | Baxter et al. |
| 4,709,917 A | 12/1987 | Yang |
| 4,757,495 A | 7/1988 | Decker et al. |
| 4,763,284 A | 8/1988 | Carlin |
| 4,765,613 A | 8/1988 | Voris |
| 4,786,049 A | 11/1988 | Lautenschlager |
| 4,818,234 A | 4/1989 | Redington et al. |
| 4,828,257 A | 5/1989 | Dyer et al. |
| 4,837,157 A | 6/1989 | Turnell et al. |
| 4,842,266 A | 6/1989 | Sweeney, Sr. et al. |
| 4,842,274 A | 6/1989 | Oosthuizen et al. |
| 4,848,737 A | 7/1989 | Ehrenfield |
| 4,860,763 A | 8/1989 | Schminke |
| 4,866,704 A | 9/1989 | Bergman |
| 4,889,108 A | 12/1989 | Bond et al. |
| 4,919,418 A | 4/1990 | Miller |
| 4,925,183 A | 5/1990 | Kim |
| 4,925,189 A | 5/1990 | Braeunig |
| 4,927,136 A | 5/1990 | Leask |
| 4,934,694 A | 6/1990 | McIntosh |
| 4,938,474 A | 7/1990 | Sweeney et al. |
| 4,949,993 A | 8/1990 | Stark et al. |
| 4,959,713 A | 9/1990 | Morotomi et al. |
| 4,998,725 A | 3/1991 | Watterson et al. |
| 5,020,795 A | 6/1991 | Airy et al. |
| 5,054,774 A | 10/1991 | Belsito |
| 5,062,632 A | 11/1991 | Dalebout et al. |
| 5,067,710 A | 11/1991 | Watterson et al. |
| 5,078,152 A | 1/1992 | Bond et al. |
| 5,086,385 A | 2/1992 | Launey et al. |
| 5,089,960 A | 2/1992 | Sweeney, Jr. |
| 5,104,120 A | 4/1992 | Watterson et al. |
| 5,113,427 A | 5/1992 | Ryoichi et al. |
| 5,137,501 A | 8/1992 | Mertesdorf |
| 5,145,475 A | 9/1992 | Cares |
| 5,149,084 A | 9/1992 | Dalebout et al. |
| 5,180,347 A | 1/1993 | Chen |
| 5,195,935 A | 3/1993 | Fencel |
| 5,201,772 A | 4/1993 | Maxwell |
| 5,213,555 A | 5/1993 | Hood et al. |
| 5,230,673 A | 7/1993 | Maeyama et al. |
| 5,240,417 A | 8/1993 | Smithson et al. |
| 5,243,998 A | 9/1993 | Silverman et al. |
| 5,254,066 A | 10/1993 | Brown et al. |
| 5,256,115 A | 10/1993 | Scholder et al. |
| 5,277,678 A | 1/1994 | Friedebach et al. |
| 5,290,205 A | 3/1994 | Densmore et al. |
| 5,292,293 A | 3/1994 | Schumacher |
| 5,299,810 A | 4/1994 | Pierce et al. |
| 5,308,296 A | 5/1994 | Eckstein |
| 5,308,300 A | 5/1994 | Chino et al. |
| 5,313,942 A | 5/1994 | Platzker |
| 5,314,391 A | 5/1994 | Potash et al. |
| 5,318,487 A | 6/1994 | Golen et al. |
| 5,318,491 A | 6/1994 | Houston |
| D348,493 S | 7/1994 | Ashby |
| 5,328,420 A | 7/1994 | Allen |
| 5,328,422 A | 7/1994 | Nichols |
| 5,335,188 A | 8/1994 | Brisson |
| 5,352,166 A | 10/1994 | Chang |
| 5,361,091 A | 11/1994 | Hoarty et al. |
| 5,375,068 A | 12/1994 | Palmer et al. |
| 5,382,209 A | 1/1995 | Pasier et al. |
| 5,385,519 A | 1/1995 | Hsu et al. |
| 5,385,520 A | 1/1995 | Lepine et al. |
| 5,387,164 A | 2/1995 | Brown, Jr. |
| 5,403,252 A | 4/1995 | Leon et al. |
| 5,407,402 A | 4/1995 | Brown et al. |
| 5,410,471 A | 4/1995 | Alyfuku et al. |
| 5,410,472 A | 4/1995 | Anderson |
| 5,433,679 A | 7/1995 | Szymczak et al. |
| 5,435,799 A | 7/1995 | Lundin |
| 5,451,922 A | 9/1995 | Hamilton |
| 5,462,051 A | 10/1995 | Oka et al. |
| 5,462,503 A | 10/1995 | Benjamin et al. |
| 5,462,504 A | 10/1995 | Trulaske et al. |
| 5,466,200 A | 11/1995 | Ulrich et al. |
| 5,474,090 A | 12/1995 | Begun et al. |
| 5,484,389 A | 1/1996 | Stark et al. |
| 5,489,249 A | 2/1996 | Brewer et al. |
| 5,512,025 A | 4/1996 | Dalebout et al. |
| 5,527,239 A | 6/1996 | Abbondanza |
| 5,535,664 A | 7/1996 | Rokowski |
| 5,538,486 A | 7/1996 | France et al. |
| 5,546,324 A | 8/1996 | Palmer et al. |
| 5,547,439 A | 8/1996 | Rawls et al. |
| 5,572,643 A | 11/1996 | Judson |
| 5,577,981 A | 11/1996 | Jarvik |
| 5,584,779 A | 12/1996 | Knecht et al. |
| 5,590,128 A | 12/1996 | Maloney et al. |
| 5,591,104 A | 1/1997 | Andrus et al. |
| 5,598,849 A | 2/1997 | Browne |
| 5,600,310 A | 2/1997 | Whipple, III et al. |
| 5,605,336 A | 2/1997 | Gaoiran et al. |
| 5,619,412 A | 4/1997 | Hapka |
| 5,619,991 A | 4/1997 | Sloane |
| 5,626,539 A | 5/1997 | Piaget et al. |
| 5,645,509 A | 7/1997 | Brewer et al. |
| 5,645,513 A | 7/1997 | Haydocy et al. |
| 5,655,997 A | 8/1997 | Greenberg et al. |
| 5,663,951 A | 9/1997 | Danneels et al. |
| 5,667,459 A | 9/1997 | Su |
| 5,690,582 A | 11/1997 | Ulrich et al. |
| 5,690,852 A | 11/1997 | Saito et al. |
| 5,695,400 A | 12/1997 | Fennell, Jr. et al. |
| 5,697,834 A | 12/1997 | Heumann et al. |
| 5,702,323 A | 12/1997 | Poulton |
| 5,704,875 A * | 1/1998 | Tanabe ............... 482/4 |
| 5,713,794 A | 2/1998 | Shimojima et al. |
| 5,720,771 A | 2/1998 | Snell |
| 5,722,418 A | 3/1998 | Bro |
| 5,738,612 A | 4/1998 | Tsuda |
| 5,743,833 A | 4/1998 | Watterson et al. |
| 5,749,372 A | 5/1998 | Allen et al. |
| 5,752,883 A | 5/1998 | Butcher et al. |
| 5,752,897 A | 5/1998 | Skowronski et al. |
| 5,754,765 A | 5/1998 | Danneels et al. |
| 5,759,199 A | 6/1998 | Snell et al. |
| 5,771,354 A | 6/1998 | Crawford |
| 5,777,678 A | 7/1998 | Ogata et al. |
| 5,779,596 A | 7/1998 | Weber |
| 5,785,630 A | 7/1998 | Bobick et al. |
| 5,785,631 A | 7/1998 | Heidecke |
| 5,810,696 A | 9/1998 | Webb |
| 5,813,864 A | 9/1998 | Ikuta |
| 5,836,770 A | 11/1998 | Powers |
| 5,838,906 A | 11/1998 | Doyle et al. |
| 5,845,230 A | 12/1998 | Lamberson |
| 5,854,833 A | 12/1998 | Hogan et al. |
| 5,857,939 A | 1/1999 | Kaufman |
| 5,865,733 A | 2/1999 | Malinouskas et al. |
| 5,873,369 A | 2/1999 | Lanaido et al. |
| 5,880,677 A | 3/1999 | Lestician |
| 5,888,172 A | 3/1999 | Andrus et al. |
| 5,890,906 A | 4/1999 | Macri et al. |

| | | | | | | |
|---|---|---|---|---|---|---|
| 5,890,995 | A | 4/1999 | Bobick et al. | 6,648,802 B2 | 11/2003 | Ware |
| 5,905,442 | A | 5/1999 | Mosebrook et al. | 6,659,916 B1 | 12/2003 | Shea |
| 5,909,544 | A | 6/1999 | Anderson, II et al. | 6,659,946 B1 | 12/2003 | Batchelor et al. |
| 5,910,070 | A | 6/1999 | Henry et al. | 6,669,600 B2 | 12/2003 | Warner |
| 5,911,132 | A | 6/1999 | Sloane | 6,687,535 B2 | 2/2004 | Hautala et al. |
| 5,911,687 | A | 6/1999 | Sato et al. | 6,689,057 B1 | 2/2004 | Shinsel et al. |
| 5,916,063 | A | 6/1999 | Alessandri | 6,700,788 B2 | 3/2004 | Matsushita et al. |
| 5,917,405 | A | 6/1999 | Joao | 6,702,719 B1 | 3/2004 | Brown et al. |
| 5,929,748 | A | 7/1999 | Odinak | 6,712,737 B1 | 3/2004 | Nusbaum |
| 5,929,782 | A | 7/1999 | Stark | 6,736,759 B1 | 5/2004 | Stubbs et al. |
| 5,931,763 | A | 8/1999 | Alessandri | 6,740,007 B2 | 5/2004 | Gordon et al. |
| 5,947,869 | A | 9/1999 | Shea | 6,749,537 B1 | 6/2004 | Hickman |
| 5,956,509 | A | 9/1999 | Kevner | 6,783,482 B2 | 8/2004 | Oglesby et al. |
| 5,961,561 | A | 10/1999 | Wakefield, II | 6,786,848 B2 | 9/2004 | Yamashita et al. |
| 5,964,701 | A | 10/1999 | Asada et al. | 6,790,178 B1 | 9/2004 | Mault et al. |
| 5,967,975 | A | 10/1999 | Ridgeway | 6,793,607 B2 | 9/2004 | Neil |
| 5,993,356 | A | 11/1999 | Houston et al. | 6,808,472 B1 | 10/2004 | Hickman |
| 5,995,868 | A | 11/1999 | Dorfmeister et al. | 6,808,473 B2 | 10/2004 | Hisano et al. |
| 5,997,476 | A | 12/1999 | Brown | 6,824,502 B1 | 11/2004 | Huang |
| 6,004,243 | A | 12/1999 | Ewert | 6,825,876 B1 | 11/2004 | Easwar et al. |
| 6,010,451 | A | 1/2000 | Clawson | 6,863,641 B1 | 3/2005 | Brown et al. |
| 6,013,007 | A | 1/2000 | Root et al. | 6,866,613 B1 | 3/2005 | Brown et al. |
| 6,014,432 | A | 1/2000 | Modney | 6,918,858 B2 | 7/2005 | Watterson et al. |
| 6,022,272 | A | 2/2000 | Sano | 6,921,351 B1 | 7/2005 | Hickman et al. |
| 6,033,344 | A | 3/2000 | Trulaske et al. | 6,976,624 B2 | 12/2005 | Hsiao |
| 6,042,519 | A | 3/2000 | Shea | 6,991,586 B2 | 1/2006 | Lapcevic |
| 6,050,822 | A | 4/2000 | Faughn | 6,997,852 B2 | 2/2006 | Watterson et al. |
| 6,050,924 | A | 4/2000 | Shea | 7,022,047 B2 | 4/2006 | Cohen et al. |
| 6,050,942 | A | 4/2000 | Rust et al. | 7,044,891 B1 | 5/2006 | Rivera |
| 6,053,737 | A | 4/2000 | Babbit et al. | 7,056,265 B1 | 6/2006 | Shea |
| 6,053,844 | A | 4/2000 | Clem | 7,060,006 B1 | 6/2006 | Watterson et al. |
| 6,059,692 | A | 5/2000 | Hickman | 7,060,008 B2 | 6/2006 | Watterson et al. |
| 6,066,075 | A | 5/2000 | Poulton | 7,070,539 B2 | 7/2006 | Brown et al. |
| 6,066,705 | A | 5/2000 | Calderon et al. | 7,072,789 B2 | 7/2006 | Vock et al. |
| 6,106,297 | A | 8/2000 | Pollak et al. | 7,115,076 B2 | 10/2006 | Oglesby et al. |
| 6,110,076 | A | 8/2000 | Hurt | 7,128,693 B2 | 10/2006 | Brown et al. |
| 6,132,337 | A | 10/2000 | Krupka et al. | 7,166,062 B1 | 1/2007 | Watterson et al. |
| 6,142,913 | A | 11/2000 | Ewert | 7,166,064 B2 | 1/2007 | Watterson et al. |
| 6,148,262 | A | 11/2000 | Fry | 7,254,516 B2 | 8/2007 | Case, Jr. et al. |
| 6,152,854 | A | 11/2000 | Carmein | 7,350,787 B2 | 4/2008 | Voss |
| 6,152,856 | A | 11/2000 | Studor et al. | 7,354,380 B2 | 4/2008 | Volpe, Jr. |
| 6,162,151 | A | 12/2000 | Tani et al. | 7,455,622 B2 | 11/2008 | Watterson et al. |
| 6,162,189 | A | 12/2000 | Girone et al. | 7,510,509 B2 | 3/2009 | Hickman |
| 6,171,186 | B1 | 1/2001 | Kurosawa et al. | 7,537,546 B2 | 5/2009 | Watterson et al. |
| 6,171,218 | B1 | 1/2001 | Shea | 7,549,947 B2 | 6/2009 | Hickman et al. |
| 6,193,631 | B1 | 2/2001 | Hickman | 7,556,590 B2 | 7/2009 | Watterson et al. |
| 6,211,451 | B1 | 4/2001 | Tohgi et al. | 7,575,536 B1 | 8/2009 | Hickman |
| 6,231,481 | B1 | 5/2001 | Brock | 7,625,315 B2 | 12/2009 | Hickman |
| 6,231,482 | B1 | 5/2001 | Thompson | 7,628,730 B1 | 12/2009 | Watterson et al. |
| 6,241,524 | B1 | 6/2001 | Aoshima et al. | 7,637,847 B1 | 12/2009 | Hickman |
| 6,244,987 | B1 | 6/2001 | Ohsuga et al. | 7,645,212 B2 | 1/2010 | Ashby et al. |
| 6,244,988 | B1 | 6/2001 | Delman | 7,645,213 B2 | 1/2010 | Watterson et al. |
| 6,251,048 | B1 | 6/2001 | Kaufman | 7,713,171 B1 | 5/2010 | Hickman |
| 6,283,896 | B1 | 9/2001 | Grunfeld et al. | 2002/0042328 A1 | 4/2002 | Yoo |
| 6,312,363 | B1 | 11/2001 | Watterson et al. | 2002/0055422 A1 | 5/2002 | Airmet et al. |
| 6,322,451 | B1 | 11/2001 | Miura | 2004/0012335 A1 | 1/2004 | Shon et al. |
| 6,356,856 | B1 | 3/2002 | Damen et al. | 2004/0127335 A1 | 7/2004 | Watterson et al. |
| 6,358,187 | B1 | 3/2002 | Smith | 2004/0162189 A1 | 8/2004 | Hickman |
| 6,371,850 | B1 | 4/2002 | Sonoda | 2005/0233859 A1 | 10/2005 | Takai et al. |
| 6,402,558 | B1 | 6/2002 | Hung-Ju et al. | 2005/0233861 A1 | 10/2005 | Hickman et al. |
| 6,450,922 | B1 | 9/2002 | Henderson et al. | 2005/0261609 A1 | 11/2005 | Collings et al. |
| 6,458,060 | B1 | 10/2002 | Watterson et al. | 2005/0272564 A1 | 12/2005 | Pyles et al. .............. 482/54 |
| 6,463,385 | B1 | 10/2002 | Fry | 2006/0063645 A1 | 3/2006 | Chiang |
| 6,464,618 | B1 | 10/2002 | Shea | 2006/0205566 A1 | 9/2006 | Watterson et al. |
| 6,475,115 | B1 | 11/2002 | Candito et al. | 2006/0205569 A1 | 9/2006 | Watterson et al. |
| 6,497,638 | B1 | 12/2002 | Shea | 2006/0281603 A1 | 12/2006 | Hickman |
| 6,503,173 | B2 | 1/2003 | Clem | 2008/0051256 A1 | 2/2008 | Ashby et al. |
| 6,582,342 | B2 | 6/2003 | Kaufman | 2008/0300110 A1 | 12/2008 | Smith et al. |
| 6,585,622 | B1 | 7/2003 | Shum et al. | 2009/0258758 A1 | 10/2009 | Hickman et al. |
| 6,601,016 | B1 | 7/2003 | Brown et al. | 2009/0270226 A1 | 10/2009 | Watterson et al. |
| 6,605,020 | B1 | 8/2003 | Huang | 2009/0270227 A1 | 10/2009 | Ashby |
| 6,605,038 | B1 | 8/2003 | Teller et al. | | | |
| 6,612,492 | B1 | 9/2003 | Yen | | FOREIGN PATENT DOCUMENTS | |
| 6,616,578 | B2 | 9/2003 | Alessandri | CN | 2449755 Y | 9/2001 |
| 6,626,799 | B2 | 9/2003 | Watterson et al. | DE | 41 00 559 A1 | 7/1991 |
| 6,634,992 | B1 | 10/2003 | Ogawa | EP | 0 199 442 | 10/1986 |
| 6,638,198 | B1 | 10/2003 | Shea | JP | H10-243979 | 9/1998 |
| 6,645,124 | B1 | 11/2003 | Clem | WO | WO8101507 | 6/1991 |
| 6,648,798 | B2 | 11/2003 | Yoo | WO | WO9417860 | 8/1994 |

| | | |
|---|---|---|
| WO | WO 96/38205 | 12/1996 |
| WO | WO 98/00204 | 1/1998 |
| WO | WO 98/32496 | 7/1998 |
| WO | WO 2007/081607 | 7/2007 |

OTHER PUBLICATIONS

Notice of Allowance and Fees Due dated Dec. 17, 2008, 5 pages, U.S. Appl. No. 11/440,703.
Final Office Action dated Jan. 6, 2009, 8 pages, U.S. Appl. No. 11/657,701.
Final Office Action dated Dec. 13, 2008, 7 pages, U.S. Appl. No. 11/150,914.
Notice of Allowance and Fees Due dated Jan. 28, 2009, 15 pages, U.S. Appl. No. 10/674,911.
DVD labeled "iFIT.com Media Coverage News Clips Ver. 3.0," dated Mar. 30, 2000.
Office Action dated Sep. 11, 2000, 3 pages, U.S. Appl. No. 09/349,608.
Notice of Allowance and Issue Fee Due, date mailed Jul. 25, 2001, 2 pages, U.S. Appl. No. 09/349,608.
Notice of Allowance and Fee(s) Due, date mailed Sep. 20, 2004, 7 pages, U.S. Appl. No. 09/641,627.
Restriction Requirement dated Apr. 29, 2005, 4 pages, U.S. Appl. No. 09/641,627.
Office Action dated Jul. 26, 2005, 4 pages, U.S. Appl. No. 09/641,627.
Notice of Allowance and Fee(s) Due, date mailed Feb. 3, 2006, 4 pages, U.S. Appl. No. 09/641,627.
Notice of Allowance and Fee(s) Due, date mailed Sep. 1, 2006, 4 pages, U.S. Appl. No. 09/641,627.
Restriction Requirement dated Apr. 17, 2007, 5 pages, U.S. Appl. No. 11/429,858.
Office Action dated Aug. 22, 2007, 5 pages, U.S. Appl. No. 11/429,858.
Restriction Requirement dated Feb. 5, 2008, 8 pages, U.S. Appl. No. 11/429,858.
Restriction Requirement dated Sep. 23, 2003, 4 pages, U.S. Appl. No. 09/641,600.
Office Action dated Feb. 11, 2004, 4 pages, U.S. Appl. No. 09/641,600.
Notice of Allowance and Fee(s) Due, date mailed Jun. 2, 2004, 4 pages, U.S. Appl. No. 09/641,600.
Office Action dated Feb. 15, 2005, 7 pages, U.S. Appl. No. 09/641,600.
Notice of Allowance and Fee(s) Due, date mailed Sep. 14, 2005, 4 pages, U.S. Appl. No. 09/641,600.
Office Action dated Dec. 18, 2001, 3 pages, U.S. Appl. No. 09/641,220.
Notice of Allowance and Fee(s) Due, date mailed Jul. 1, 2002, 5 pages, U.S. Appl. No. 09/641,220.
Office Action dated Jun. 29, 2004, 3 pages, U.S. Appl. No. 09/776,410.
Notice of Allowance and Fee(s) Due, date mailed Nov. 12, 2004, 4 pages, U.S. Appl. No. 09/776,410.
Notice of Allowance and Fee(s) Due, date mailed Apr. 18, 2005, 5 pages, U.S. Appl. No. 09/776,410.
Restriction Requirement dated Oct. 9, 2007, 5 pages, U.S. Appl. No. 10/856,676.
Office Action dated Jan. 24, 2008, 5 pages, U.S. Appl. No. 10/856,676.
Restriction Requirement dated Jul. 1, 2003, 4 pages, U.S. Appl. No. 09/947,193.
Office Action dated Oct. 23, 2003, 4 pages, U.S. Appl. No. 09/947,193.
Notice of Allowance and Fee(s) Due, date mailed May 14, 2004, 4 pages, U.S. Appl. No. 09/947,193.
Office Action dated Sep. 15, 2005, 5 pages, U.S. Appl. No. 09/947,193.
Notice of Allowance and Fee(s) Due, date mailed Jan. 26, 2006, 5 pages, U.S. Appl. No. 09/947,193.
Notice of Allowance and Fee(s) Due, date mailed Aug. 16, 2006, 4 pages, U.S. Appl. No. 09/947,193.
Restriction Requirement dated Mar. 26, 2007, 5 pages, U.S. Appl. No. 11/429,725.
Office Action dated Jun. 6, 2007, 5 pages, U.S. Appl. No. 11/429,725.
Restriction Requirement dated Nov. 14, 2007, 5 pages, U.S. Appl. No. 11/429,725.
Final Office Action dated Feb. 28, 2008, 8 pages, U.S. Appl. No. 11/429,725.
Restriction Requirement dated Sep. 21, 2004, 4 pages, U.S. Appl. No. 10/106,842.
Office Action dated Nov. 12, 2004, 4 pages, U.S. Appl. No. 10/106,842.
Notice of Allowance and Fee(s) Due, date mailed Mar. 14, 2005, 6 pages, U.S. Appl. No. 10/106,842.
Notice of Allowance and Fee(s) Due, date mailed Mar. 29, 2006, 6 pages, U.S. Appl. No. 11/132,740.
Notice of Allowance and Fee(s) Due, date mailed Jun. 30, 2003, 5 pages, U.S. Appl. No. 09/933,701.
Restriction Requirement dated Aug. 22, 2006, 5 pages, U.S. Appl. No. 10/674,911.
Office Action dated Dec. 12, 2006, 7 pages, U.S. Appl. No. 10/674,911.
Restriction Requirement dated Jul. 2, 2007, 5 pages, U.S. Appl. No. 10/674,911.
Final Office Action dated Nov. 28, 2007, 8 pages, U.S. Appl. No. 10/674,911.
Office Action dated Apr. 22, 2008, 10 pages, U.S. Appl. No. 10/674,911.
Office Action dated Jun. 16, 1997, 4 pages, U.S. Appl. No. 08/766,513.
Office Action dated Feb. 17, 1998, 5 pages, U.S. Appl. No. 08/766,513.
Notice of Allowance and Issue Fee Due, date mailed Sep. 22, 1998, 3 pages, U.S. Appl. No. 08/766,513.
Response to Rule 312 Communication, dated Jun. 2, 1999, 2 pages, U.S. Appl. No. 08/766,513.
Office Action dated Dec. 10, 1999, 3 pages, U.S. Appl. No. 09/273,591.
Notice of Allowance and Fee(s) Due, date mailed Jul. 14, 2000, 2 pages, U.S. Appl. No. 09/273,591.
Office Action dated Dec. 18, 2001, 3 pages, U.S. Appl. No. 09/690,701.
Office Action dated Sep. 25, 2002, 4 pages, U.S. Appl. No. 09/690,701.
Final Office Action dated Mar. 21, 2003, 4 pages, U.S. Appl. No. 09/690,701.
Advisory Action dated Jun. 16, 2003, 2 pages, U.S. Appl. No. 09/690,701.
Notice of Allowance and Fee(s) Due, date mailed Nov. 24, 2003, 5 pages, U.S. Appl. No. 09/690,701.
Restriction Requirement dated Dec. 29, 2004, 4 pages, U.S. Appl. No. 10/729,356.
Office Action dated Feb. 16, 2005, 5 pages, U.S. Appl. No. 10/729,356.
Restriction Requirement dated Feb. 21, 2006, 5 pages, U.S. Appl. No. 10/729,356.
Notice of Allowance and Fee(s) Due, date mailed Jun. 13, 2006, 6 pages, U.S. Appl. No. 10/729,356.
Response to Rule 312 Communication, dated Jul. 30, 2007, 2 pages, U.S. Appl. No. 10/729,356.
Office Action dated Jan. 14, 2008, 7 pages, U.S. Appl. No. 10/729,356.
Office Action dated Jan. 24, 2005, 4 pages, U.S. Appl. No. 10/773,617.
Notice of Allowance and Fee(s) Due, date mailed Apr. 17, 2006, 4 pages, U.S. Appl. No. 10/773,617.
Notice of Allowance and Fee(s) Due, date mailed Jul. 6, 2006, 4 pages, U.S. Appl. No. 10/773,617.
Office Action dated May 16, 2007, 4 pages, U.S. Appl. No. 10/773,617.
Office Action dated Jan. 24, 2008, 8 pages, U.S. Appl. No. 10/773,617.
Final Office Action dated Apr. 24, 2008, 10 pages, U.S. Appl. No. 10/773,617.

Office Action dated Dec. 18, 2001, 3 pages, U.S. Appl. No. 09/690,178.
Notice of Allowance and Fee(s) Due, date mailed Sep. 23, 2002, 5 pages, U.S. Appl. No. 09/690,178.
Office Action dated Mar. 7, 2003, 4 pages, U.S. Appl. No. 09/690,178.
Notice of Allowance and Fee(s) Due, date mailed Nov. 24, 2003, 4 pages, U.S. Appl. No. 09/690,178.
Response to Rule 312 Communication, dated Jan. 21, 2004, 2 pages, U.S. Appl. No. 09/690,178.
Office Action dated Jan. 27, 2005, 6 pages, U.S. Appl. No. 10/751,334.
Final Office Action dated Aug. 25, 2005, 6 pages, U.S. Appl. No. 10/751,334.
Notice of Allowance and Fee(s) Due, date mailed Jun. 12, 2006, 4 pages, U.S. Appl. No. 10/751,334.
Restriction Requirement dated Apr. 17, 2007, 5 pages, U.S. Appl. No. 10/751,334.
Restriction Requirement dated Aug. 9, 2007, 5 pages, U.S. Appl. No. 10/751,334.
Office Action dated Jan. 25, 2008, 7 pages, U.S. Appl. No. 10/751,334.
Office Action dated Jun. 15, 2004, 4 pages, U.S. Appl. No. 10/045,619.
Notice of Allowance and Fee(s) Due, date mailed Mar. 14, 2005, 4 pages, U.S. Appl. No. 10/045,619.
Restriction Requirement dated Jul. 27, 2006, 5 pages, U.S. Appl. No. 11/150,914.
Restriction Requirement dated Oct. 18, 2006, 5 pages, U.S. Appl. No. 11/150,914.
Office Action dated Feb. 22, 2007, 6 pages, U.S. Appl. No. 11/150,914.
Final Office Action dated Dec. 12, 2007, 8 pages, U.S. Appl. No. 11/150,914.
Advisory Action dated Feb. 7, 2008, 3 pages, U.S. Appl. No. 11/150,914.
Final Office Action dated May 6, 2008 for U.S. Appl. No. 10/856,676, filed May 28, 2004.
Non-final Office Action dated May 1, 2008 for U.S. Appl. No. 11/849,068, filed Aug. 31, 2007.
Restriction Requirement dated Apr. 28, 2008 for U.S. Appl. No. 11/150,914, filed Jun. 13, 2005.
Consumer Reports, Out of the Rat Race, onto a Treadmill, Feb. 2000 (5 pages).
Consumer Reports, Out of the Rat Race, onto a Treadmill at http://www.accessmylibrary.com/coms2/summaryU0286-28004514_ITM, Mar. 5, 2007, 8 pages.
Notice of Allowance and Fee(s) Due, date mailed Jun. 4, 2008, 8 pages, U.S. Appl. No. 11/429,858.
Notice of Allowance and Fee(s) Due, date mailed Jun. 4, 2008, 9 pages, U.S. Appl. No. 11/429,725.
Final Office Action dated Jun. 2, 2008, 7 pages, U.S. Appl. No. 10/751,334.
Non-final Office Action dated Jun. 13, 2008, 6 pages, U.S. Appl. No. 11/657,701.
Non-final Office Action dated Jun. 26, 2008, 4 pages, U.S. Appl. No. 11/440,703.
Final Office Action dated Jul. 1, 2008, 9 pages, U.S. Appl. No. 10/729,356.
Office Action dated Aug. 18, 2008, 9 pages, U.S. Appl. No. 10/674,911.
Office Action dated Aug. 21, 2008, 6 pages, U.S. Appl. No. 11/849,068.
Notice of Allowance and Fee(s) Due dated Aug. 8, 2008, 4 pages, U.S. Appl. No. 11/429,858.
Notice of Allowance and Fee(s) Due dated Sep. 8, 2008, 4 pages, U.S. Appl. No. 11/429,725.
Office Action Summary dated Nov. 25, 2008, 6 pages, U.S. Appl. No. 10/751,334.
Office Action Summary dated Oct. 16, 2008, 9 pages, U.S. Appl. No. 10/773,617.
Office Action Summary dated Jun. 27, 2008, 13 pages, U.S. Appl. No. 11/833,070.

Office Action Summary dated Oct. 31, 2008, 23 pages, U.S. Appl. No. 11/833,070.
Office Action dated Dec. 10, 2008, 6 pages, U.S. Appl. No. 11/849,068.
*Little Tony, One on One Video Trainer* (for Model No. T1T123040), Jun. 1995 (25 pages).
*Men's Journal*, Squat.com. The Home Gym Goes Online, May 2000 (2 pages).
MSNBC.com, Smart Fitness Section, *On A Quest for Fitness—The latest workout gear and Gadgets*, Feb. 29, 2000 (6 pages).
OPTIONS Manual: Video Track/Track Five/Personal Trainer Plus (Part No. 109917) cited as "Options"), Sep. 1992 (2 pages).
*PR Newswire*, Turn Your Treadmill Into a Internet Appliance with www.iFIT.com, Oct. 19, 1999 (3 pages).
PRO-FORM 8.0 TXP Manual (for Model No. PF080010) (cited as "8.0TXP"), Nov. 1991 (16 pages).
*The Boston Globe*, Living Section, p. F1, Wired Workout Local Gyms, Mar. 11, 2000 (2 pages).
*The Herald Journal*, People in Business, ICON wins Awards, vol. 91, No. 128, May 7, 2000 (1 page).
*US Weekly*, p. 71, Work Out Online, Mar. 27, 2000 (2 pages).
*Communications of the ACM*, vol. 35, No. 6, cited as "Comm of the ACM", Jun. 1992 (10 pages).
*Ebsco Publishing*, New home exercise equipment: your computer?, Jun. 2000 (3 pages).
*Fortune Magazine*, p. 84, Virtual Workouts—Treadmills Possessed, Apr. 17, 2000 (1 page).
*Good House Keeping*, p. 53, A Run for the Money, Feb. 2000 (2 pages).
*IEEE Publication*, A Telerobotics Construction Set with Integrated Performance Analysis, 0-8186-7108-4/95 (IEEE) (cited as "Telerobotic Con."), Apr. 1995 (7 pages).
*IEEE Publication*, Intelligent Monitoring System for Limited System for Limited Communication Path: Telerobotic Task Execution over Internet, 0-8186-7108-4/95 (IEEE) (cited as "Intelligent"), Apr. 1995 (6 pages).
*Lifestyler* 10.0 ESP Manual (for Model No. 297052) (cited as "10.0 ESP"), Nov. 1992 (16 pages).
*1994 Pro-Form First in Fitness*, (1994 Copyright ProForm Products, Inc.), (16 pages).
The FitLinxx Interactive Fitness Network™, *Integrated Fitness Corp.*, brochure, 1998.
Fitlinxx Interactive Fitness Network™, The Difference Between Surviving and Thriving May be as Simple as Fitlinxx™, *Integrated Fitness Corp.*, brochure, 1998.
Netpulse, *Networkingout—Coming Distractions: Netpulse Helps Exercisers Surf the Net at the Gym, Accomplish Several Goals at Once*, www.netpulse.com, Apr. 1998.
Netpulse, *Instead of having an equipment repair technician traveling over hill and dale, you may soon have equipment repaired via the internet*, www.netpulse.com, Jul. 1998.
Netpulse, Exercise station connects to the Net, *Now you can sweat to the Net.*, www.netpulse.com, Sep. 1998.
Netpulse, New Fitness Equipment Combines Internet, Sweat, *Now you can surf and sweat*, www.netpulse.com, Jan. 1999.
Netpulse, Hop in, Log on and Sweat, *Netpulse exercise machines are the latest Web feat*, www.netpulse.com, Feb. 1999.
Netpulse ClubWatch™, *Internet Powered Service*, brochure, Apr. 1999.
Netpulse, *State of the Art*, www.netpulse.com, Feb. 2000.
Netpulse, *Netpulse Files for Patents on its Pioneering Technology Inventions and Groundbreaking Business Methods in the Media and Fitness Markets*, www.netpulse.com, May 2000.
Forbes, Digital Tool: Startups, *Sweat.equity*, www.forbes.com, Feb. 1998.
*Exergaming*, en.wikipedia.org, printed Oct. 1, 2007 (4 pages).
*WIRED*, www.wired.com, issue 2.09, Sep. 1994 (4 pages).
"Defendant's Amended Invalidity Contentions," Case No. 2:05-cv-527, signed by Kirk Harris on Mar. 16, 2007 (15 pages).
"Icon Health & Fitness, Inc.'s Supplemental Preliminary Invalidity Contentions," Case No. 2:05-cv-527, signed by Brent A. Hansen on Jun. 23, 2006 (24 pages).

"Icon Health & Fitness, Inc.'s Preliminary Invalidity Contentions," Case No. 2:05-cv-527, signed by Brett A. Hansen on Jun. 26, 2006 (378 pages).
"Expert Report of Dr. Brent Nelson Pursuant to Federal Rule of Civil Procedure 26(a)(2)(B)," dated Mar. 13, 2007 (372 pages).
"Netpulse Brings Free Internet Access to Fitness Centers." Newsbytes.com, http://www.newsbytes.com, Jan. 17, 2000 (1 page).
"Precor and Netpulse Partner to Create the World's First Internet Powered Elliptical." Netpulse press release, Oct. 1, 1999 (2 pages).
"Surf While you Sweat." ABCNEWS.com, Oct. 27, 1998 (3 pages).
"The Best Products of 1999—Business Week's Top Picks of the Most Innovative Products on the Market." Business Week, Dec. 6, 1999 (2 pages).
Netpulse brochure. "Catch the wwwave," available on information and belief at least as early as Feb. 10, 2000 (6 pages).
Netpulse, Ultra-Wired—Infotech is supposed to make life easier-remember? Here's how to be sure it does., www.netpulse.com, Aug. 1998.
Winkler, William J., "Pumping Iron With a Digital Friend," Business Week, Dec. 18, 1995, pp. 78a.
Internet Archive Wayback Machine, archive for www.ifit.com, at http://webarchive.org/web/*/www.ifit.com, Sep. 1, 2003, 1 pg.
iFIT.com "Internet Workouts Control Your Treadmill, Bike, or Elliptical," at http://www.ifit.com, Sep. 1, 2003, 3 pages.
Icon Health and Fitness, Nordictrack C2420 (Model No. NTL 14950), 2004.
Icon Health and Fitness, Nordictrack C2420 (Model No. NTL 14951), 2004.
Icon Health and Fitness, Nordictrack C2420 (Model No. NTL 1495.2), 2004.
Icon Health and Fitness, Nordictrack CX 990 (Model No. NEL 09940), 2003.
Icon Health and Fitness, Nordictrack SL 760 (Model No. NTC 89021), 2004.
Icon Health and Fitness, Nordictrack SL 760 (Model No. NTC 89020), 2004.
Icon Health and Fitness, Nordictrack SL 710 (Model No. NTC 07942), 2004.
Icon Health and Fitness, Nordictrack SL 710 (Model No. NTC 07941), 2004.
Icon Health and Fitness, Nordictrack SL 710 (Model No. NTC 07940), 2003.
Icon Health and Fitness, Nordictrack SL 705 (Model No. NTC 05941), 2004.
Icon Health and Fitness, Nordictrack SL 705 (Model No. NTC 05940), 2004.
Icon Health and Fitness, Nordictrack C2420 Manual preceding Specs, 2004.
Icon Health and Fitness, Pro-Form Personal Trainer Plus, undated.
Icon Health and Fitness, Screenshots of iFit.com, undated.
Icon Health and Fitness, iFit.com "Log on. Work out." Brochure, 2000.
Icon Health and Fitness, Website printouts (archived docs), 2000.
Icon Health and Fitness, Pro-Form 600 (Model No. PETL60000), 2000.
Icon Health and Fitness Inc., Reebok ACDI (Model No. RETL11900), 2000.
Icon Health and Fitness Inc., Reebok RT1000 (Model No. RETL16001), 2001.
Icon Health and Fitness Inc., One-on-One Video Trainer (Model No. TLTL21040), 1995.
IEEE Computer Graphics and Applications—EVAC: A Virtual Environment for Control of Remote Imaging Instrumentation, 1996.
IEEE: Performance Analysis of a Gateway Connecting the Cebus to the ISDN, 1993.
Fitness Equipment: Cardio, 1997.
Icon Health and Fitness Inc., Photographs of various fitness equipment systems, 1989-1996.
Mademoiselle, www.IFIT.Com, Mademoiselle, Mar. 2000.
WIRED, ICON Health & Fitness Image 10.4Qi, Wired, Apr. 2000.
COOKING LIGHT, Cybertrainers are Watching Your Workout, Cooking Light, Aug. 2000.
Villarosa, A Fitness Industry, With Gadgets Galore, the New York Times, Apr. 25, 2000.
Little, Web Creates Workouts With Virtual Trainers, The Birmingham News, Apr. 10, 2000.
San Francisco Chronicle, Let the Web Help You Get Physical, Mar. 16, 2000.
DVD Labeled "ICON-CYB001" 881 PDF Files Jun. 12, 2006.
CD-ROM Labeled "Supershow 2000," ICON-CYB 034309 Highlight Video Apr. 20, 2006.
CD-ROM Labeled "Supershow 1998," ICON-CYB 034310 Live Video Streaming from Logan, Utah to Atlanta, Georgia, Feb. 10, 1998.
DVD Lableled "1998 Supershow Web Cast," ICON-CYB 034311 Raw video footage, Jun. 2006.
CD-ROM Labeled "Steve Young Webcast," ICON-CYB 034312, Sales Meeting 2000, Jun. 2006.
Office Action dated Sep. 24, 2009, 11 pages, U.S. Appl. No. 11/657,701.
Supplemental Notice of Allowability dated May 5, 2009, 2 pages, U.S. Appl. No. 11/429,725.
Office Action dated Sep. 29, 2009, 6 pages, U.S. Appl. No. 11/315,682.
Notice of Allowance and Fee(s) Due dated Oct. 30, 2009, 4 pages, U.S. Appl. No. 10/856,676.
Notice of Allowance and Fee(s) Due dated Nov. 2, 2009, 4 pages, U.S. Appl. No. 12/276,900.
"Workouts that Work," Consumer Reports, pp. 31-39, available on information and belief at least as early as Jan. 1999, 9 pages.
New Balance Fitness Equipment advertisement, Runners World, Feb. 2006, 1 page.
New Balance Fitness Equipment advertisement (with sport block dumbbell advertisement), Runners World, Mar. 2006, 1 page.
T Series T3/T5 Treadmill Operation Manual, copyright 2001, Life Fitness, 30 pages.
Advertisement, "We Just Made Buying a Trackmaster 100% Easier," Athletic Business, Oct. 1991, 2 pages.
Advertisement, "Trackmaster TM500E Treadmill Features Interactive Controller," Athletic Business, Oct. 1991, 1 page.
Advertisement, "Survival Equipment for the New Age," Athletic Business, Oct. 1991, p. 60.
Advertisement, "Introducing the LifeStep Model 9500-We've Made the Best Even Better," Athletic Business, Sep. 1991, 1 page.
Advertisement, "We Just Made Buying a Trackmaster 100% Easier," Athletic Business, Sep. 1991, 2 pages.
Trackmaster Online: Treadmill Controllers: http://web.archive.org/web/20010124093300/www.trackmastertreadmills.com/contrlr.html, available on information and belief at least as early as Jan. 2001, 1 page.
Transcript of Deposition of Michael Benjamin, taken Apr. 11, 2007, from *Cybergym Research, LLC* v. *Icon Health & Fitness, et al.,* in the Eastern District of Texas, Marshal Division, Case No. 2:05-cv-527 DF, 33 pages.
Michael Benjamin Computation Book, dated Nov. 2, 1991, 14 pages.
Tectrix Fitness Equipment, VR Bike Owners Manual, Jan. 1995, 19 pages.
Tectrix Fitness Equipment, VR Bike Maintenance and Repair manual, Mar. 1997, 55 pages.
Tectrix Fitness Equipment, Photographs of VR Bike, available on information and belief at least as early as 1994, 13 pages.
Tectrix, Tectrix Fitness Equipment History, Jim Sweeney, Jun. 20, 1996, 4 pages.
Tectrix Fitness Equipment, Are We Having Fun Yet? brochure, 1995, 4 pages.
First for Women, No More Bicycle Boredom, Oct. 3, 1994, 2 pages.
Sports Illustrated, Software for Hardbodies, Sep. 19, 1994, 2 pages.
Cybergear, Inc., CyberGear 1000 brochure, which was available, on information and belief, at least as early as 1994, 2 pages.
National Fitness Trade Journal cover, Fall 1995, 1 page.
Tectrix Fitness Equipment, The Body The Brain The Passion The Will product brochure, circa 1998, 24 pages.
Leisure Management, Going Downhill, Virtually, vol. 14, No. 8, Aug. 1994, 2 pages.

Tectrix Fitness Equipment, Sweeney Town from CyberGear for the Tectrix VRBike brochure, which was available, on information and belief, at least as early as 1994, 2 pages.

"Virtual Treadmill Takes Users Anywhere They Want to Go," http://www.ksl.com?nid=148&sid=6920538, Jun. 24, 2009, 2 pages.

DVD labeled "Tectrix VR Bike videos, including: 1) Media Coverage News Clips of Tectrix VR Bike, dated Jun. 15, 1994, 11 minutes, 19 seconds; 2) Video demonstrating use of CyberGEAR exercise bike, which was available, on information and belief, at least as early as 1994, 5 minutes, 39 seconds; and 3) Video demonstrating use of Tectrix VR Bike, which was available, on information and belief, at least as early as 1994, 4 minutes, 43 seconds".

Notice of Allowance and Fees(s) Due dated Jun. 18, 2009, U.S. Appl. No. 12/276,900.

Notice of Allowance and Fee(s) Due dated Jul. 10, 2009, 4 pages, U.S. Appl. No. 10/859,676.

Notice of Allowance dated Feb. 12, 2009, pages, U.S. Appl. No. 10/856,676.

Notice of Allowance and Fee(s) Due dated Dec. 30, 2008, 8 pages, U.S. Appl. No. 10/856,676.

Notice of Allowance and Fee(s) Due dated Oct. 2, 2008, 8 pages, U.S. Appl. No. 10/856,676.

Office Action dated May 6, 2008, 7 pages, U.S. Appl. No. 10/856,676.

Restriction Requirement dated Oct. 9, 2007, 5 pages, U.S. Appl. No. 10/856,676.

Office Action dated Aug. 14, 2009, 6 pages, U.S. Appl. No. 11/314,133.

Supplemental Notice of Allowance dated Jan. 30, 2009, 2 pages, U.S. Appl. No. 11/429,725.

Notice of Allowance and Fee(s) Due, date mailed Mar. 19, 2009, 7 pages, U.S. Appl. No. 10/729,356.

Notice of Allowance and Fee(s) Due dated May 29, 2009, 4 pages, U.S. Appl. No. 10/773,617.

Office Action dated Apr. 16, 2009, 7 pages, U.S. Appl. No. 11/657,701.

Notice of Allowance and Fee(s) Due dated Jun. 1, 2009, 7 pages, Office Action dated Jun. 1, 2008, 7 pages U.S. Appl. No. 10/751,334.

Notice of Allowance and Fee(s) Due, date mailed Apr. 15, 2009, 5 pages, U.S. Appl. No. 11/150,914.

Office Action dated Aug. 18, 2008, 6 pages, U.S. Appl. No. 11/150,914.

Office Action dated Apr. 16, 2009, 7 pages, U.S. Appl. No. 11/849,068.

Notice of Allowance and Fee(s) Due dated Feb. 19, 2010, 27 pages, U.S. Appl. No. 11/314,133.

Non-Final Office Action dated Feb. 22, 2010, 5 pages, U.S. Appl No. 12/467,776.

Notice of Allowance and Fee(s) Due dated Feb. 12, 2010, 8 pages, U.S. Appl. No. 11/657,701.

Non-Final Office Action dated Apr. 20, 2010, 6 pages, U.S. Appl. No. 12/489,031.

Final Office Action dated Mar. 12, 2010, 7 pages, U.S. Appl. No. 11/849,068.

Notification of the First Office Action issued on Jun. 12, 2009 by the State Intellectual Property Office of the People's Republic of China for Chinese Patent Application No. 200680048743.X, which was nationalized from and claims priority to PCT Publication No. WO 2007/081607, 19 pages including original Chinese version and English translation.

Text of the Response to First Office Action and Amended Claims for the first Office Action, submitted Oct. 26, 2009 to the State Intellectual Property Office of the People's Republic of China for Chinese Patent Application No. 200680048743.X, which was nationalized from and claims priority to PCT Publication No. WO 2007/081607, 17 pages (including original Chinese version and English translation).

Notification of the Second Office Action issued on Dec. 25, 2009 by the State Intellectual Property Office of the People's Republic of China for Chinese Patent Application No. 200680048743.X, which was nationalized from and claims priority to PCT Publication No. WO 2007/081607, 10 pages (including original Chinese version and English translation).

Notice of Allowance and Fees Due, 4 pages, U.S. Appl. No. 11/314,133.

Notice of Allowance and Fees Due, 4 pages, U.S. Appl. No. 12/467,776.

* cited by examiner

METHODS AND SYSTEMS FOR CONTROLLING AN EXERCISE APPARATUS USING A PORTABLE DATA STORAGE DEVICE

RELATED PATENT APPLICATIONS

This application is a continuation-in-part application of U.S. patent application Ser. No. 10/856,676 filed May 28, 2004 now U.S. Pat. No. 7,628,730, entitled "Methods and Systems for Controlling an Exercise Apparatus using a USB Compatible Portable Remote Device," which is hereby incorporated herein by reference in its entirety and which is a continuation-in-part application of U.S. patent application Ser. No. 09/776,410, entitled "Methods and Systems for Controlling an Exercise Apparatus using a Portable Remote Device," filed on Feb. 2, 2001, now U.S. Pat. No. 6,997,852, which is hereby incorporated herein by reference in its entirety. U.S. patent application Ser. No. 09/776,410 is a continuation-in-part application of each of: (a) U.S. patent application Ser. No. 09/641,220, entitled "Systems and Methods for Interaction with Exercise Device," filed on Aug. 18, 2000, now U.S. Pat. No. 6,458,060, which is hereby incorporated herein by reference in its entirety, (b) U.S. patent application Ser. No. 09/641,600, entitled "Computer Systems and Methods for Interaction with Exercise Device," filed Aug. 18, 2000 now U.S. Pat. No. 7,060,006, and (c) U.S. patent application Ser. No. 09/641,627, entitled "System for interaction with Exercise Device," filed Aug. 18, 2000, now U.S. Pat. No. 7,116,062. Each of U.S. patent application Ser. No. 09/641,220, filed Aug. 18, 2000 now U.S. Pat. No. 6,458,060, U.S. patent application Ser. No. 09/641,600, filed Aug. 18, 2000 now U.S. Pat. No. 7,060,006, and U.S. patent application Ser. No. 09/641,627, filed Aug. 18, 2000 now U.S. Pat. No. 7,166,062, is a continuation-in-part application of each of: (1) U.S. patent application Ser. No. 09/496,560, entitled "System and Method for Selective Adjustment of Exercise Apparatus," filed on Feb. 2, 2000, now U.S. Pat. No. 6,447,424, which is hereby incorporated herein by reference in its entirety, and of (2) U.S. patent application Ser. No. 09/349,608, entitled "Systems and Methods for Providing an Improved Exercise Device with Motivational Programming," filed on Jul. 8, 1999, now U.S. Pat. No. 6,312,363, which is hereby incorporated herein by reference in its entirety.

BACKGROUND OF THE INVENTION

1. The Field of the Invention

This invention relates to exercise equipment and, more specifically, to systems and methods for providing improved exercise devices in combination with personalized workout programs and/or personalized user information using a portable storage device.

2. The Relevant Technology

In an attempt to improve their health and physical conditioning, consumers are purchasing home exercise devices in record quantities. One common challenge with home exercise equipment is motivating the purchaser to use the device on a consistent and ongoing basis, while providing access to experienced trainers and individually developed exercise programs from the comfort of a user's own home. In addition, many exercise devices involve repetitive actions, which can quickly become tedious to a person exercising alone.

Health clubs, on the other hand, have organized various exercise classes and routines involving a group setting. In the proper setting, a group approach to exercise creates a synergy, whereby individual members of the class derive encouragement and motivation from other members of the group.

Furthermore, while individuals exercise at a health club they are taught the correct techniques for exercising, thereby reducing the possibility of being injured during an exercise program. In addition, group settings promote a healthy sense of competition among group members. Initially, such group fitness and exercise classes typically involved aerobics, traditionally performed without the use of any ancillary exercise equipment or devices. In recent years, however, the group work out approach has been extended to classes that utilize various exercise devices. Take, for example, the recent rise in popularity of "Spinning Classes," in which each participant operates his or her own stationery exercise cycle in a group setting, with a coach or instructor leading the group through a prescribed program or routine. Similarly, it is possible to have "Treadmill Classes" wherein an instructor leads the group.

One of the primary disadvantages with group training, however, is that it is typically available only at health clubs and, therefore, is not as convenient as exercising in the privacy and comfort of one's own home. It would, therefore, be a definite advancement in the art of home exercise equipment to provide the desirable benefits of group exercise in a home setting. Some efforts have been made in the prior art to introduce a level of "interactivity" into exercise machines. For example, U.S. Pat. No. 5,489,249 discloses a video exercise control system in which a videocassette recorder (VCR) or similar device is coupled, via a hard wired connection, to an exercise machine, such as a treadmill. As an individual exercises on the treadmill, the VCR in synchronization with pre-recorded audio/video presentations controls the speed and incline of the treadmill. U.S. Pat. No. 5,645,509, entitled "Remote Exercise Control System" and which is incorporated herein by reference in its entirety, discloses a remote exercise control system in which an exercise machine, such as a treadmill, may remotely communicate via a communications interface with an evaluation module located at a remote location. Signals indicative of the operating parameters of the treadmill are transmitted from the treadmill to the evaluation module, and control signals are transmitted from the remote evaluation module for controlling the operating parameters of the treadmill. U.S. Pat. No. 5,888,172 is representative of another system, in which an exercise device is coupled, via hard wired connection, to a video game device, such that the operating parameters of the exercise device are used as inputs to the video game controller, which then produces a video display based on the inputs received. However, these approaches nevertheless fail to provide many desirable benefits of group exercise.

BRIEF SUMMARY OF THE INVENTION

The present invention is directed to devices, systems, methods, programs, computer products, computer readable media, and modules for controlling the operating parameters of one or more devices by one or more portable data storage devices. The present invention is particularly well suited to devices that utilize one or more motors and/or other electrically driven actuators that control one or more operating parameters of a device, such as an exercise device.

In one embodiment, an implementation of the present invention takes place in association with an exercise device and a portable memory card. One example of such an exercise device is a treadmill, although a variety of different exercise devices may be employed, such as exercise cycles, Nordic style ski exercise devices, rowers, steppers, hikers, climbers, elliptical or striding exercise devices, incline trainers, weight systems, and any other motorized or other device that utilizes motors, solenoids, or any other electrically driven actuators to control one or more operating parameters of the device.

According to one aspect of the invention, an exercise device has a movable element for movement in the performance of exercise by a user, and a console which is operatively connected to the movable element and has a data port configured to receive at least two types of portable memory cards. Examples of types of portable memory cards include Secure Digital, multimedia, and DataFlash cards. To facilitate access of the multiple types of cards, the exercise device may also include means for accessing user data stored on the portable memory card. Examples of user data may include information personal to a user or information accessible by a user. For instance, user data may include a user's name, age, gender, weight, fitness level, exercise preferences, exercise device type, exercise history, and other similar information. Other information accessible by a user, and thus also user data, may include, for example, exercise programs which may also include control signals, control signal instructions, an exercise profile, or motivational content. Motivational content may be audio, including music, or video.

When a portable memory card is received by the data port, the means for accessing user data may determine the type of portable memory card received. Accordingly, access protocols may be selectively applied as appropriate for the type of card received. Such access protocols may enable read and/or write access. For instance, the write access protocols may allow the exercise device to write user data, including a user's personal information and workout histories to the memory card. Such write access may be enabled although access to one or more of the types of cards accessible through the data port is restricted when the card is accessed by a general purpose computing system.

According to another exemplary embodiment of the present invention, the treadmill can include an exercise mechanism which comprises the movable element, while having one or more operating parameters that control the movable element. Further, a data port may be operatively connected to the exercise mechanism and adapted to receive and communicate with a portable memory card having any of a plurality of formats, so as to access an exercise program stored on a portable memory card in any such format. To facilitate access, a communication module may be operatively connected to the exercise mechanism and data port, and be capable of accessing the exercise program on the memory card. Further, the exercise device may include a processor which communicates with the communication module. The processor can deliver control signals to the exercise mechanism to cause a change in one or more operating parameters of the exercise mechanism, thereby also modifying the movable element.

The exercise device may further include a control panel which enables a user to quickly and easily use the exercise device. Optionally, a data port is integrated into the control panel of the exercise device. Where the exercise device is a treadmill, it may alternatively be located in a tread base. Similarly, the communication module may be integral with the processor, either wholly or partially, such that the processor has the capabilities associated with the communication module. In some embodiments, the exercise system includes a program generation module in communication with the processor and adapted to create an exercise program. The processor may, for example, receive user input and pass the user input to the program generation module which then creates an exercise program in response to the user input.

In another embodiment, the exercise system is configured to deliver preprogrammed exercise programs to a user with an exercise device that has one or more moveable elements that move in the performance of the user exercise and in response to changes in operating parameters. In this case, the exercise device may include an input device adapted to receive a portable memory card which corresponds to any of a plurality of protocols. A processor may communicate with the input device and access one or more computer-readable media having computer-executable instructions for determining a format of the portable memory card received by the input device, selectively applying protocols corresponding to the determined format, accessing exercise data stored on the card, and changing one or more operating parameters of the device as it corresponds with the accessed exercise data. The accessed exercise data may then be delivered to the user. For instance, exercise data such as personal identifiers, exercise profiles, motivational content and the like may be visually or audibly delivered to the user. Similarly, exercise data such as an exercise program may be delivered by controlling the operating parameters of the exercise device in combination with any audio or visual content.

In yet another exemplary embodiment, a computer program product is usable with an exercise device and contains computer-readable media connected to the exercise device. The computer-readable media includes instructions for retrieving first fitness data from a portable memory card connected to the exercise device. Additionally, the retrieved first information may then be delivered to the user and second fitness data may be saved to the portable memory card. The first fitness data may be, for example, a user's personal information, an exercise program, motivational content, a workout history and the like. Similarly, the second fitness data may be a user's personal information, a workout history, and other similar data which is personalized for the user. In some cases, the second fitness data may also be an exercise program, such as where the program is created specifically for the user or where delivery of the program includes motivational content personalized to the user.

The exercise device may further include computer-readable media and computer-executable instructions for displaying exercise program parameters to a user which correspond to an exercise program deliverable to the user. Additional computer-executable instructions are included to allow the exercise device to determine a format of a portable memory card and communicate with the portable memory card, regardless of its format. For example, protocols may be selectively accessed so as to read and/or write data to the portable memory card, the protocols being selected based upon the determined format of the card.

Any of a variety of types and formats of exercise programs may be stored on the portable memory card or on the exercise device. For instance, an exercise program may be stored on a computer-readable medium such as a portable memory card, such that computer-executable instructions define an exercise program having a plurality of program segments during which at least one operating parameter of the exercise device is defined. The defined exercise program may further include motivational content tags which call corresponding content files which are accessible by the exercise device, even if the content files are stored independent of the defined program segments. For instance, the content tags may reference content files stored within a database within the portable memory card or the exercise device.

When the exercise program is accessed by the exercise device for delivery to the user, the movable element of the exercise device is controlled according to the one or more operating parameters defined by the program segments and motivational content is provided as it corresponds to the motivational content files and content tags within the program. The motivational content files may further be synchronized with the operating parameters of the exercise device or with control signals changing the operating parameters. Optionally, the motivational content files are stored in a manner that reduces the size of the exercise program, such as where, for example, the exercise program includes multiple tags to a single motivational content file.

The exercise program may be stored on a memory card or other computer-readable media in any acceptable manner. For example, a user may create a program and store it on the computer-readable media, or it may be created by a third-party, the exercise device, or a workout generator on the exercise device or computer-readable media. In creating the exercise program, the segments may be defined with one or more segment intervals and operating parameters during the segment intervals, and by inserting motivational content tags corresponding to motivational content files. The program may then be packaged and transferred to the user. For instance, packaging the program may include compiling computer-executable instructions into an executable, saving the program to computer-readable media, or saving motivational content files in a library or database.

These advantages in addition to other objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

In order that the manner in which the above recited and other advantages and features of the invention are obtained, a more particular description of the invention briefly described above will be rendered by reference to specific embodiments thereof that are illustrated in the appended drawings. Understanding that these drawing depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The present invention is directed to exercise devices that include one or more motors or other electrically driven actuators used to control one or more operating parameters of the exercise device. While the invention will be described in this context of a motorized treadmill, it should be understood that the invention is not limited to any particular type of exercise device or solely to exercise devices. To the contrary, the present invention can be readily adapted to any motorized device or any other device that utilizes motors, solenoids, or any other electrically driven actuators to control any operating parameter of the device, such as speed, resistance, incline, time, temperature, or other similar operating parameters. The term "device" or "devices" shall refer broadly to any type of apparatus that includes one or more stepper motors, solenoids, or other electrically driven actuators or controllers. Additionally, the term "exercise device" shall refer broadly to any type of device that takes the form of an exercise machine, including, but not limited to, treadmills, exercise cycles, Nordic style ski exercise devices, rowers, steppers, hikers, climbers, elliptical or striding exercise devices, and weight machines.

Figure 1:
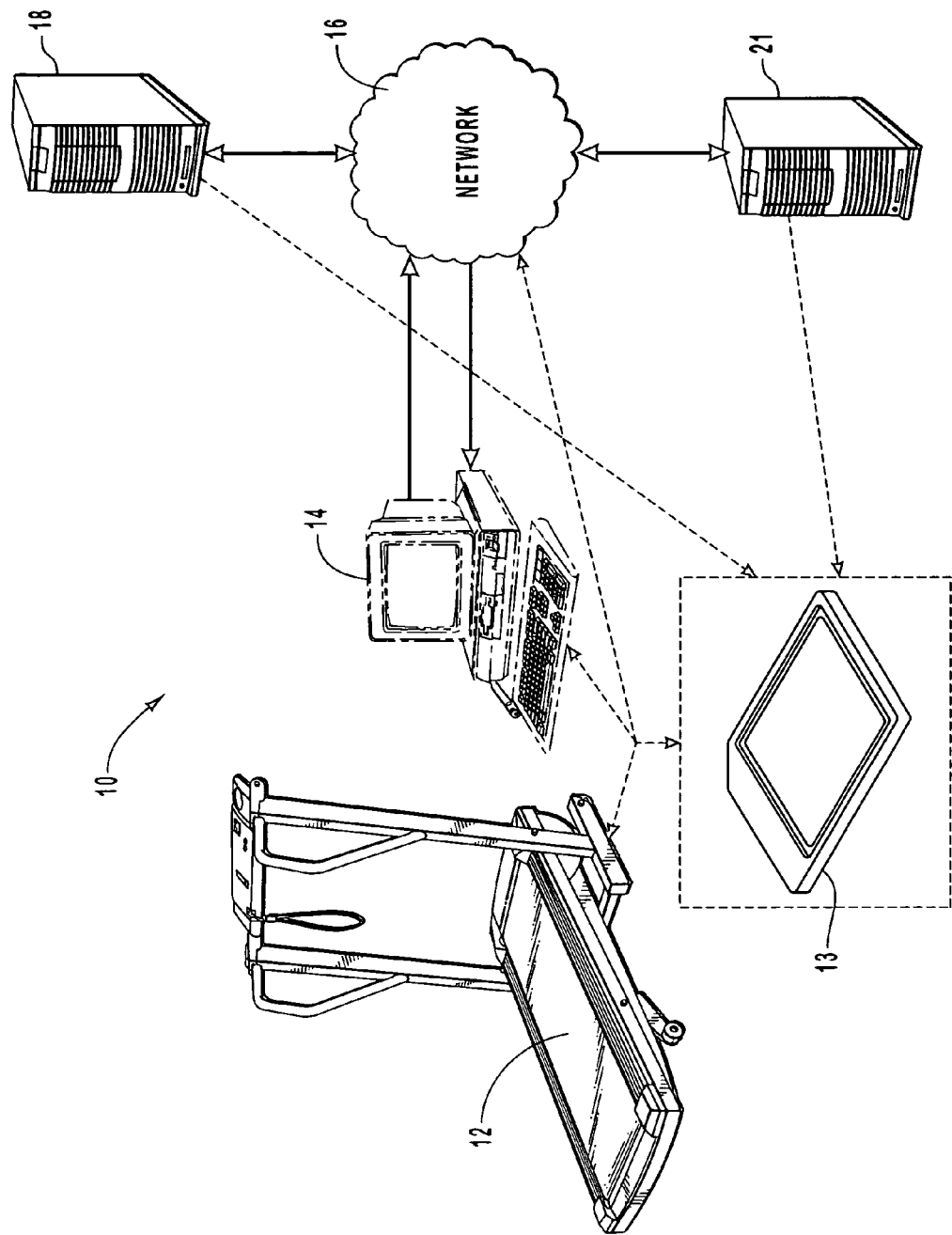
FIG. 1 is an exercise system according to one exemplary embodiment of the present invention.

Depicted in FIG. 1 is a representation of one illustrative system, designated by reference numeral 10, which may incorporate the novel features of the present invention, including various novel devices, hardware and software modules, and the like that may be remotely accessed and controlled in a real-time manner. As shown, one or more exercise devices 12, such as a treadmill, is in communication with one or more portable data storage devices, such as, for example, memory card 13. In addition, or in the alternative, treadmill 12 may communicate with a personal computer 14. For example, U.S. Pat. No. 6,458,060, issued Oct. 1, 2002 and entitled "Systems and Methods for Interaction with Exercise Device," which is incorporated herein in its entirety, describes exemplary systems, methods, and devices for communication between treadmill 12 and personal computer 14.

In addition, and as detailed in U.S. Pat. No. 6,458,060, treadmill 12 and personal computer 14 may further communicate with a network 16 that enables various hardware and software modules and devices to communicate one with another. Network 16 may, therefore, be a local area network (LAN), wide area network (WAN), wireless network, packetized network, real-time network, the Internet, and the like. Network 16 further facilitates communication of treadmill 12 with a communication system 18 (e.g. hardware and/or software associated with a data/program store and/or a website) and/or third party 21. In one embodiment, communication system 18 facilitates delivery of an exercise program to a user on treadmill 12, such that communication system 18 and/or third party 21 may act as a stored trainer or connect to a stored trainer. Optionally, communication system 18 and/or third party 21 may deliver an exercise program to personal computer 14, memory card 13, and/or treadmill 12 such that personal computer 14, memory card 13, and/or treadmill 12 may act as a stored trainer.

For example, in one embodiment, a user creates an exercise program on personal computer 14. The created exercise program, including any control signals, control signal instructions, and motivational content, may thereafter be run directly from treadmill 12 over a connection between computer 14 and treadmill 12. Similarly, a program may be downloaded from communication system 18 or third party 12 and stored on computer 14, or "streamed" real-time to treadmill 12 via computer 14. Alternatively, a program may be downloaded to memory card 13 connected or linked to personal computer 14. Thereafter, treadmill 12 may indirectly access the stored program on memory card 13 via personal computer 14. Alternatively, memory card 13 may be removable from personal computer 14 and directly connected or linked to treadmill 12 by, for example, insertion of memory card 13 into a complementary port of treadmill 12.

It may also be appreciated by a person having ordinary skill in the art, particularly in light of the discussion herein, that an exercise program may be obtained without being passed through computer 14. For example, communication system 18 and/or third party 21 may, individually and/or collectively, function as or include a personal trainer. The user of treadmill 12 may request one or more workouts from the personal trainer. Such workouts may be requested, for example, by Internet website request, telephone, video conference, mail, email, instant message, transfer of data indicative of the request from treadmill 12 to communication system 18 and/or third party 21, and the like. In response, the personal trainer may create requested exercise programs for the user. The newly created exercise programs, as well as any motivational content files, may then be packaged (e.g. encoded) for example, on one or more memory cards 13 and mailed or otherwise delivered to the user for use with treadmill 12. A memory card may then be accessed by a user and a stored exercise program delivered to the user.

In this manner, the exercise program on memory card 13 may be entirely customizable. For example, when requesting the exercise program, the user may supply user data or personal indicators such as the user's name, age, weight, gender, etc. This information may be stored on memory card 13 such that when the card is inserted into treadmill 12, treadmill 12 automatically recognizes the user and can set any necessary operating parameters or other data associated with that user. In addition, motivational content may be personalized by, for example, including music, images, or video in the workout that corresponds to user requests or that were provided by the user in the exercise program request. Alternatively, motivational content may be customized to include, for example, audio that uses the user's name in encouraging or motivating the user during the workout. Thus, motivational content and an exercise program are also properly regarded as user data. As will be appreciated, motivational content and exercise programs can be saved in a variety of manners. For instance, in one embodiment, motivational content and exercise programs are saved in files on computer-readable media, and such files may be proprietary or industry standard. For example, audio motivational content may be stored in an MP3, WAV, MP4, MIDI, or any of a variety of other formats.

The following discussion will be directed to only a single treadmill 12; however, it may be appreciated that a similar discussion may be provided for multiple treadmills or multiple exercise devices. In addition, although only one of each element of system 10 is depicted, it may be appreciated by one skilled in the art that system 10 may have a mixture of both single and multiple elements, for example, at least one treadmill 12, memory card 13, personal computer 14, network 16, communication system 18, and third party 21. Alternatively, one or more of the elements of system 10 may be eliminated or the functionality thereof incorporated within the structure and function of one or more of the other elements of system 10.

Similarly, although each of the elements of system 10 are shown separated one from another, it may be appreciated by one skilled in the art that the hardware and/or software elements of the present invention may be incorporated within two or more elements. For example, personal computer 14 may be incorporated within treadmill 12. Similarly, the hardware and/or software elements of third party 21 may be incorporated within communication system 18.

As defined herein, the term "third party" may include: (i) a live human being; or (ii) a stored trainer, such as a website, computer, optical media (e.g., compact disk or digital video disk), visual media, magnetic media (e.g., videotape, readable disk), an electronic monitoring system, dynamic computer readable instructions, interactive and/or dynamic software programs, computer readable instructions, and/or other media and hardware and/or software modules and components, whether or not the trainer is located at treadmill 12 or at some other location. In one embodiment, the third party is another trainer.

Generally, system 10 enables exercise programming with control signals to be transmitted from a portable data storage device such as memory card 13, to a user at treadmill 12. As disclosed in U.S. Pat. No. 6,312,363 entitled "Systems and Methods for Providing an Improved Exercise Device with Motivational Programming," which is incorporated herein by reference in its entirety, the programming may include motivational content and/or one or more control signals that may be used to control the operating parameters of treadmill 12 in real-time in an uninterrupted manner. The control signals may be synchronized with the motivational content and designed to control one or more operating parameters of the exercise device, such as the speed, incline, resistance, difficulty of exercise program, duration, distance, and the like of an exercise program performed on treadmill 12.

As used herein, the term "motivational content" is used to broadly refer to any audio material, including dialog, narration, sound effects, and/or music, either alone or in combination with video material. In one embodiment of the present invention, the motivational content is stored in memory card 13 and includes an audio and/or video presentation of a personal trainer and others engaged in a series of exercises of varying difficulty. In another embodiment, the programming includes an exercise profile representative of the exercise and includes by way of example and not limitations, speed, incline, or resistance of the exercise device, which is displayed continually or periodically to the user during the performance of the programming. In yet another embodiment of the present invention, the user controls the period during which the exercise profile appears. One skilled in the art may appreciate that various other configurations of programming and motivational content are applicable.

An embodiment of a real-time signal may include motivational content, control signals, and/or control signal instructions, whether or not such control signals or instructions are synchronized with the motivational content. Alternatively, the real-time signal may include only the motivational content, other signals representative of measurable parameters of the exercise device (e.g. speed, inclination, resistance, etc) and/or a user of the exercise device (e.g. heart rate, blood pressure, etc), and the like. For example, treadmill 12 may transmit one or more signals to memory card 13. The signal may include parameters such as the status of an exercise program performed on the device, e.g. active status (i.e., on), deactivated status (i.e., off), standby status (i.e., waiting), distance covered, duration, calories burned, speed, inclination, resistance, and the like. Additionally, the signal may include parameters regarding the user, such as heart rate, blood pressure, and the like. In other configurations, the motivational content and/or the control signals are delivered to treadmill 12 and no data is passed to memory card 13 from treadmill 12.

As mentioned above, the control signals control the operating parameters of treadmill 12, such as speed, inclination, resistance, and the like. Such control may be achieved by a user of treadmill 12, an exercise program saved on treadmill 12, and/or an exercise program saved on memory card 13. The present invention, therefore, allows control of a device, such as an exercise device, without the need to interrupt other portions of programming, such as real-time audio and/or video.

FIGS. 2 through 5 generally depict a typical motorized, reorienting treadmill 12. Although an example of the present invention will be described with respect to the functionality and operability of a treadmill, it will be understood by those skilled in the art that the present invention may be used or incorporated within any exercise device or other device.

Treadmill 12, in one embodiment, includes a control panel 22 supported on a generally upright support structure 24 and a tread base 26. Upright support structure 24, in this illustrative embodiment, includes two side members 28, 30 coupled together by way of one or more cross members 32. Side members 28, 30 and cross members 32 may have various configurations and may be fabricated from various materials so long as they are capable of supporting control panel 22 and tread base 26. For example, the elements of upright support structure 24 may be fabricated from, but not limited to metals, plastics, composites, combinations thereof, and the like. Additionally, one skilled in the art may appreciate that various other exercise devices may have different upright support structures, side members, and cross members, or be devoid of one or more of such structures and members.

Figure 4:
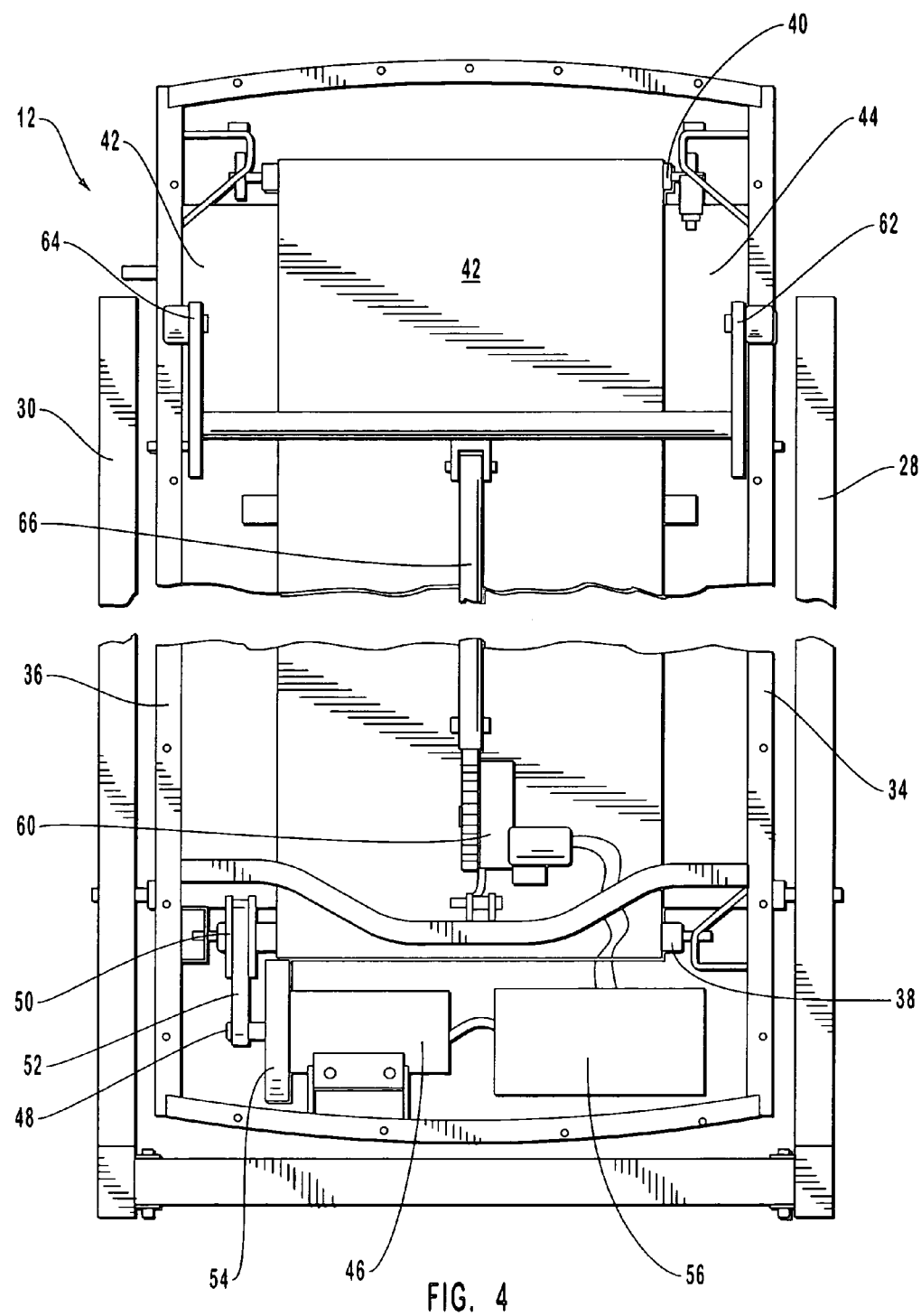
FIG. 4 is a partial plan view of portions of the exemplary reorienting treadmill illustrated in FIGS. 2 and 3 with the treadmill oriented in the second or storage position and with the bottom cover removed, revealing some of the internal components of the treadmill.

The tread base 26 typically includes a pair of side rails 34, 36 each having a front portion proximal to and a rear portion distal from upright support structure 24 when tread base 26 is in a downward exercisable position. As shown in FIG. 4, a front pulley 38 and a rear pulley 40 are disposed between and supported by side rails 34, 36, while a continuous belt 42 extends between and around front and rear pulleys 38 and 40, respectively. Pulleys 38, 40 and belt 42 may have various configurations and be fabricated from various materials, as known by one skilled in the art and commonly known within the exercise industry.

A deck 44, commonly fabricated from wood, typically supports the upper run of belt 42 and supports an exercising individual resting upon belt 42. Although deck 44 is preferably of a cellulose material such as wood, various other types of material may be used so long as deck 44 is capable of supporting belt 42 and a user exercising thereupon.

As best seen in FIG. 4, in one embodiment, front pulley 38 is mechanically coupled to an electric tread drive motor 46 by way of pulleys 48 and 50 and a drive belt 52. In this illustrative embodiment, motor 46 can further incorporate an inertial flywheel 54 that controls fluctuations in the rotational motion of a shaft of motor 46 during operation of treadmill 12. Motor 46 is optionally electrically coupled to a treadmill controller 56 that controls the operation of motor 46, and thus the speed of belt 42, in response to various user inputs or other control signals. As shown, treadmill controller 56 is incorporated within tread base 26; however, it may be appreciated by one skilled in the art that treadmill controller 56 may be incorporated within control panel 22 or alternatively within personal computer 14.

Figure 5:
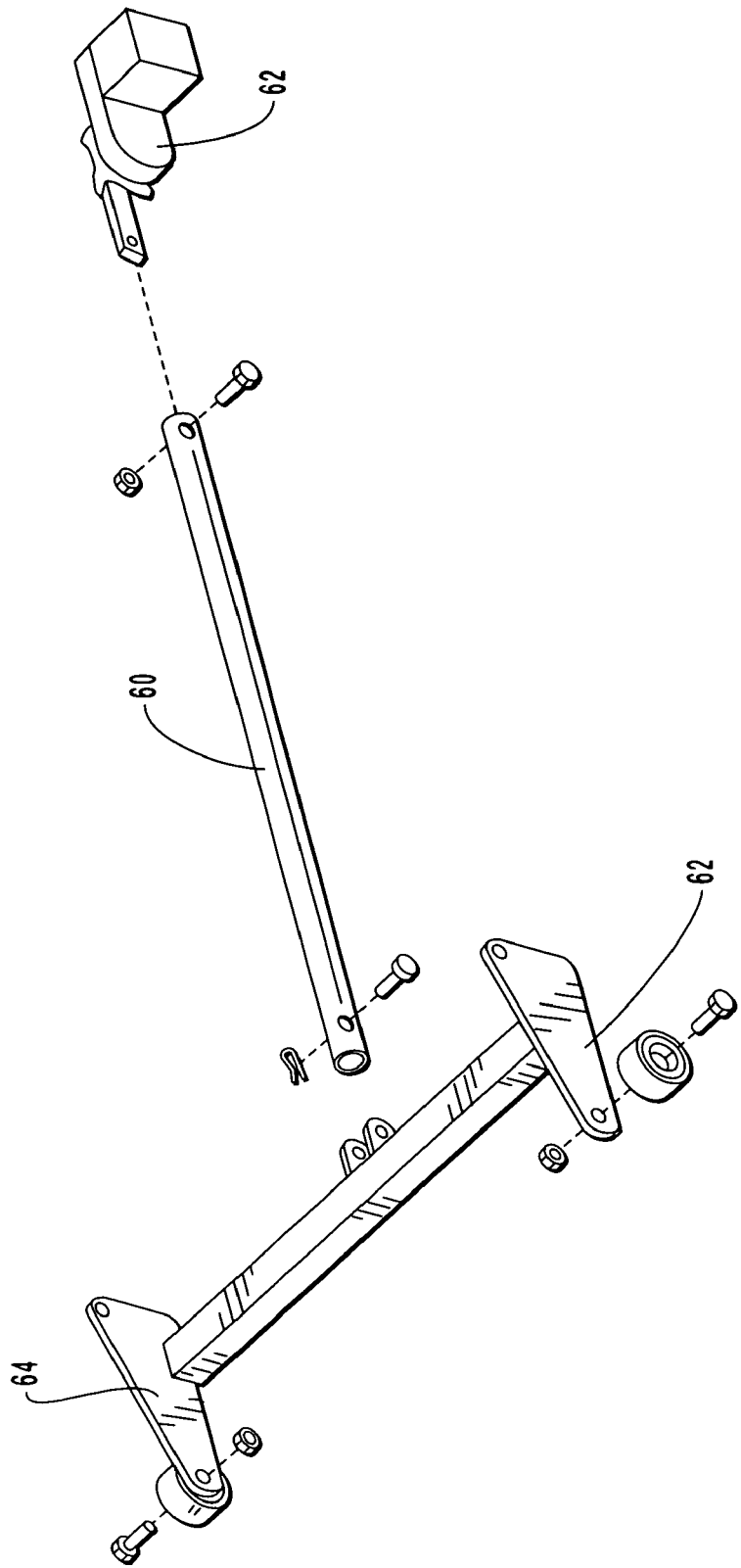
FIG. 5 is a partial exploded perspective view of the incline mechanism incorporated into the exemplary treadmill illustrated in FIGS. 2 through 4.

In addition to the ability to control and vary the speed of belt 42, treadmill 12 also permits the degree of incline of tread base 26 relative to the floor, or other surface upon which tread base 26 rests, to be varied. Typically, this is accomplished through the use of an incline drive motor 60 that rises or lowers one end of tread base 26 relative to the other end. In the embodiment illustrated in FIGS. 2 through 5, tread base 26 includes a pair of rear feet 62 and 64 that are rotatably attached to the rear of portion of side rails 34, 36. As best seen in FIGS. 4 and 5, feet 62 and 64 are mechanically coupled through a shaft 66 to incline drive motor 60, which causes feet 62 and 64 to pivot about their points of pivotal attachment to side rails 34, 36, thereby selectively raising or lowering the rear end of tread base 26 relative to the front end thereof. Motor 60 is also optionally electrically coupled to, and controlled by the treadmill controller 56.

Figure 2:
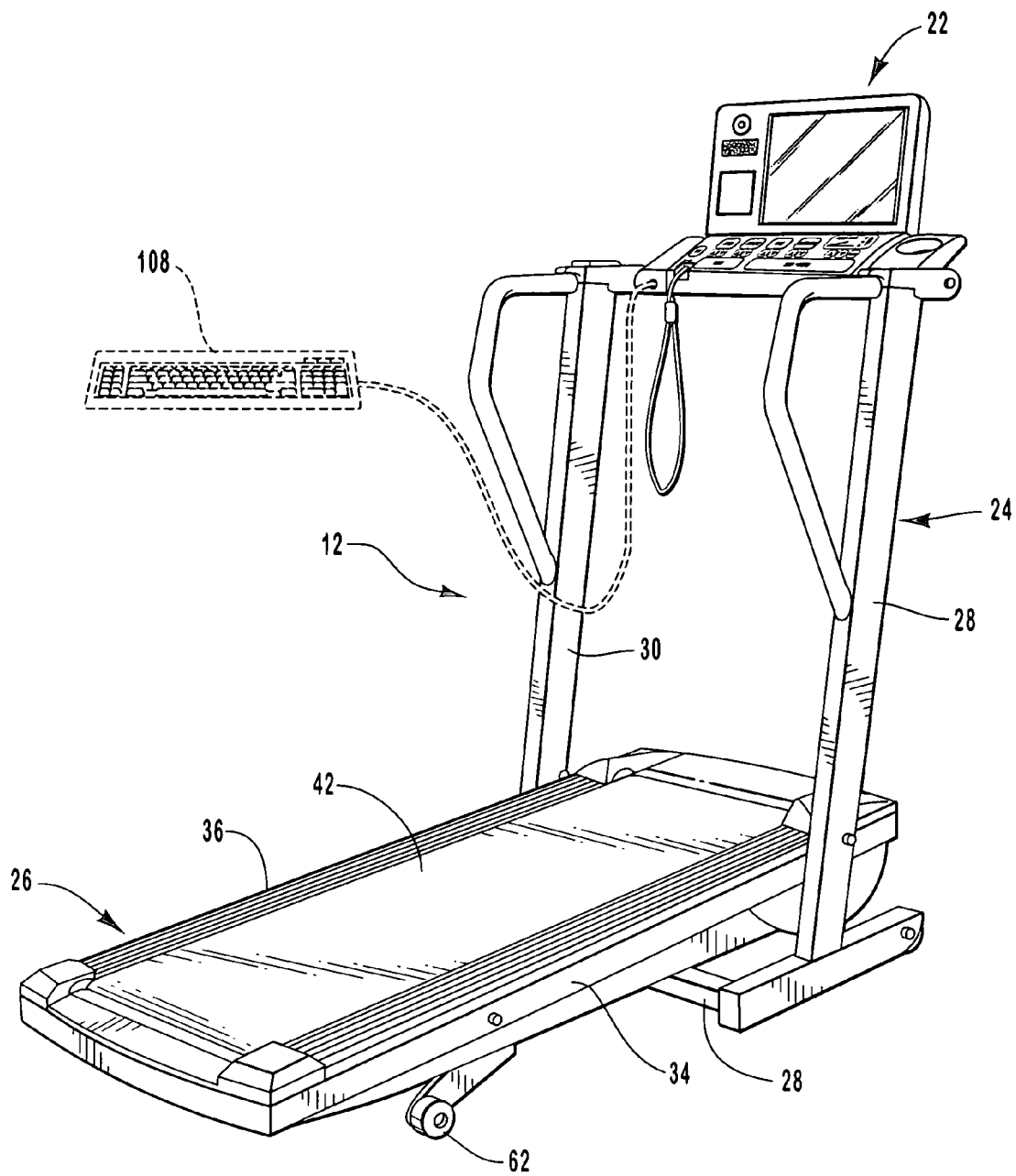
FIG. 2 is a perspective illustration of an exemplary reorienting treadmill with the tread base positioned in a first position for a user to perform exercises to be used in the exercise system of FIG. 1.
Figure 3:
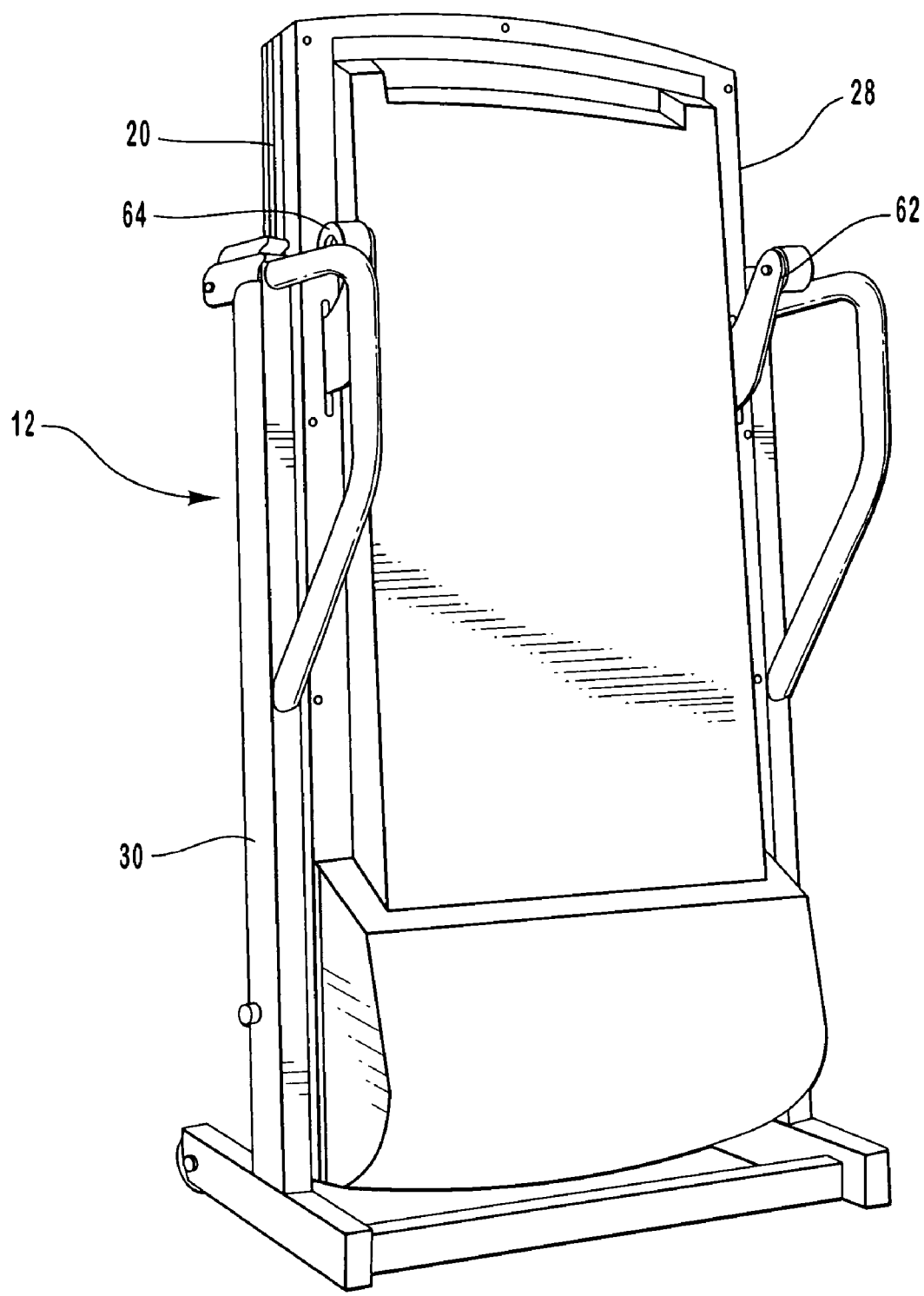
FIG. 3 is a perspective illustration of the exemplary reorienting treadmill of FIG. 2 with the tread base positioned in a second or storage position.
Figure 6:
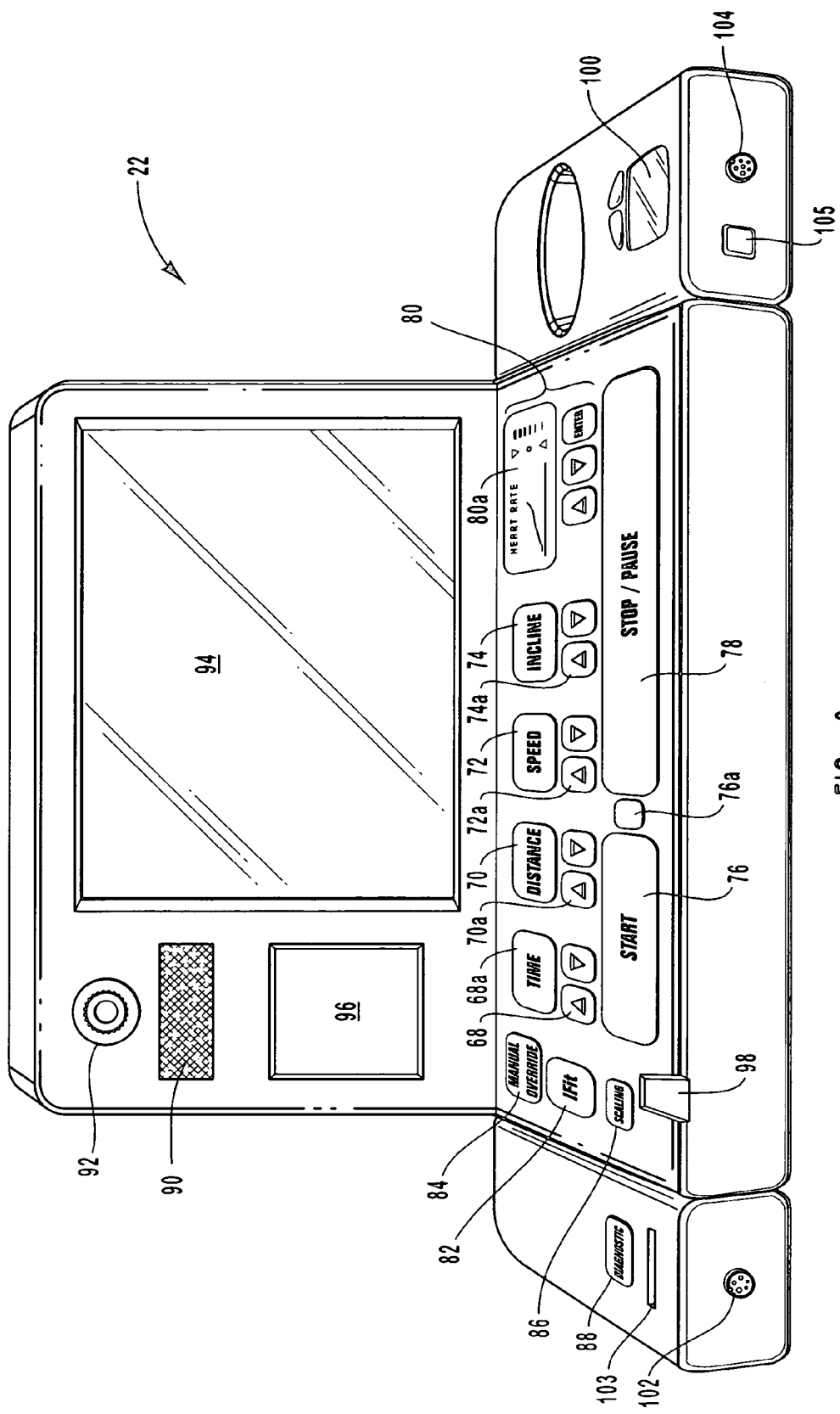
FIG. 6 is a perspective illustration of an exemplary control panel of the exemplary reorienting treadmill of FIG. 2.

As shown in FIG. 2, treadmill 12 includes control panel 22 attached to side members 28, 30 of upright support structure 24. Control panel 22, in one embodiment, as shown in FIG. 6, includes one or more interface devices. Such interface devices may function as input devices, output devices, or both input and output devices, such as, but not limited to, touch sensitive visual displays. Input devices enable a user to input and vary the operating parameters of treadmill 12. As examples of such input devices, control panel 22 includes many typical controllers for use on an exercise device, such as a treadmill. A number of illustrative input devices include, but are not limited to, speed controls 72, incline controls 74, time controls 68, distance controls 70, a start button 76, a stop or pause button 78, and heart rate controls 80. In addition to these input devices, such as one or more controllers, control panel 22 further optionally includes an iFit.com button 82, a manual override button 84, and a scaling control 86, each of which are also examples of input devices. It may be appreciated that each of the above-recited controllers or buttons may be embodied in a variety of different manners to perform their commonly utilized function. In addition, each controller, button, and the like may take the form of one or more switches, rheostats, potentiometers, touch sensitive controls, voice activated controllers, and the like. The input devices described herein are examples of structures capable of performing the function of interface means for gathering a first signal (such as a real-time signal) from the user. One skilled in the art may identify various other configurations of interface means that are capable of performing the desired function.

As shown in FIG. 6, iFit.com button 82, in one embodiment, acts as both a selector and an indicator of connectivity of treadmill 12 to communication system 18, third party 21, and/or memory card 13, whether such connectivity is via personal computer 14 or directly from treadmill 12. The iFit.com button 82 optionally includes an indicator light (not shown) that demonstrates when a connection has been established between treadmill 12 communication system 18, third party 21, and/or memory card 13, such as when iFit.com button 82 is depressed. Alternatively, a light emitting diode (LED) positioned in close proximity to iFit.com button 82 may be activated when iFit.com button 82 is activated. The connection achieved by activating iFit.com button 82 may be via a variety of communication line connections.

Control panel 22 can also include a stored data port 103 for directly receiving and accessing a data storage medium such as, for example, flash, magnetic, or optical storage media. Alternatively, stored data port 103 may be located on tread base 26. A user can insert memory card 13 into stored data port 103 to provide treadmill 12 (FIG. 1) with access to user data and/or exercise programming, including motivational content, control signals, control signal instructions, exercise profiles, and program definitions, which can be used to control one or more operating parameters of the exercise device, such as treadmill 12. Treadmill 12 can identify the availability of additional exercise programming upon insertion of the data storage medium into stored data port 103 or upon activation of one or more of the interfaces of treadmill 12, such as but not limited to, the activation of the iFit.com button 82.

In addition, control panel 22 may include a wireless port 105 that enables treadmill 12 to wirelessly communicate with network 16 (FIG. 1), either directly or via personal computer 14. Optionally, various other types of ports or interfaces may be included within treadmill 12 to enable communication via one or more communication line connections. For example, treadmill 12 may include one or more ports and interfaces to enable communication line connection through existing broadcast technology, including television broadcast over the airwaves, cable or cable modems, satellite, telephone lines, whether analog or digitally based, the internet, DSL, G-Lite, wireless technology, infra-red (IR) technology, other high-speed data connections, or any other suitable transmission technology or medium. Optionally, a communication port on a user treadmill may enable communication directly with another treadmill (such as in a master/slave scenario), whether or not such communication utilizes a network.

By activating the iFit.com button 82, in one configuration, a signal may be generated and transmitted to memory card 13, which is connected or linked to treadmill 12, personal computer 14, or communication system 18, so as to create a connection therebetween. In this manner, treadmill 12 may receive signals representative of exercise programming from memory card 13 or communication system 18, and thereby enable a user to obtain the services of a stored trainer or personal trainer to perform exercise programming. Additionally, connecting treadmill 12 with memory card 13, computer 14, and/or communication system 18 enables the user to listen to audio programming, view video programming, review and update user information and statistics, load user statistics, update exercise software and operating parameters, and the like.

A connection between treadmill 12 and at least one of network 16 and communication system 18 further enables one or more users to interact one with another, and optionally compete one against another. For example, a first user on treadmill 12 may access an exercise program stored on memory card 13. While using the exercise program, treadmill 12 may receive information regarding the same exercise program being simultaneously performed by a second user on a similar treadmill via network 16 and/or communication system 18. In this manner, the first user may then compete against the second user and vice versa. This competition may be live-on-live or time adjusted, e.g., a workout recorded previously by the second user which the first user competes against.

As mentioned above, control panel 22 may include manual override button 84. Manual override button 84 enables a user to override an action initiated by a stored trainer, such as an exercise program stored on memory card 13, within the memory of personal computer 14, in memory stored in treadmill 12, or transferred from communication system 18. For example, if the accessed exercise program is too difficult for the user, the user may activate manual override button 84 thereby interrupting the program delivered to the user by treadmill 12. Similarly, in the event that the exercise program is too easy, the user may increase the difficulty level of the exercise program being delivered by the exercise device. Consequently, manual override button 84 provides the user with a safety switch during operation of treadmill 12. In an alternate configuration of treadmill 12, the functionality of manual override button 84 is activated upon manual activation of one of the other input devices, such as but not limited to, incline controls 74, speed controls 72, stop/pause button 78, and the like, or upon automatic recognition of measurable parameters of the user, such as an elevated heart rate, blood pressure, and the like.

Similar to the operation of manual override button 84, scaling control 86 enables a user to vary the operating parameters of treadmill 12 during an exercise program initiated by treadmill 12. A user may activate scaling control 86 and vary the intensity of an exercise program. The scaling control 86, therefore, enables a user to select one or more values representative of a proportional or other change to be made to the control signal or exercise program received by treadmill 12 from memory card 13 and/or communication system 18. For example, if an exercise program requires a maximum speed of 6 miles per hour (mph) with a maximum incline of 15 degrees for a period of 30 minutes, an individual may activate scaling control 86 to require only 66% intensity of the exercise program; stated otherwise, reduce the intensity by one third. Therefore, the exercise program is varied to a maximum speed of 4 mph, with a maximum incline of 10 degrees, for a period of 20 minutes. Optionally, scaling control 86 may enable the user to set maximum values for each operating parameter of treadmill 12, or adapt the workout to obtain a desired distance or program duration. In another configuration, scaling control 86 may enable the user to scale only one operating parameter of treadmill 12 while leaving other parameters unchanged. Hence, the user may vary the exercise program to their particular abilities, while obtaining the beneficial effects of exercising.

As another example of an input device of the present invention, control panel 22 may include a diagnostic control 88. Upon activation of diagnostic control 88, whether by depressing a button or by some other manner known to one skilled in the art, treadmill 12 communicates with memory card 13 and/or communication system 18 to check the operating status of the exercise device. Memory card 13 and/or communication system 18 may include diagnostic modules which send signals to the internal hardware and software modules of treadmill 12 to verify that the modules are operating within the desired specifications or to determine whether treadmill 12 may include software for which an update is available. In one embodiment, in the event that one or more of the hardware and/or software modules are damaged or not performing as required, treadmill 12 may download one or more software updates from memory card 13 or communication system 18, if possible. Alternatively, a diagnostic module may inform the user that an error has occurred and advise that the user obtain maintenance of the hardware or software components of treadmill 12.

As additional examples of input devices, according to another aspect of the present invention, control panel 22 may include an audio input device 90 and a video input device 92. Audio and video input devices 90, 92 enable a user to perform communication, such as real-time communication, with other users of exercise devices, via communication system 18 (FIG. 1). The diagnostic control 88, audio input device 90 and video input device 92, therefore, are structures capable of performing the function of interface means, communicating with the exercise mechanism, for gathering a first signal from the user. Various other configurations of such interface means are known to one skilled in the art in view of the teachings contained herein.

In one embodiment, audio input device 90 may take the form of a microphone, while video input device 92 may take the form of a video camera. Audio input device 90 and video input device 92 may alternatively take various other configurations as known by one skilled in the art. For example, audio input device 90 may be a microphone detachably connected to control panel 22 or another part of treadmill 12. In another configuration, audio input device 90 may be located distant from treadmill 12, while being capable of gathering the audio inputs from the user. In still another configuration, audio input device 90 may be eliminated from treadmill 12, while treadmill 12 includes an audio jack, such as an RCA-type audio jack, RJ-type jacks, digital audio jack, and the like. In still another configuration, audio input device 90 may be a radio frequency (RF), infra red (IR), or wireless type microphone. Similarly, video input device 92 may have the configuration of a digital video camera integrally formed within control panel 22. Alternatively, video input device 92 may be detachably connected to control panel 22 or another part of treadmill 12, such as wireless digital cameras. In still another configuration, video input device 92 may be located distant from treadmill 12, while being capable of gathering the requisite video signals to be transmitted to communication system 18 (FIG. 1).

In addition to the above-described audio and video input devices 90, 92 respectively, control panel 22 may include a variety of other input devices. For example, control panel 22 may include an integrally formed mouse 100. Additionally, control panel 22 may include a keyboard jack 102 for an external keyboard 108 (FIG. 2), a controller port 104 for receiving one of a variety of game controller, a touch-sensitive video display, and various other ports, jacks, or the like to receive various other external components. Each input device is adapted to allow a user operating treadmill 12 to more fully operate one or more operating parameters of treadmill 12. These additional input devices are further examples of structures capable of performing the function of interface means, communicating with the exercise mechanism, for gathering a first signal from the user.

Control panel 22, in one embodiment includes one or more output devices that provide a visual and optionally an audio indication of the operational status of treadmill 12 to the user. As with the input devices, the output devices may have various configurations and perform numerous functions. Generally, the output devices described herein are each structures capable of performing the function of means for reproducing a signal. The output devices and hence the means for reproducing a signal may have various configurations as known to one skilled in the art in view of the teaching contained herein. In one embodiment, one visual output device 94 may be a video display. Generally, visual output device 94 presents the user of treadmill 12 with information and data stored on treadmill 12, or received from memory card 13 or communication system 18. Additionally, visual output device 94 may optionally show information and data from: (1) various other sources selected by the user, third parties, or system 10; (2) statistical information representative of the operational parameters of treadmill 12, such as the speed, incline, duration of user's workout, etc.; (3) electronic mail messages (e-mail), and the like. Output display device 94, in one embodiment, is a liquid crystal display (LCD) or cathode ray tube (CRT) display. In another embodiment, visual output device 94 is an LED dot matrix display.

One skilled in the art may appreciate that various other devices may be used to perform the functions of visual output device 94. For example, visual output device 94 maybe an electroluminescent display (ELD), a gas-plasma display, a thin film transistor (TFT) display, a virtual reality (VR) display, and the like. In another embodiment of the present invention, control panel 22 includes multiple visual output devices 94. In still another embodiment, visual output device 94 is adapted to permit split screen or layered images that are associated with picture-in-picture viewing of various images and information. For example, visual output device 94 may allow a user to watch various types of entertainment and/or surf the Internet, while receiving images representative of an exercise profile of an available exercise program, whether the program is being selected, delivered, activated, or the like.

As shown in FIG. 6, in one embodiment of the present invention, control panel 22 includes an audio output device 96, such as a speaker. Audio output device 96 performs a similar function to that of visual output device 94 in that audio output device 96 provides the user with audible signals representative of the operational parameters of treadmill 12. Additionally, audio output device 96 may deliver audio, visual, or control signals to the user from memory card 13, communication system 18, or third party 21. Such signals may be audible and/or inaudible signals. Various speakers are contemplated and may operate as audio output device 96, for example, hardwired and wireless speakers, such as computer speakers, audio system speakers, and the like. Control panel 22 may optionally include one or more amplifiers (not shown), in cooperation with audio output device 96. Furthermore, audio output device 96 may be circumvented through use of one of a variety of audio jacks that enable a user to listen to the audio output through headphones or similar audio transmitting device.

In addition to the output devices described above, the present invention may include various other output devices to provide information and data to the user of treadmill 12. In one embodiment of treadmill 12, control panel 22 includes one or more operating parameter displays. The one or more operating parameter displays give a visual display of some or all of the exercise device operating parameters, such as, but not limited to, speed, incline, distance traveled, calories burned, elevation climbed, wheel resistance, and the like. The one or more operating parameter displays may use a numerical display, a graphical display, combinations thereof, or such other displays known to one skilled in that art. For example, the operating parameter display may be incorporated within visual output device 94.

As shown in FIG. 1, communicating with treadmill 12 via personal computer 14 is communication system 18. Those skilled in the art will appreciate that computer 14 may take various configurations, including personal computers, handheld devices, multi-processor systems, microprocessor-based or programmable consumer electronics, telephones, network PCs, minicomputers, mainframe computers, and the like. Additionally, computer 14 may be part of a distributed computer environment where tasks are performed by local and remote processing devices that are linked (either by hardwired links, wireless links, or by a combination of hardwired or wireless links) through a communications network, such as network 16. Furthermore, as noted previously, treadmill 12 may optionally incorporate the functionality of personal computer 14 therein or include one or more modules or components of computer 14 while not incorporating all the modules and components of computer 14.

A more particular discussion of certain examples of alternate structures and operations of computer 14 is not necessary for a full understanding of the present invention. Nevertheless, such a discussion is provided in U.S. Pat. No. 6,458,060, which is herein incorporated in its entirety.

The discussion above describes a computer detached from treadmill 12; however, as appreciated and stated earlier, all or portions of computer 14 may optionally be incorporated within treadmill 12. As such, some or all of the various elements of computer 14 may be incorporated within control panel 22, or alternatively within tread base 26. In various other configurations of the present invention, therefore, control panel 22 may include one or more magnetic hard disk drives, magnetic disk drives, optical disk drives, and associated interfaces, either in addition to, or as alternatives to stored data port 103. Control panel 22, therefore, may be capable of accessing programming that is stored on computer diskettes, CDs (e.g. ROM, R, RW, etc.), DVDs, and the like. Additionally, control panel 22 may optionally include a keypad integrally formed therein, a touch-keypad on visual output device 94, or optionally include a standard keyboard interface that may enable a user to communicate with treadmill 12. The keypads and keyboard facilitate control of treadmill 12 by the user, and optionally communicate with memory card 13, communication system 18, and/or other hardware or software modules that may be accessible on or through treadmill 12.

Generally, memory card 13 and/or computer 14 collectively or individually are examples of a communicating mechanism, communicating with the interface means (e.g., the input devices of control panel 22 that gather a signal). In one embodiment, the communicating mechanism enables transmission of a first signal to treadmill 12 (e.g. input from a user on any of input devices 216). The communicating mechanism may also receive a corresponding second signal from treadmill 12, memory card 13, network 16, or communication system 18.

The second signal may be an exercise program and/or a control signal directed to the exercise device, such as treadmill 12, for example. In another embodiment, the second signal comprises user data which is uploaded into the memory of treadmill 12. For example, a user's name, age, weight, gender, and the like may be uploaded to treadmill 12 and optionally displayed on visual output device 94. In one embodiment, stored data port 103 and/or other interface modules of treadmill 12 are examples of a communicating mechanism, communicating with a portable data storage device.

In another embodiment, the communicating mechanism only receives the second signal. For example, upon merely activating a user input device, such as by turning the power of the exercise device or other device on, a first signal is gathered from the user, but is not transmitted. Alternatively, when a user inserts a memory card 13 into stored data port 103, a first signal is gathered, but is not transmitted. Instead, the first signal merely activates the power to treadmill 12 or the communicating mechanism and enables the communicating mechanism to download a second signal. Such a download may be, for example, initiated by the communicating mechanism or hardware or software modules on treadmill 12 or a portable data storage device. In another embodiment, the portable data storage device transmits the first signal and receives the second signal.

Figure 7:
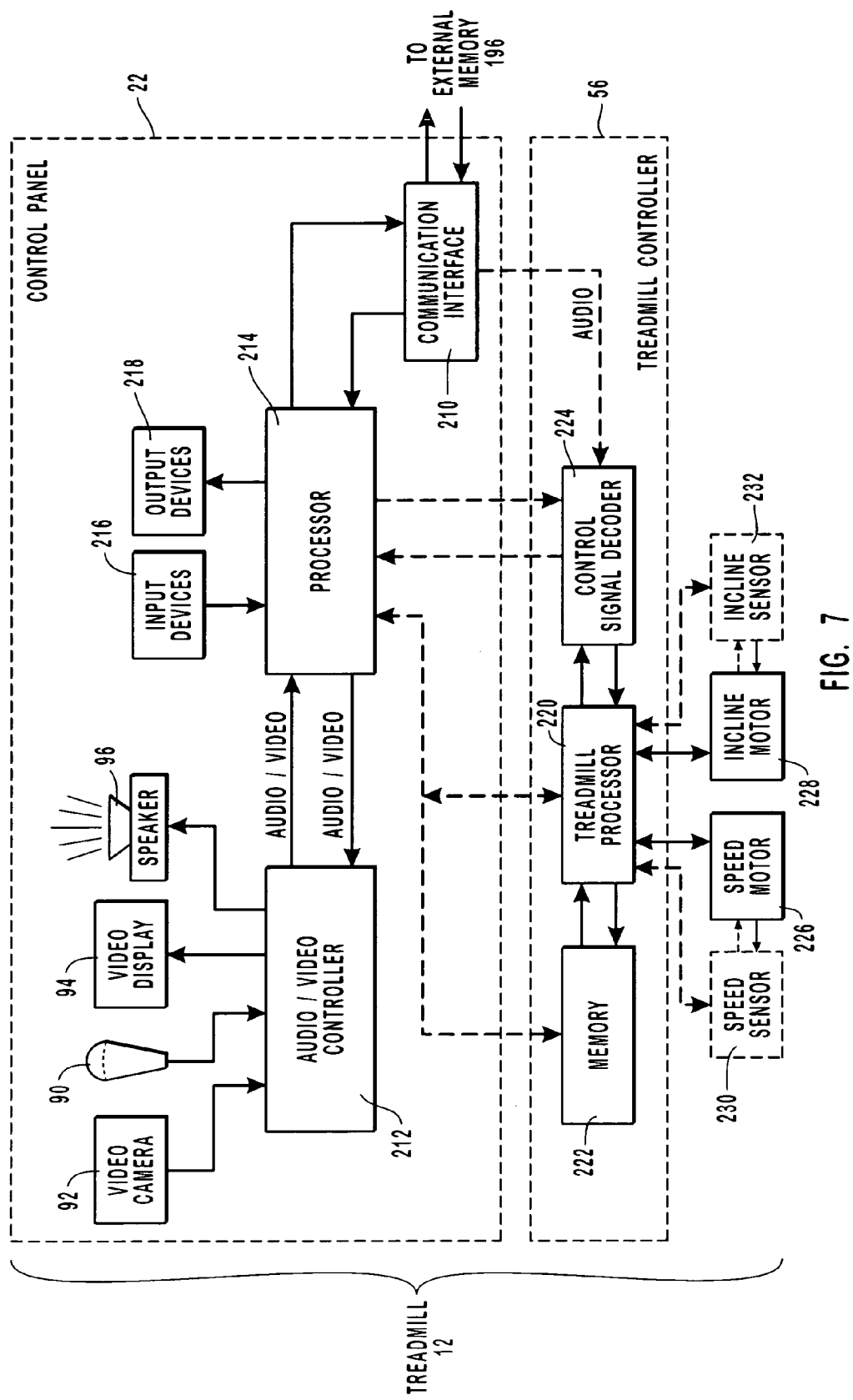
FIG. 7 is a functional block diagram of the exemplary treadmill of FIG. 1.

Referring now to FIG. 7, a functional block diagram of one embodiment of treadmill 12 is illustrated. In this particular configuration, the functionality of personal computer 14 is not incorporated within treadmill 12; however, as may be appreciated by one skilled in the art, computer 14 may be incorporated within control panel 22 or other portions of treadmill 12. This embodiment enables communication between a user operating treadmill 12 and exercise programs, user data, motivational content, and the like which are stored in an external memory 196, such as a portable data storage device or other memory located externally to treadmill 12 but accessible by treadmill 12.

As shown, treadmill 12 includes control panel 22 and treadmill controller 56. Although shown separated, it may be appreciated that portions of each may be combined together, thereby simplifying the modules and components of the present invention. Control panel 22, in this embodiment, incorporates audio input device 90 in the form of a microphone and a video input device 92 in the form of a video camera for gathering audio and video signals to be transmitted to communication system 18. Audio input device 90 and video input device 92 are illustrated merely as one embodiment of control panel 22, and, as mentioned previously, need not be incorporated within control panel 22 or other portions of treadmill 12.

In the illustrated embodiment, control panel 22 includes a processor 214. Processor 214 converts received data into a desired form that is capable of being transmitted to, for example, treadmill controller 56, output devices 218, visual display 94, speaker 96, program translator 211, and external memory 196 (via communication interface 210). As such, processor 214 may perform various operations on the data to be delivered such as, but not limited to, packing, depackaging, encrypting, and the like. Additionally, processor 214 may be configured to perform various operations to data received from external memory 196, such as, but not limited to, the same or reverse of the above operations. Generally, processor 214 may have various configurations to perform the above-described function as known by one skilled in the art. For example, processor 214 may take the form of one or more micro-controllers, central processing unit (CPU), state machines, programmable logic arrays, or network of logical gates, ASIC processor, software-based controllers, a combination of these components, or a variety of other controllers.

Communicating with processor 214, in one embodiment, is communication interface 210 that enables treadmill 12 to transceive (i.e. transmit and receive) data with external memory 196. In one embodiment, communication interface 210 is a data port, such as stored data port 103 (FIG. 6). In another embodiment, computer interface 210 includes a data port as well as other hardware or software modules to facilitate communication with external memory 196, as will be discussed with respect to FIG. 8.

Communicating with processor 214 and optionally communicating with communication interface 210 is treadmill controller 56. As illustrated in FIG. 7, treadmill controller 56 communicates with control panel 22. Generally, treadmill controller 56 may communicate with control panel 22 by an I²C bus, an SPI bus, a microwire bus, a microbus, and the like.

In one embodiment, treadmill controller 56 includes a treadmill processor 220, memory 222, and a control signal decoder 224. Treadmill processor 220 is configured to control the operation of speed motor 226 and incline motor 228 that, respectively, control the speed and incline of treadmill 12. Treadmill processor 220, whether alone or in combination with other portions of control panel 22 and/or treadmill controller 56, is one structure capable of performing the function of means for controlling the operating parameters of the exercise mechanism and one structure capable of performing the function of control means for receiving one or more control signals from external memory, indicative of a selected exercise program and changing one or more operating parameters of the exercise mechanism based upon the selected exercise program and the one or more control signals.

Treadmill processor 220 is optionally controlled by processor 214 or by control signal decoder 224 in response to the various signals received through communication interface 210 from external memory 196. Alternatively, treadmill processor 220 may be controlled by signals obtained from memory 222, via input devices 216, audio input device 90, or video input device 92. Treadmill processor 220 may include various components and modules to perform the desired function. For example, treadmill processor 220 may include one or more micro-controllers, central processing unit (CPU), state machines, programmable logic arrays, network of logical gates, ASIC processor, software-based controllers, combination logic, a combination of these components, or a variety of other controllers.

Controller 212, processor 214, interface 210, and treadmill processor 220 are collectively and individually examples of structures capable of performing the function of communicating means, communicating with an interface means, for receiving a second signal, and optionally, for enabling transmission of a first signal.

Both processor 214 and treadmill processor 220 are capable of receiving and transmitting signals from the various elements of treadmill 12. For example, signals may include feedback from drive motor 226 and incline motor 228. Each processor 214, 220 is capable of converting the feedback signals into signals for the visual output device 94 or computer 14, or for writing a log or record of user activity and/or operation of the exercise device for transmission to external memory 196. The particular feedback signals received from speed motor 226 and incline motor 228 may be stored in registers or memory modules.

Treadmill 12, as depicted, optionally includes one or more sensors, such as speed sensor 230 and incline sensor 232. Each sensor 230, 232 gathers a particular operating parameter of treadmill 12 (speed of belt 42 (FIG. 4) and incline of tread base 26), such that control panel 22 may present outputs via the output devices that are indicative of the present operating state of treadmill 12 at any given point in time. Treadmill 12 may include other sensors that gather various other operating parameters, such as, but not limited to, maximum pulse and heart rate, average pulse and heart rate, target heart rate, length of workout session, and the like. Additionally, sensors 230, 232, optionally in combination with one or more other sensors, may determine whether an individual is actually exercising on treadmill 12 by, for example, measuring strain on motor 226, and deliver a feedback signal to processor 214 that informs communication system 18 or some output device.

As is further illustrated, processor 214 is further in communication with audio/video controller 212 for transmitting signals to visual display 94 and speaker 96, as well as receiving signals from audio input device 90 and video input device 92. Audio/video controller 212 is configured to manipulate the audio and video signals received from processor 214 in preparation for transmission to output devices 94, 96. Audio/video controller 212, therefore, includes one or more amplifiers, micro-controllers, central processing units, state machines, programmable logic arrays, network local logical arrays, or gates, ASIC processors, software based controllers, combination logic, or combinations thereof to both manipulate audio and video signals that are to be transmitted to output devices 94, 96 or received by associated input devices 90, 92.

Additionally, audio/video controller 212 may include memory, such as a cache or buffer, to store and aid with real-time transmission and delivery of audio and video signals. It may be appreciated by one skilled in the art that various audio/video controllers 212 are applicable and known in the art in light of the teaching contained herein.

According to another aspect of the present invention, processor 214 may receive various inputs from one or more manually operated input devices 216, such as time controls 68, distance controls 70, speed controls 70, incline controls 74, heart rate controls 80, manual override button 84, scaling controls 86, start button 76, stop/pause button 78, microphone 90, camera 92, and other controls and buttons known to one skilled in the art in light of the teaching contained herein. In response to such inputs, processor 214 may vary the operating parameters of treadmill 12 and provide the user with notification of such changes in the operating parameters of treadmill 12 via output devices 218 and/or visual output device 94 and audio output device 96. Alternatively, or in addition thereto, processor 214 may store the updated operating parameters of treadmill 12 in memory 222, and/or transmit the updated operating parameters to external memory 196 and/or communication system 18. Processor 214, therefore, is one structure capable of performing the function of means for controlling the operating parameters of the exercise mechanism and one structure capable of performing the function of control means for receiving one or more control signals from a communication system or memory device indicative of a selected exercise program, and changing one or more operating parameters of the exercise mechanism based upon the selected exercise program and the one or more control signals.

As discussed earlier, system 10 enables a user of treadmill 12 to communicate with external memory 196 and/or communication system 18, and thereby receive control signals to control one or more operating characteristics or parameters of treadmill 12. There are various manners by which treadmill 12 may be controlled by external memory 196 or communication system 18. Following hereinafter is a continued discussion of the operation of the illustrated embodiment of treadmill 12 depicted in FIG. 7 in communication with external memory 196, although the discussion is equally applicable to a connection with computer 14 or communication system 18.

During operation of treadmill 12 a user may initially insert a dead-man key (not shown) within port 98 of control panel 22 (FIG. 6). Upon insertion of the dead-man key, treadmill 12 is capable of being operated, i.e., power is allowed to flow to the various internal and external components of treadmill 12 and treadmill 12 has an active status. Once activated, a user may optionally connect to external memory 196 or use an internally stored or manually defined exercise program or workout. In the event that the user wishes to connect to external memory 196, in one embodiment, a user activates iFit.com button 82 (FIG. 6), thereby initiating the hardware and/or software modules within treadmill 12 to create a connection with external memory 196. Alternatively, the hardware and/or software modules within treadmill 12 are activated upon connecting external memory 196 to treadmill 12. For example, in one embodiment when external memory 196 is a portable memory device, e.g. memory card 13, upon inserting external memory 196 into stored data port 103, treadmill 12 is enabled to create a connection with external memory 196. In another alternative, upon placing treadmill 12 in active status, treadmill 12 automatically connects to external memory 196, whether such external memory 196 is insertable into or connectable or linkable to treadmill 12.

Once a link is achieved and a user optionally has provided user identification, a user may select an exercise program stored on external memory 196. Following the user selection, programming, whether live or stored is delivered (optionally in real-time) to communication interface 210 via one or more of a variety of connections. The particular configuration of communication interface 210 may vary based upon the particular formatting or protocols of external memory 196.

It may be appreciated by one skilled in the art that the stored exercise program may be displayed to the user in a variety of manners, depending on the particular signals received from external memory 196. For example, the stored exercise program may include an exercise profile that displays various parameters associated with the exercise program. For example, and as discussed in more detail hereafter, upon activation of the connection between treadmill 12 and external memory 196, a visual and/or textual representation of one or more stored exercise programs may be output to visual output device 94. In addition, once a program is selected, the exercise profile may be periodically or continually displayed on visual output device 94. Alternatively, the programming may include the above-described exercise profile only during selection of an exercise program. In such a case, measurable parameters of the user or device, educational or entertainment programming, music, video, and the like may be provided to the user of treadmill 12 via visual output device 94 and/or speaker 96 during the exercise program.

Upon running the exercise program, communication interface 210 may optionally deliver a control signal to control signal decoder 224 that generates a corresponding control instruction that is sent to speed motor 226 and/or incline motor 228 for a corresponding adjustment. In another setting, communication interface 210 may deliver both the control signal to processor 214 for manipulation and distribution to the appropriate hardware components, and/or software modules. Such delivery of programming may be performed through use of a general-purpose bus or a variety of other buses and protocols, such as an I²C protocol or bus, SPI bus, microwire bus, microbus, CAN protocol, home network protocol, or the like. Additionally, the control signals may be delivered using the CSAFE 1 protocol or equivalent thereof for various other types of devices not within the field of exercise devices.

In one embodiment, when communication interface 210 delivers signals to processor 214, processor 214 separates the control signals from any audio, video, or other signals, and optionally delivers them to audio/video controller 212, control signal decoder 224, treadmill processor 220, or memory 224. In another embodiment, the control signals are separated by communication interface 210 or delivered separately from external memory 196. For example, in one configuration processor 214 may optionally deliver portions of an audio or video signal to audio/video controller 212 while control signals are delivered to control signal decoder 224 either directly from communication interface 210 or through treadmill processor 220. In yet another configuration, processor 214 may optionally deliver a control signal to treadmill processor 220 that may include the functionality of control signal decoder 224 therein. The particular manner by which treadmill processor 220 retrieves either the encoded control signal or the decoded control signal may vary from configuration to configuration depending on the particular form of treadmill 12.

Generally, control signal decoder 224 either individually or collectively with processor 214 and/or treadmill processor 220 is one structure capable of performing the function of means for decoding the control signal having an input and an output. One skilled in the art may identify various other configurations of a means for decoding the control signal having and input and an output. For example, treadmill processor 220 and/or processor 214 may include a control signal decoder and hence be a means for decoding the control signal having an input and an output.

Following manipulation of the control signals to obtain the control instructions, treadmill processor 220 can perform the control process on the various components of treadmill 12 as dictated by the control instructions. For example, treadmill processor 220 may cause motor 46 to speed up thereby accelerating belt 42 or alternatively cause motor 60 to rotate thereby raising or lowering tread base 26. Motors 46, 60 and 226, 228 are structures capable of performing the function of means, electrically coupled to the output of the decoding means, for driving the moveable element in response to the decoded control signal. It may be appreciated by one skilled in the art that the control instructions may cause various other changes to the operating parameters of treadmill 12, and other devices. Similarly, various means for driving the moveable element in response to the decoded control signal are possible. For example, the means may vary depending on the particular type of exercise device used.

While treadmill processor 220 is either decoding the control signal from the signal received from external memory 196 or merely activating speed motor 226 and/or incline motor 228, processor 214 delivers any audio, video, textual, graphical, or similar signals received through communication interface 210, including any motivational content, to audio/video controller 212. Audio/video controller 212 manipulates the signals received and passes an audio signal to audio output device 96 and a video, textual, graphical, or other visual signal to visual output device 94. Optionally, processor 214 may send portions of the audio or visual signals to the output devices 218 to provide the user with multiple sources of representations of the current operating or measurable parameters of treadmill 12, or other exercise device.

Generally, communication interface 210, processor 214, audio/video controller 212, treadmill processor 220, and/or control signal decoder 224 are collectively and individually examples of a controller, responsive to a second signal configured to control the operating parameters of the exercise mechanism (preferably in real-time). Additionally, such a controller is a structure capable of performing the function of control means, communicating with the exercise mechanism, for receiving one or more control signals from the external memory indicative of the selected exercise program and for changing one or more operating parameters of the exercise mechanism based upon the selected exercise program and the one or more control signals. It may be appreciated by one skilled in the art that the control means may have various other configurations.

Following hereinafter is a generalized discussion of a number of features of exercise systems, exercise devices, methods, computer products, and computer readable media associated with the teaching and disclosure of the present invention. Generally, an embodiment of the present invention may comprise one or more hardware components, such as those described above and illustrated in FIGS. 1-7. Embodiments within the scope of the present invention also include computer-readable media for carrying or having computer-executable instructions or data structures stored thereon. Such computer-readable media can be any available media that can be accessed by a general-purpose or special-purpose computer and the hardware and/or software modules associated with system 10 (FIG. 1). By way of example, and not limitation, such computer-readable media can comprise RAM, ROM, EEPROM, CD-ROM, or other optical disk storage, magnetic disk storage, other magnetic storage devices, or any other physical medium which may be used to carry or store desired exercise programming or other program code means in the form of computer-executable instructions or data structures and which may be accessed by a general-purpose or special-purpose computer. For example, control panel 22 of treadmill 12 may be properly viewed as a special-purpose computer. Accordingly, when information such as one or more signals or programming provided from external memory through communication interface 210 or another communications connection to treadmill 12 is provided to treadmill 12, such connection is properly viewed as a computer-readable medium. Thus, any such connection is properly termed a computer-readable medium. Combinations of the above should also be included within the scope of computer-readable media. Computer-executable instructions may include, for example, instructions and data which cause a general-purpose computer, special-purpose computer, or special-purpose processing device to perform a certain function or group of functions.

Although not required, the present invention will be described in the general context of computer-executable instructions, such as program modules, that may be executed by one or more computers in various network environments, such as within the environments illustrated in FIGS. 1, 7 and 8. Generally, program modules include routines, programs, objects, components, data structures, etc. that perform particular tasks or implement particular abstract data types. Computer-executable instructions, associated data structures, and program modules represent examples of program code means for executing steps of the methods disclosed herein. The particular sequence of such executable instructions or associated data structures represents examples of corresponding acts for implementing the functions described in such steps.

According to this illustrative embodiment of the present invention, an external memory device storing user data, including one or more exercise programs, is directly connected to an exercise device for performing the stored exercise program and controlling one or more operating parameters of the exercise device used by a user performing the exercise program. However, it may be appreciated that the systems, methods, and devices of the present invention may be implemented and utilized in various other situations and with various other exercise devices or other devices unrelated to exercise devices. The systems and methods of the present invention may be implemented using a variety of hardware and/or software modules and include a variety of computer network configurations, including but not limited to multiple internal or external memory devices, and/or multiple exercise devices that are connected via the Internet, LANs, WANs, and the like.

Figure 8:
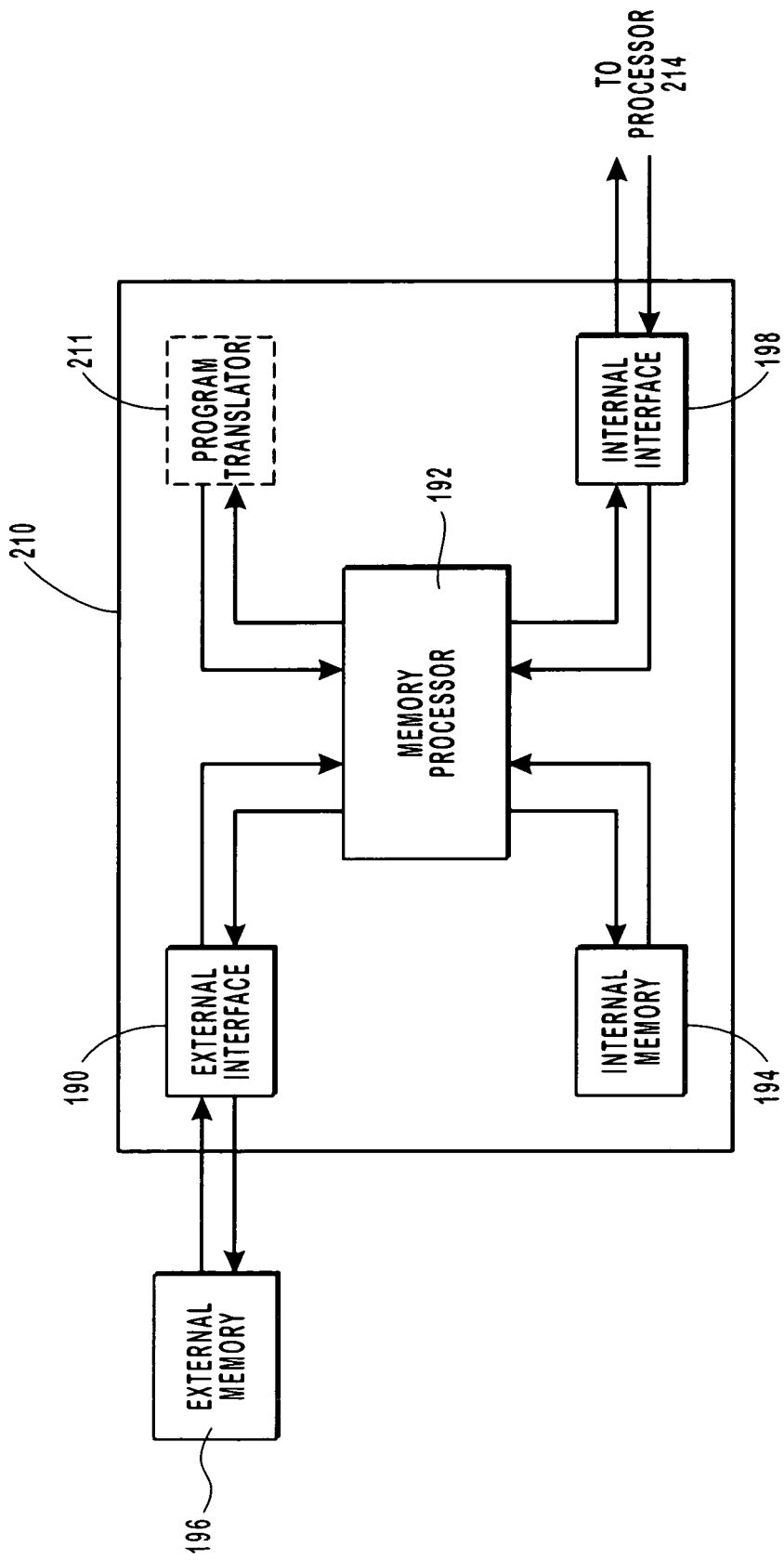
FIG. 8 is a schematic block diagram of an exemplary communication module of the exercise system of FIG. 1.

Now referring to FIG. 8, a more detailed view of communication interface 210 is illustrated. For simplicity, only the most relevant components and modules are illustrated in FIG. 8. It may be appreciated by one skilled in the art that various other components and modules may be included within communication interface 210 depending on the particular use and function of communication interface 210. Further, not all of the components or features of function of communication interface 210 may be used in each configuration. In addition, the features and functions of communication interface 210, whether wholly or partially, can be incorporated into processors 214, 220 or other portions of control panel 22 or treadmill controller 56.

As depicted, communication interface 210 can include a memory processor 192 that communicates with an external interface 190 and an internal interface 198. External interface 190 is configured to facilitate transmission and reception of one or more signals to and from external memory 196 and treadmill 12. Such signals may include exercise programs (including control signals, computer executable control signal instructions, audio and visual data, motivational content, etc.) the status and/or measurable parameters of the exercise device, information about the user, and the like. External interface 190 may be an input device and include, for example, a data port (e.g. stored data port 103), magnetic disc drive, optical disc drive, USB or Firewire ports or connections, software for other modules or accessing external storage devices, and the like. Internal interface 198 enables communication interface 210 to transmit the above signals and data to and receive various signals from treadmill 12 via processor 214 and/or control signal decoder 224 (FIG. 7). Such received signals may include measurable parameters of the user and/or exercise device, personalized user data, workout histories, exercise programs, and the like. Alternatively, external memory device 196 may receive no signals such as where communication interface 210 merely receives or reads data from external memory device 196 without saving or writing any data to memory device 196.

Each interface 190, 198 therefore, may be of a variety of types depending on the external memory device 196, processor 214, decoder 224, particular communication lines used in system 10 and the particular access and transmission protocols used by treadmill 12 and external memory 196. For example, as noted previously, interfaces 190, 198 may be a variety of ports or may be hardwired connections, software modules, computer executable instructions, or wireless interfaces using infrared (IR), radio frequency (RF), microwave technology, satellite, blue tooth transmission, home network protocols, or various other protocols and technology as known by one skilled in the art. Interfaces 190, 198 either solely or in combination with the other elements of communication system 18, may use various transmission protocols to transfer data between treadmill 12 and external memory 196 via communication interface 210. It may be appreciated by one skilled in the art that interfaces 190, 198 need not be the same, so long as they facilitate communication between the elements of treadmill 12 and external memory 196, communication system 18, and/or personal computer 14.

In the illustrated example, communicating with external interface 190 and internal interface 198 is a memory processor 192. Memory processor 192 can be used, in one embodiment, to configure external interface 190 to access external memory 196. Memory processor 192 may also be configured to transfer signals to processor 214 through internal interface 198 and thereby manipulate treadmill 12 based on programming selected by the user. In particular, memory processor 192, optionally in combination with interface 190 and/or 198, prepares the selected programming (e.g., exercise programs (including control signals, control signal instructions, and motivational content), user data, and/or any audio or visual signals, if any) for transmission to processor 214 or other components or elements of treadmill 12. Memory processor 192 also may "packetize" the programming it receives through external interface 190.

Generally, memory processor 192 may include one or more micro-controllers, central processing units, state machines, programmable logic arrays, network logical arrays, or gates, ASIC processors, software-based controllers, combination logic, combinations thereof, and a variety of other controllers known by one skilled in the art to manipulate data transmitted between treadmill 12, and external memory 196. Thus, memory processor 192 is one example of a structure capable of performing the function of means for transmitting control signals, control signal instructions, motivational content, and/ or other associated programming to the user device. It may be appreciated that various other control processors and means are appropriate and known to those skilled in the art.

Optionally communicating with memory processor 192 is an internal memory 194. Internal memory 194 may store programming transmitted between treadmill 12 and external memory 196. Accordingly, internal memory 194 may be one structure capable of performing the function of storage means for storing programming. Alternatively, or in addition thereto, internal memory 194 may store protocols for accessing any of various types of external memory devices 196 of various external memory formats. Accordingly, internal memory 194 may, therefore, include protocols such that interface 190 can access one or more one or more magnetic, optical, or flash memory devices (e.g. audiocassette, CD, mini disk, computer diskette, videotape, DVD, laser disk, USB or Firewire storage device, removable memory cards, etc.) which follow one or more formats or standards. For example, internal memory 194 may store protocols such that interface 190 can be configured to access CDs having CD-ROM, CD-R, and/or CD-RW formats. Alternatively, or in addition thereto, external interface 190 may be configurable to access external CD and DVD storage media. In still another alternative, internal memory 194 may store protocols such that external interface 190 can access multiple formats of removable memory cards, including, for example but not limitation, cards following Secure Digital and DataFlash standards.

In addition, internal memory 194 may store a particular set of control signals optionally in synchronization with an exercise program or motivational content. In light of the teaching contained herein, it may be appreciated by one skilled in the art, that internal memory 194 may also take the form of or include a database structure that enables access to the various programming stored therein. Similarly, it may be appreciated that internal memory 194 may be integral with, or replaced by memory 222 (FIG. 7) of treadmill 12, or incorporated into other components of communication interface 210, control panel 22, or treadmill controller 56.

Accordingly, by using protocols stored in internal memory 194, memory processor 192 is enabled to configure external interface 190 to access external memory 196. As noted earlier, external memory 196 may store one or more exercise programs for delivery to a user of treadmill 12. An exercise program may include, for example, control signals to manipulate speed, incline, or other operating parameters of treadmill 12, or may contain instructions for generating control signals, and which instructions may be executed by a separate module within external memory 196 or treadmill 12. An exercise program may further include motivational content which may or may not be synchronized with control signals and/or operating parameters of treadmill 12.

In one embodiment, memory processor 192 accesses external memory 196 for delivery of an exercise program to a user of treadmill 12. Memory processor 192 reads a control signal instruction stored in external memory 196 and generates a control signal corresponding to the read instruction. In another embodiment, memory processor 192 saves the exercise program, including any control signals or control signal instructions in internal memory 194. In still another embodiment, communication interface 210 includes an optional program translator 211 which communicates with memory processor 192. Program translator 211 may communicate with internal memory 194 or memory processor 192 and generate one or more control signals corresponding to a control signal instruction obtained from external memory 196. Accordingly, memory processor 192 and program translator 211 may be considered structures capable of performing the function of means for generating one or more control signals.

As may be appreciated by those of ordinary skill in the art, one or more of the functions of communication interface 210, such as but not limited to, program translation, including control signal generation, may be performed by processor 214, treadmill processor 220, program translator 211, or an exercise program or module stored in external memory 196 or internal memory 194. Accordingly, each of external memory 196, internal memory 194, processors 214 and 220, and program translator 211 may be considered structures capable of performing the function of means for generating one or more control signals.

Any program translator or means for generating one or more control signals may include circuitry and/or software to generate the control signals for a selected exercise program and which are optionally synchronized with audio, video, or motivational content retrieved from memory 194, 196, or 222. Therefore, means for generating control signals may include one or more micro-controllers, central processing units, state machines, programmable logic arrays, network logical arrays, or gates, ASIC processors, software-based controllers, combination logic, combinations thereof, and a variety of other controllers known by one skilled in the art to generate one or more control signals. One skilled in the art may identify various other configurations of means for generating one or more control signals, including, but not limited to, stand-alone or self-executable software modules.

Various configurations are applicable for generating, encoding, and decoding a control signal, either with or without audio, video, or motivational content. It will be appreciated that a variety of encoding methods are contemplated and within the scope of the present invention, and that the present invention should not be limited to any particular method or format for encoding. In particular, a number of encoding schemes are known to those skilled in the art and may be used to carry out the desired function and are encompassed within the scope of the present invention.

For example, at least two suitable methods are described in U.S. patent application Ser. No. 09/776,410, which is incorporated herein in its entirety, in which an audible control signal is encoded on a two (2) kHz carrier wave or in which a suitable control signal can be encoded in a border of a video signal. In such an embodiment, a control signal may use an RS-232 protocol. However, as will be appreciated, alternative control signals may be used in any of a variety of protocols. For instance, in one embodiment, the control signals follow a serial protocol such as serial peripheral interface (SPI). In still other embodiments, other protocols such as RS-422, RS-423, USB, or various other communication protocols known by one skilled in the art in light of the teachings contained herein, including both serial and parallel protocols, may be used.

Regardless of which control signal format is desired, the control signal is received and detected by treadmill 12, which verifies the control signal has a proper format and optionally checks for errors. If the signal is approved, the signal is delivered to the appropriate controllers for varying the operating parameters of treadmill 12.

To more easily explain the function and structures of system 10 and external memory 196, reference will now be made to FIG. 9 that is a schematic block diagram illustrating one embodiment of a portable data storage device 250 for use with treadmill 12. As will be appreciated, portable data storage device 250 may be similar to memory card 13 and external memory 196. Accordingly, the discussion with regard to portable data storage device 250 may be applied equally to memory card 13 and external memory 196.

Storage device 250 can include motivational content 258 and one or more exercise programs 252a, 252b. In the illustrated embodiment, each of exercise programs 252a, 252b, may further include exercise profiles 254a, 254b and program definitions 256a, 256b. In this embodiment, program definitions 256a, 256b, are representative of workouts which may be delivered to a user of treadmill 12. As described earlier, such definitions may, therefore, be executable modules which generate and send control signals to treadmill 12, or may be computer-executable instructions for generating control signals, and that are executed by treadmill 12 such that treadmill 12 generates any corresponding control signals. Accordingly, program definitions 256a, 256b, may generate one or more control signals to manipulate operating parameters of treadmill 12, or may provide instructions such that control panel 22 or treadmill controller 56 may generate control signals. Thus, exercise programs 252a, 252b, program definitions 256a, 256b, control panel 22, and treadmill controller 56, individually and collectively, may properly be regarded as means for generating one or more control signals for controlling operating parameters of treadmill 12.

As noted, program definitions 256a, 256b include control signals or control signal instructions such that control signals may be generated for controlling operating parameters of treadmill 12. In one embodiment, program definitions 256a, 256b further define segments of an exercise program to be delivered to treadmill 12. As used herein, the term segment is broadly used to describe a subset of an exercise program for delivery to a user in which one or more controllable operating parameters remain constant. Accordingly, a portion of an exercise program in which speed and incline are defined as remaining constant is properly viewed as a segment. Further, a portion of an exercise program in which only speed remains constant or in which only incline remains constant may similarly be viewed as a segment.

As illustrated, workout segments may be defined in program definitions 256a, 256b in any of a variety of manners. For instance, two exemplary segment formats are illustrated. In program definition 256a, for example, multiple segments are defined by expressly defining each segment of an exercise program (e.g. segments 1-*n*). For instance, each segment may be defined by specifying a segment interval or duration and the control signals appropriate for the operating parameters of treadmill 12 during the interval. For instance, a segment may set an interval of two minutes, and specify that at the start of the interval, the treadmill speed should be set to 3 mph while incline is set to seven degrees. Thereafter, during the specified interval, no control signals are sent to change the operating parameters. Accordingly, as treadmill 12 accesses and delivers exercise program 256a to a user, the operating parameters of treadmill 12 remain constant for the specified segment interval, after which a subsequent segment begins by setting different operating parameters and an interval for maintaining those operating parameters.

Similarly, program definition 256b defines multiple program segments and implicitly defines the segment intervals. In this embodiment, for example, program definition 256b expressly specifies times during the delivery of exercise program 252b at which control signals should be transmitted to or generated by treadmill 12, rather than intervals during which operating parameters are to be held constant. Accordingly, the time between such control signals is properly viewed a program segment. For example, in the illustrated embodiment, if control signals are sent at "Time 2" to change the speed and incline of treadmill 12, the time-period between "Time 1" and "Time 2" may be properly viewed as a segment of exercise program 252b inasmuch as the incline and speed remain unchanged during that period. Similarly, if the incline of treadmill 12 is changed at "Time 3", the period between "Time 2" and "Time 3" may also be viewed as a program segment inasmuch as the speed and incline are unchanged during that time. Notably, if only incline is changed at "Time 3" a segment beginning at "Time 2" and extending past "Time 3" is defined inasmuch as the operating parameter defining the speed of treadmill 12 is not changed during that time. Accordingly, it is not necessary that segments be separated and sequential, as program segments may also overlap.

In addition to control signals or control signal instructions, program definitions 256a, 256b of exercise programs 252a, 252b may further include data representative of motivational content. In one embodiment, motivational content is embedded within program definitions 256a, 256b. Accordingly, at specified times during exercise programs 252a, 252b, or at the beginning or end of segments, the motivational content may be transmitted to treadmill 12 to be played or displayed to the user. As noted previously, motivational content may include audio or visual information and, accordingly, motivational content may be provided to the user of treadmill 12 by speaker 96 and/or visual display device 94.

In an alternative embodiment, motivational content is stored separate from program definitions 256a, 256b and/or exercise programs 252a, 252b. For example, program definitions 256a, 256b may include a tag which references separately stored motivational content, such as the motivational content stored in motivational content library 258, and is indicative that the separate content should be played at a specified time or segment. In one embodiment, for example, the tag is a function call. In this description and in the claims, a "function call" is defined as a request for service from one module to another, whether it be automatic as a result of the operation of calling the module, or whether the call is in response to user input at treadmill 12. In the illustrated embodiment, for example, a tag to motivational content operates as a function call. The function call may, for example, request a specified motivational content file (MCF) for delivery to treadmill 12, and/or may further request that audio or visual display services within treadmill 12 be associated with the referenced motivational content file.

In one embodiment, motivational content is stored separately within motivational content library 258 on portable data storage device 250. Accordingly, when an exercise program is being performed and delivered to a user of an exercise device and a content tag is encountered, the referenced motivational content may be found and retrieved from motivational content library 258. In one embodiment, for instance, program definitions 256a, 256b are executables and may retrieve and send the content to treadmill 12. In another embodiment, program definitions 252a, 252b are computer-executable instructions executed by treadmill 12 and treadmill 12 accesses and retrieves the tagged content file from motivational content library 258.

As is further illustrated, motivational content library 258 may have one or more content categories 260a-c. Content categories 260a-c may be set up to correspond to a variety of user preferences, exercise programs, and the like. For example, in one embodiment, categories 260a-c may have audio motivational content having a pre-recorded personal trainer or third party providing encouragement or motivation to the user. Accordingly, in one embodiment, categories 260a-c contain similar content files, but have files corresponding to different voices, languages, or preferences of a user. For example, in one embodiment, an English-speaking user may request motivational content from a female voice. Accordingly, when an exercise program is delivered and a tag presented or function call made, the exercise program or device may search for an appropriate category (e.g. category 260b) and deliver content files within that category. Similarly, a Spanish-speaking user preferring a male voice may receive files from category 260c.

It may be appreciated by those of ordinary skill in the art, however, that the foregoing categories are illustrative only, and are not to be considered limiting of the present invention. Alternative content categories are considered which correspond to, for example, visual and music preferences. In addition, it is not necessary that each content category have similar content, and each content category may have different content files. For example, a content category within motivational content library 258 may include all of the content files corresponding to an exercise program (e.g. exercise programs 252a, 252b). Accordingly, content categories may be defined based on available exercise programs. In light of the teaching contained herein, it may be appreciated by one skilled in the art, that motivational content library 258 may take the form of or include a database structure that enables access to the various content categories, files, or other programming stored therein.

It may be also appreciated that the storing of motivational content, including any audio or visual content, whether stored within exercise programs 252a, 252b or within motivational content library 258, generally increases the necessary storage capacity of portable data storage device 250 as compared with a similar device not having similar motivational content. In other words, an exercise program with motivational content requires more free storage space than the same program stripped of such content. For example, in an exercise program having motivational content embedded therein, the motivational content may contribute to more than ninety percent of the size of the exercise program. Accordingly, one feature of exercise programs 252a, 252b which merely contain tags to content files stored within content library 258 is the reduced size of exercise programs 252a, 252b. In particular, exercise programs 252a, 252b can achieve a space savings on the order of ninety percent or more as compared to exercise programs having embedded motivational content, inasmuch as no motivational content is directly stored therein.

While inserting tags to content files in independent content library 258 may be viewed as merely shifting the size of exercise programs 252a, 252b to motivational content library 258, in the present invention, content library 258 is further configured to reduce the storage capacity necessary to run a stored exercise program. In other words, the combined size of an exercise program and its associated content files within motivational content library 258 is less than the size of the same exercise program having motivational content embedded at each instance therein.

In one embodiment, for example, exercise programs 252a, 252b are created with content tags such that a single motivational content file within content library 258 is called multiple times during delivery of the program. For instance, in the simplified embodiment illustrated in FIG. 9, "MCF A" has an "Up" attribute. This may indicate that the motivational content includes an indication to the user that a hill is being simulated or the difficulty is being increased. Accordingly, at the beginning of any segment in which the incline increases over that of the previous segment, program definitions 252a, 252b may include a tag to MCF A. Similarly, "MCF D" has a "Slow" attribute. This may indicate that the motivational content may be played when a segment changes and the speed of treadmill 12 is reduced, such that at any segment where speed decreases, program definitions 252a, 252b may call MCF D. In this manner, motivational content may be repeated multiple times during an exercise program, while program size is reduced by storing the content only a single time. Accordingly, storage space on portable data storage device 250 is conserved.

As may be appreciated, space conservation can be achieved by storing motivational content files specific to an exercise program within the program, rather than within content library 258. Accordingly, it is not necessary that content files be stored independent of an exercise program to achieve the file size reduction contemplated in this invention. For instance, content files may be stored in a library or a database structure within an exercise program but independent of the program definition. Nevertheless, it will also be appreciated that a single content file may be referenced by multiple exercise programs such that an additional savings can be made by storing content files within a centralized content library 258, as described.

As indicated previously, motivational content, including the motivational content files within content library 258, may thus correspond to the operating parameters and/or exercise program segments. For example, as noted above, motivational content indicating a change in speed or incline may be called before or at the same time that control signals are generated to change the incline or speed. Accordingly, motivational content may be synchronized with control signals and/or changes in operating parameters of treadmill 12.

It will also be appreciated, however, that the present invention contemplates motivational content which corresponds to operating parameters and/or program segments but which do not correspond to, and are not synchronized with control signals or changes in operating parameters. For example, content library 258 includes motivational content file "MCF N" which, in this embodiment, has a "Sustain" attribute. The "Sustain" attribute may, for example, correspond to audio content encouraging a user in the middle of a particularly difficult or long program segment. Thus, program definitions 256a, 256b, may insert a tag calling MCF N during a segment or at a specific time during the selected exercise program, such that the content is provided in the middle of a program segment, without any corresponding change in operating parameters. In this manner, motivational content may be correspond to operating parameters of treadmill 12 while not being synchronized with a change in those operating parameters.

Figure 9:
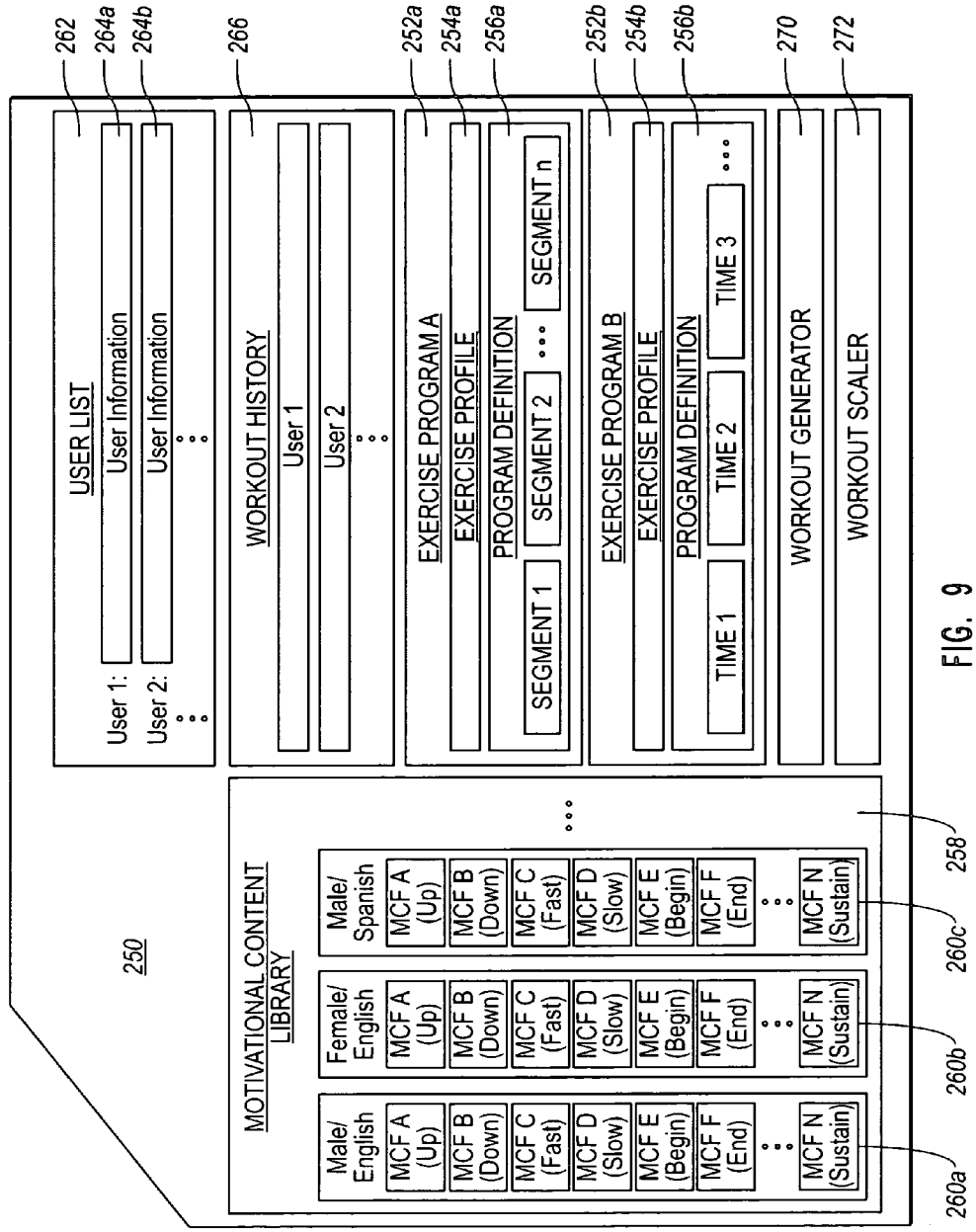
FIG. 9 is a schematic block diagram of the exemplary portable storage device illustrated in FIG. 1.

With continued reference to FIG. 9, and as noted previously, exercise programs 252a, 252b optionally include exercise profiles 254a, 254b representative of the workout. These exercise profiles 254a, 254b may be programming which includes information describing the exercise program, such as a summary of some operating parameters or other aspects of the corresponding exercise program. Such programming may, for example, identify an intensity level of exercise program 252a, 252b or other information to assist a user in selecting which exercise program to use.

For example, information within exercise profiles 254a, 254b may include, a name or other identifier of the corresponding exercise program. Similarly, exercise profiles 254a, 254b may describe the duration, distance, elevation climb, type of program, estimated calories to be burned, or recommended user fitness level of the corresponding exercise program. Additionally, or in the alternative, maximum, minimum, or average operating parameters (e.g. speed, incline, resistance, etc.) during the workout may be identified or represented. In some embodiments, and as described in more detail hereafter, exercise profiles 254a, 254b further include graphical or other visual representations which may be displayed to the user, while in other embodiments, processors 192, 214, 224, program translator 211, or other modules or components of treadmill 12 or portable data storage device 250 may interpret the data provided by exercise profiles 254a, 254b and generate a graphical or visual information for display to the user of treadmill 12.

As further illustrated in FIG. 9, portable data storage device 250 may further include a variety of other modules. For example, such modules may include a user list module 262 which identifies one or more users authorized to access modules on storage device 250, treadmill 12, and/or personalized information 264a, 264b information representative of the identified users.

Optionally, storage device 250 further includes a workout history module 266 which saves information corresponding to one or more exercise programs performed by a user. For simplicity, workout history 266 is illustrated independent of user list 262. As may be appreciated in light of the teachings herein, however, workout history 266 contains information which is personal to individual users and thus may be contained within personalized information 264a, 264b, or stored separately.

Additional modules which are optionally included on storage device 250 include, for example, workout generator module 270 and workout scaling module 272. Workout generator 270, for example, may include one or more algorithms or constructs usable for building custom workouts in response to a request by a user of treadmill 12. For example, a user may enter one or more desired operating parameters of treadmill 12 (e.g. minimum, maximum, or average speed or incline), or other types of information such as found in exercise profiles 254a, 254b (e.g. duration, distance, elevation climb, intensity level, program type, etc.). Using the algorithms or constructs, workout generator 270 may build an exercise program and/or exercise profile for delivery to treadmill 12. Further, using attributes associated with motivational content files (e.g. up, down, fast, slow, begin, end, sustain, etc.), workout generator 270 may further incorporate tags within the created exercise program such that appropriate motivational content is included within the exercise program and can be provided to a user. As may be appreciated, once a program is built, it may be stored either permanently or temporarily on storage device 250 or treadmill 12.

Workout scaling module 272 may similarly operate to modify one or more stored workout programs. For example, before selecting an exercise program, or while using a program, a user may find that the difficulty, distance, speed, incline, duration, etc. are more or less than desired. Accordingly, in one embodiment of the present invention, scaling module 272 includes any suitable algorithm to allow the user to scale or otherwise modify the selected exercise program. Scaling module 272 may, for example, intercept control signals and/or tags as they are received from an exercise program. Thereafter, scaling module 272 may scale control signals according to one or more scaling values associated with input received from the user of the exercise program such that operating parameters of treadmill 12 are scaled. Similarly, scaling module 272 can review content tags and determine if they are appropriate for the scaled operating parameters of treadmill 12. If appropriate, they may be played, whereas inappropriate motivational content may be ignored or replaced with more appropriate motivational content. In another embodiment, scaling module 272 acts as a cache or buffer of a selected exercise program, and modifies the full exercise program according to user input, rather than modifying the program during operation (e.g. by intercepting signals). In yet another embodiment, memory processor 192 (FIG. 8) may receive control signal instructions and/or tags from a selected exercise program and request scaled control signals and tags from workout scaling module 272. Accordingly, in light of the teachings herein, it may be appreciated that scaling module 272 may be located on portable data storage device 250, in control panel 22 (FIG. 1), or otherwise in treadmill 12 (FIG. 1). Accordingly, inasmuch as scaling module 272 modifies an exercise program and a new program is generated, scaling module 272 may also be properly considered a workout generator.

Referring now to FIGS. 1 and 10-17, an exemplary process 300 is illustrated in which treadmill 12 accesses memory card 13. As noted previously, treadmill 12 may be configured with protocols to access any of a variety of memory card formats, and such protocols may allow treadmill to read (i.e. one-way) and optionally write (i.e. two-way) to memory card 13. Thus, a process for accessing memory card 13 may also include acts of writing information to memory card 13. Inasmuch as treadmill 12 may be configured for only read-access to memory card 13, it will be appreciated, however, that any acts of writing to memory card 13 are optional.

In accessing memory card 13, whether by reading or writing to the card, a variety of information may be accessed and/or transferred. For instance, such information may include exercise programs (including control signals, program definitions, control signal instructions, profile data, etc.), motivational content, personalized user information, workout histories, and the like. Additionally, while the following description specifically describes the process with portable memory card 13, it may be appreciated that such a description is equally applicable to interactions between treadmill 12 and portable data storage device 250 (FIG. 9) or external memory 196 (FIG. 7).

Figure 10:
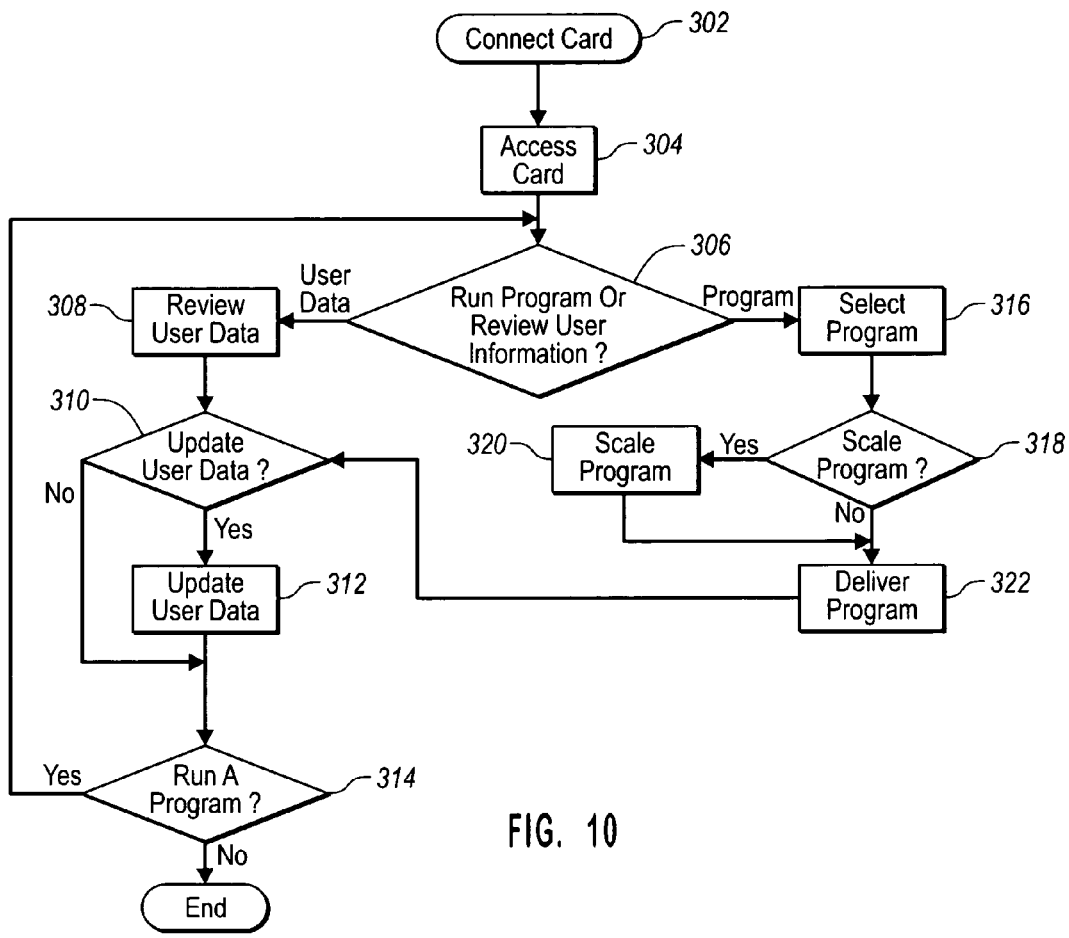
FIG. 10 is a flow diagram illustrative of the process of delivering a workout stored on the portable data storage device of FIG. 1.

With reference now to FIG. 10 and FIG. 1, a flow diagram illustrating a broad operation of system 10 according to one embodiment of the present invention is illustrated. Initially, treadmill 12 is connected to memory card 13, as represented by block 302. For example, memory card 13 may be directly inserted into an input device of treadmill 12. For instance, a user may insert memory card 13 into stored data port 103 (FIG. 6) which is configured to receive and accept memory card 13. Optionally, a storage device sensor (not shown) may detect when memory card 13 is inserted in stored data port 103 (FIG. 6) and notify treadmill 12 of the presence of memory card 13, such that a connection may be established. Alternatively, memory card 13 and treadmill 12 may each be connected to personal computer 14 and/or communication system 18, such that treadmill 12 may be indirectly connected to memory card 13 via computer 14 or communication system 18.

Upon connecting memory card 13 to treadmill 12, treadmill 12 may access memory card 13, as represented by block 304. As noted previously, access of memory card 13 may, for example, be one-way access in which treadmill 12 reads and receives information from treadmill 12, but is not enabled to write to memory card 13. In another embodiment, access may be bi-directional such that by accessing memory card 13, treadmill 12 is able to transfer and receive (i.e. transceive) data to and from the various modules, components, and other hardware and/or software modules of memory card 13.

Figure 11:
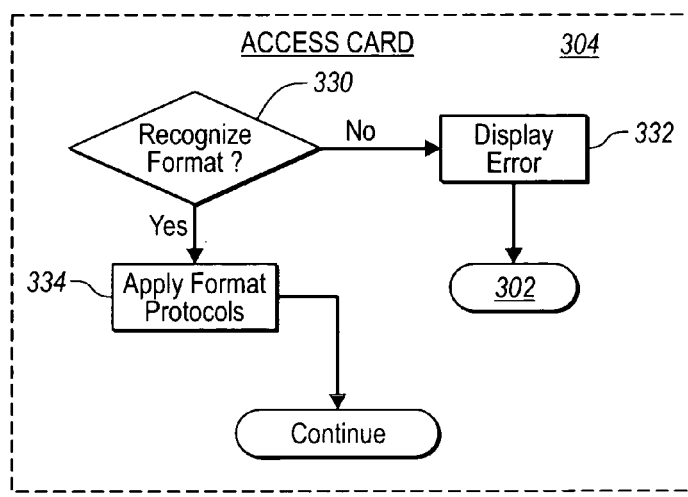
FIG. 11 is a flow diagram illustrative of the process of accessing the portable data storage device of FIG. 1.

An exemplary embodiment of accessing memory card 13 is illustrated in more detail in FIG. 11. As depicted by decision block 330, when memory card 13 is inserted, treadmill 12 initially determines whether the structure, format, or standard of memory card 13 is recognized. Treadmill 12 can be configured to accept multiple formats of memory card 13 inserted into stored data port 103 (FIG. 6). For example, protocols for recognized formats may be stored in memory 194, 222 (FIGS. 7 and 8) and may be accessed when a card of a corresponding format is recognized. Available protocols may include, for example, access protocols to both read and write to the card. Alternatively access protocols may be limited to protocols allowing treadmill 12 to read memory card 13, such that write-access to memory card 13 is blocked or inhibited. In still another alternative, protocols for one format may be for both read and write access, while protocols for another card may be for only read access.

The various access protocols may be stored on, or otherwise accessible to treadmill 12. For instance, protocols may be stored directly on treadmill 12 such as, for example, in memory 194, 222. Alternatively, access protocols may be stored in or otherwise accessible through computer 14 or communication system 18. To determine whether the format of memory card 13 is recognized, processor 192, 214, or 220 may, for example, query a data structure storing the access protocols and match the stored protocols with those needed to access memory card 13.

While a treadmill 12 may have only a single set of accessible protocols, such that only a single format of memory card 13 may be accessed by treadmill 12, it is preferable that multiple formats be recognized. It may be appreciated, therefore, that treadmill 12 can have access to protocols for multiple standards used with memory card 13, such that a single input device such as stored data port 103 may be configured to connect to, and enable access of, a variety of card formats through the single interface.

For instance, in one embodiment, memory card 13 conforms to the Secure Digital (SD) standard. Secure Digital is a flash based removable memory card which may be used for standard or extended data storage. Commonly, SD cards are used as memory devices for handheld devices such as cameras, audio players, personal digital assistants (PDA), and the like. SD cards are desirable for such portable devices because they store large amounts of data (e.g. between 36 MB and 1 GB of data) while being dimensionally small (dimensions of 32 mm×24 mm). Accordingly, SD cards can be easily transported and allow high portability of a large amount of storage capacity.

At least in part due to the popularity of SD cards with handheld devices, personal computers are also being made to include SD ports for accessing SD cards removed from such portable devices, including the data stored on the SD card. Accordingly an SD card may be accessible by a variety of devices which may each have read and optionally write access to the card so as to read and store any of a variety of types of data and information. Where memory card 13 conforms to the SD standard, many of the same features that make SD cards popular with handheld devices and computers may also be obtained with respect to its use with treadmill 12. For example, because SD cards can hold large quantities of data, memory card 13 may include many different exercise programs, or individual exercise programs may be larger and include, for example, music or video content. As will be appreciated, because of the wide usage of SD cards with portable devices, an SD card according to the present invention may simultaneously store exercise data such as exercise programs 252a, 252b (FIG. 9), user information 264a, 264b, workout history 264, motivational content, and the like, as well as non-exercise data (e.g. photographs, word processing documents, etc.).

In addition, because SD cards are widely used, such a card may be accessible to a user through the user's computer. Accordingly, if a user wants to run an exercise program on treadmill 12, the user may create an exercise program on computer 14, or may download an exercise program over network 16 (such as from communication system 18 or third party 21) and transfer the program to memory card 13. Thereafter, memory card 13 may be removed from computer 14 and connected to treadmill 12. In this manner, treadmill 12 may then access the stored exercise program and deliver the program, including any control signals and motivational content, to the exercise device.

As may be appreciated by a person having ordinary skill in the art, in light of the teachings herein, other advantages may also be obtained by enabling treadmill 12 to access an SD card. For example, because SD cards are widely used for various portable devices, a user may have one or more SD cards on hand and will be able to use an available card without the need to purchase a new or additional storage device. Similarly, because an SD card may be accessed by a personal computer, exercise programs, user information, motivational content, and the like may be stored on computer 14 until a user wishes to run a desired exercise program exercise program. In this manner, storage space on memory card 13 can be conserved by storing only recently used or to be used programs on memory card 13.

In addition, another feature of using an SD card, or other flash memory cards, is that a communication port such as stored data port 103 (FIG. 6) may have few or no moving parts. Accordingly, the movement or vibrations of treadmill 12 are of more limited effect on stored data port 103 (FIG. 6) such that the ease of accessing memory card 13 is increased.

While memory card 13 of an SD format may be desirable for some users of treadmill 12, such a format may be prohibitive for other users. For example, a user may not have a handheld or other device using an SD card, such that such a card is not immediately available. Accordingly, the user may not have access to an SD card to use for accessing stored workout programs. Moreover, because SD cards generally have large storage capacities, the cost of such a card may be cost prohibitive to a user who merely wishes to use the card for workouts, particularly where such workouts have small file sizes. For instance, a user may desire to obtain an exercise program from third party 21 or communication system 18. If only a single exercise program is requested, the capacity necessary for the provider to store the exercise program and any personalized user information may be much less than the actual capacity of the SD card. Accordingly, the user pays for a card of which a majority of the storage capacity may be unused.

Accordingly, in one embodiment, treadmill 12 is configured to access cards of various formats and having varying storage capacities. For instance, in one embodiment, treadmill 12 is configured to access memory cards having an SD format as well as a MultiMedia Card (MMC) flash memory format. For example, in one embodiment, memory card 13 may be a card having a DataFlash format which is form factor compatible with the MMC format.

Using a DataFlash card with treadmill 12 may include various features which may not available with an SD card. For example, DataFlash cards are available in significantly smaller storage capacities (e.g. 2, 4 and 8 MB). Accordingly, a user may realize a significant cost savings by using a DataFlash card as compared to an SD card as it is possible to purchase much less storage capacity. Notably, and as discussed previously, in one aspect of the present invention, tags (e.g. function calls) are included in exercise programs 252a, 252b (FIG. 9), and reference independently stored motivational content files. Accordingly, when such programs are stored on a DataFlash card, a significant savings can be realized by a user inasmuch as the reduced size of an exercise program allows cards with less storage space, and thus less expense, to be used with the present invention.

In addition, because SD cards may be accessed by a user or third party on a computer, exercise programs, motivational content, personal data and the like is susceptible to being moved and/or deleted from the computer and card. Because information can be deleted from the card, this increases the likelihood that a user will inadvertently misplace or delete desired information. Consequently, when the user desires to access the misplaced or deleted information, a user may have to re-purchase or re-create the information. Similarly, a user may inadvertently transfer all or a portion of an exercise program from the SD card to the computer. Consequently, when the user wants to run the exercise program, the user may find, for example, that motivational content has been removed and may need to postpone the program until the removed content can be restored. Inasmuch as the present invention may be used on home and commercial equipment, where a user takes advantage of exercise equipment at a commercial or other gym which is remote from the user's home, this may prevent the user from completing the exercise program inasmuch as the user may not have close access to the computer on which the remaining portions of the program are stored. In addition, even when using a device at home or otherwise situated near the computer with the information, a user may frequently have only a limited amount of time available for exercise. The delay caused by then finding and transferring the necessary data to memory card 13 before running an exercise program may decrease the amount of exercise in which the user may engage.

The use of DataFlash cards with the present invention does not suffer many of the drawbacks associated with SD cards. For example, largely because DataFlash cards have smaller storage capacities, DataFlash cards have not been widely used for removable and expandable storage, and are thus are not generally accessible with a general purpose computer. Thus, where memory card 13 has a DataFlash format, personal information, exercise programs, motivational content, and the like are not likely to be removed, misplaced or lost by a user. Similarly, because the access to DataFlash cards is restricted from a personal computer, there is a reduced likelihood that personal information will be inadvertently or intentionally altered or accessed. For example, a user may store personalized information 264a, 264b (FIG. 9) on memory card 13. For an SD card, if the card is inadvertently misplaced or lost, a third party finding memory card 13 may insert the card into a personal computer and thereafter retrieve and use the user's personal data. In contrast, access to DataFlash cards is more limited such that a third party may not have access to retrieve such information. Accordingly, the format of memory card 13 may be properly viewed as means for restricting access to information on memory card 13. Alternatively, information on memory card 13 may be encrypted. In still other alternatives, all or a portion of memory card may be read or write protected such that information cannot be accessed, removed, or replaced except by an authorized computer and/or compatible exercise device. Because of the different features available with SD and DataFlash cards, the present invention provides for storing the protocols for each format on treadmill 12, such that a user may take advantage of any or all available formats. Accordingly, in one embodiment of the present invention, a second stored data port (not shown) is added to control panel 22 such that a first stored data port 103 (FIG. 6) may receive cards of one format, while the second stored data port may receive cards of a second format.

Notably, while DataFlash cards have substantially less storage capacity than SD cards, the size of a DataFlash card is not similarly reduced. In particular, SD, MMC and DataFlash cards are approximately equal in size, and each measures approximately 32 millimeters in length by 24 millimeters in width. As a result, first stored data port 103 (FIG. 6) and a second stored data port may be substantially identical in appearance. In this manner, it may not be apparent to a user which port accesses which respective card format. Accordingly, the present invention also provides for a single stored data port 103 which can receive multiple card formats and avoids confusion over which of various ports may receive memory card 13.

It will be appreciated that stored data port 103 (FIG. 6) may, accordingly, be configured to receive a portable storage device having any of a variety of or following industry standard or proprietary formats. For instance, in one embodiment, a stored data port 103 is configured to receive one or more memory cards following industry standard formats. Examples of such cards include, flash memory cards and USB-enabled memory devices. For instance, by way of example and not limitation, specific industry standard formats contemplated herein include: SD, small form factor SD, MMC, small form factor MMC, DataFlash, CompactFlash, removable NAND-type flash memory (e.g. SmartMedia, Sony Memory Stick), one-time-programmable memory cards (OTP), XD cards, and the like.

Accordingly, it should be appreciated by one of ordinary skill in the art, particularly in light of the disclosure herein, that the present invention is not limited to memory cards or any specific type of memory card type and/or format. Thus, although the use of SD, MMC, and DataFlash cards are described herein in detail, a similar discussion may be had for a variety of other industry standard and/or proprietary formats.

Further, other memory cards may also be placed into a format which may be used in data port 103 with SD, MMC, DataFlash or other formats. For instance, an OTP card, in one implementation, can be produced to have the same shape and configuration as a standard SD or DataFlash card. Accordingly, an OTP card may be constructed to have pins positioned similar to an SD (9-pin) or Dataflash (7-pin) such that contacts within data port 103 may access the pins on the OTP card. In this manner, OTP card may also be accessed by an exercise device through data port 103. Notably, the 7-pin configuration of the DataFlash card can overlap the 9-pin configuration of an SD, such that the same contacts within data port 103 may be used to access any of the various types of memory cards inserted therein.

When memory card 13 is inserted into stored data port 103, treadmill 12 initially recognizes the format of memory card 13, retrieves protocols stored for the corresponding format of the card, and applies the appropriate protocols, as represented by blocks 330 and 334, such that memory card 13 can be accessed. In one embodiment, treadmill 12 determines the format of memory card 13 (decision block 330), by utilizing one or more public command sets.

For instance, in one embodiment, a public command set is stored in memory 222 or internal memory 194. Data port 103 is equipped with a switch or sensor linked to processor 192 and/or 214 so as to indicate when memory card 13 is received therein. When the sensor indicates the presence of memory card 13, or when a switch closes to indicate the card is installed, the step of determining the card type is initiated. Processor 192 or 214 may, for example, send a first public command set corresponding to a first card format (e.g. SD), which requests a response from the installed memory card 13. If a response is received by treadmill 12, then memory card 13 is known to follow the first format. If no response is received, a second public command set may be sent which corresponds to a second format (e.g. DataFlash), which makes a similar request of memory card 13. If a response is received, memory card is known to follow the second format. As will be appreciated, this process may be repeated for additional card formats (e.g. MMC, OTP, etc.) accessible by treadmill 12. Similarly, it may be appreciated that while the foregoing description describes a serial process in which public command sets are sent in sequence, such a process may occur in parallel. Namely, multiple public command sets may be sent to and request a response from memory card 13 at a single time (i.e. in parallel), and treadmill 12 can determine the format of memory card 13 by detecting the format of a received response.

If memory card 13 is of a format for which protocols are not available, treadmill 12 may not access the card and information saved on memory card 13 will not be available to the user via treadmill 12. Optionally, treadmill 12 may indicate to the user that the card is not recognized such as, for example, displaying an error message, as represented by block 332. Such an error message may be displayed, for example, by using an LED display (not shown) in or near stored data port 103 (FIG. 6). In one embodiment, the LED lights up in a first color (e.g. red), when such an error has occurred. In contrast, when a card format is recognized and memory card 13 is accessible to treadmill 12, the same or a second LED may light up in a second color (e.g. green). It will be appreciated that error messages may be displayed in a variety of other manners. For example, in other embodiments, an error message is displayed on visual output display 94 or an audible notice of the error is given to the user via speaker 96.

As noted previously, memory card 13 may include one or more exercise programs and/or personalized information for one or more users. Returning now to FIG. 10, it will be seen that in such a case, and as represented by decision block 306, after memory card 13 is accessed, it is optionally determined whether treadmill 12 should access the user information or an exercise program. Such a determination may be made, for example, by requesting input from a user. In particular, a prompt may be displayed on visual display device 94 (FIG. 6) or played over speaker 96 asking the user which step is desired. The user's response may then be provided, for example, through keypad 108, mouse 100, camera 92, microphone 90 (FIG. 6), by a touch-screen input on visual display device 94, or by any variety of other input devices. For instance, the user may select to access the user information, resulting in the process proceeding to review the user data, as represented by block 308. Alternatively, such as as when the user declines to access the user information, a prompt may be displayed on visual display device 94 (FIG. 6) or played over speaker 96 (FIG. 6) asking the user to select a program, as represented by decision block 316, and which will be described in more detail hereinafter.

Alternatively to prompting the user, treadmill 12 (FIG. 6) can automatically determine whether a program or user information is to be reviewed. For example, when memory card 13 is inserted and accessed, treadmill 12 may be configured such that it automatically updates based on user information on memory card 13. For instance, memory card 13 may conform to a standard for which treadmill 12 has only read access to card 13. In such a case, treadmill might automatically recognize the card format, read the user information from the card, and update memory 194, 222 (FIGS. 7 and 8) with the stored user information. Alternatively, treadmill 12 may automatically update either treadmill 12 or memory card 13 with the most recent user information. For example, processor 214 (FIG. 7) may instruct communication interface 210 (FIG. 7) to read user information from memory card 13 and transfer the information to processor 214. Thereafter, processor 214 may compare the user information on memory card 13 with user information stored in memory 194 or 222 (FIGS. 7 and 8). If the user information on memory card 13 does not match the user information stored in treadmill 12, or if there is no information on treadmill 12 corresponding to the user, treadmill 12 may automatically update memory 194 or 222 (FIGS. 7 and 8) with the updated information. For example, treadmill 12 may determine that the user information on memory card has been updated more recently than user information stored in treadmill 12. Accordingly, treadmill 12 may replace the user information stored therein with the information stored in memory card 13. Optionally, if treadmill 12 determines that user information in memory 194, 222 (FIGS. 7 and 8) is more current than information in memory card 13 (e.g. updated more recently), treadmill 13 may replace the user information on memory card 13 with the updated user information. Alternatively, upon finding different user information on memory card 13, treadmill 12 may prompt a user to update the information. Accordingly, and in this manner, treadmill 12 may automatically or manually be configured with the most recent user information.

Figure 12:
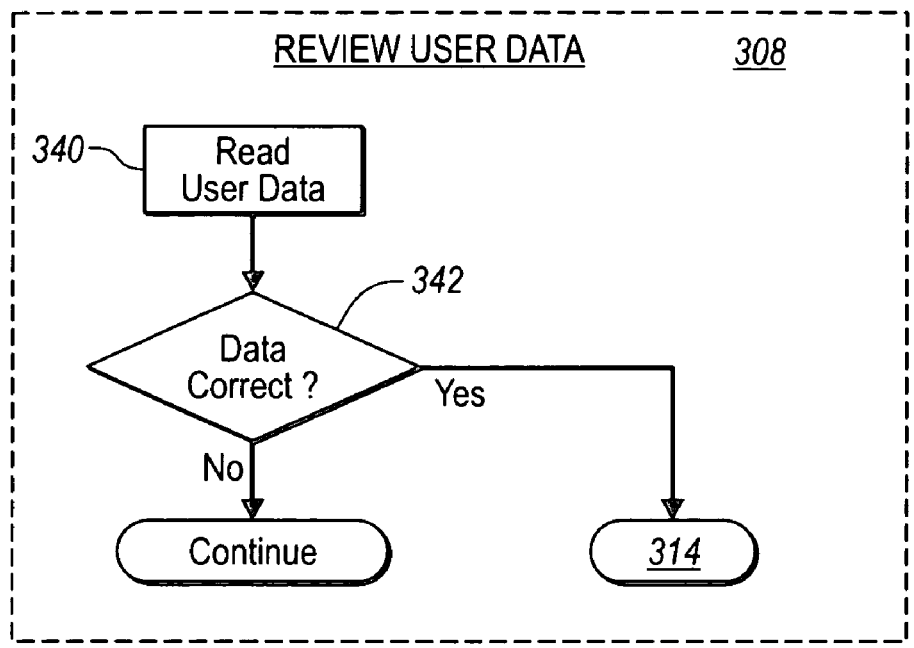
FIG. 12 is a flow diagram illustrative of the process of selecting a user to run an exercise program stored on the portable data storage device of FIG. 1.

Turning now to FIG. 12, illustrated is an exemplary process in which user information is reviewed, as represented by block 308, regardless of whether the determination to review the information is automatic or in response to user input. For example, in block 340, treadmill 12 accesses and retrieves the user information on memory card 13. Thereafter, a determination is made as to whether the user information stored on memory card 13 and/or treadmill 12 is correct, as represented by decision block 342. For instance, and as noted above, this may be done by comparing user information obtained from memory card 13 with that previously stored on treadmill 12. Alternatively, the user may be asked if he or she would like to review the user information and/or whether the information is correct.

If the user information is found to be correct or the user does not wish to update the information, decision block 342 is in the affirmative and the review of the user information may be ended and process 300 may proceed to decision block 314 (FIG. 10) to determine if an exercise program is to be run. If the information is not correct, decision block 342 is in the negative, and as illustrated in FIG. 10, it can then be determined whether the user information on treadmill 12 and/or memory card 13 should be updated, as represented by decision block 310. In one embodiment, the user determines whether to update by entering a decision in an input device 216 (FIG. 7). Alternatively, as noted above, treadmill 12 automatically makes the determination. If the information is not to be updated, process 300 proceeds to determine whether or not an exercise program is to be run, as represented by decision block 314. In contrast, if treadmill 12 determines that information should be updated, or if a user decides to update the information, any updated information may be obtained and thereafter updated, as represented by block 312.

Figure 13:
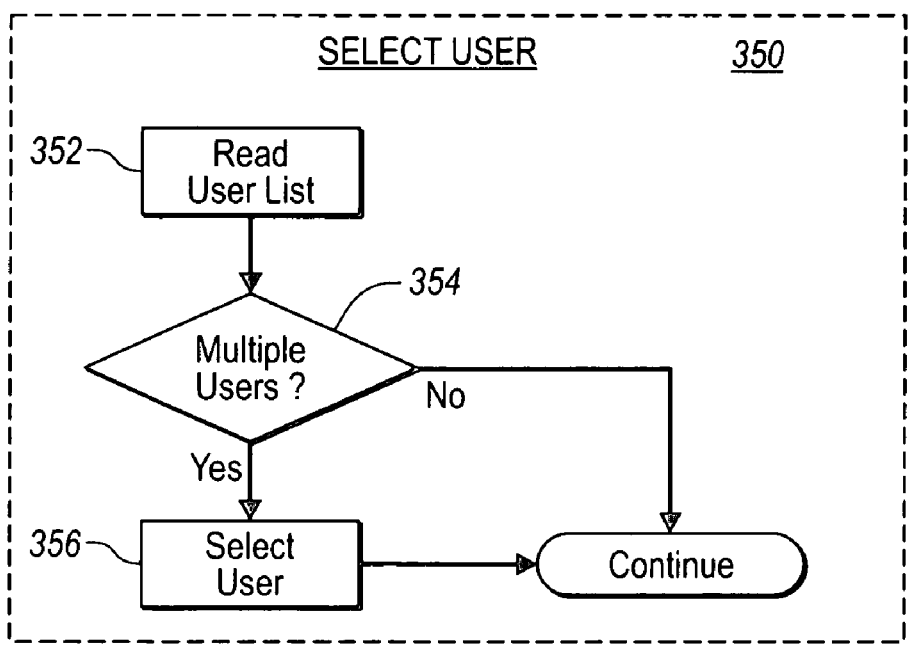
FIG. 13 is a flow diagram illustrative of the process of reviewing and updating user information used in delivering an exercise program on the system of FIG. 1.

As may be appreciated in light of the teachings herein, personalized user information 264a, 264b (FIG. 9) corresponding to one or more users of treadmill 12 is optionally stored on memory card 13. Accordingly, FIG. 13 illustrates an optional method of selecting a user from among multiple users with information saved on memory card 13, as represented by block 350. The process of selecting the appropriate user may occur, in one embodiment, before determining whether to review user information, as represented by decision block 306, or an exercise program, as represented by decision block 314. Accordingly, in such an embodiment, treadmill 12 may automatically, or in response to user input, then determine whether to review user information or run an exercise program.

In one embodiment, the process of selecting a user, as represented by block 350, can include treadmill 12 reading user list 262 on memory card 13, as represented by block 352. In one exemplary embodiment, processor 214 (FIG. 7) requests user list 262 (FIG. 9) which is provided by memory card 13 through communication interface 210 (FIG. 7). Upon accessing user list 262, communication interface 210 and/or processor 214 may make an initial determination of whether list 262 includes more than one user, as represented by decision block 354. If user list 262 includes a single user, then process 300 continues based upon the location within the process 300 that the process of selecting the user occurs. Alternatively, if list 262 includes multiple users, at least one of the users is selected, as represented by 356. In one embodiment, each user in user list 262 may be displayed to the user by using visual output device 94 (FIG. 7), and the user is allowed to select the appropriate user. In addition, or in the alternative, the user may be prompted for a user identification and/or password which, when input, can be matched with a user identification and password stored on memory card 13, such as in personalized information 264a, 264b (FIG. 9), before a user is successfully selected.

Referring again to FIG. 10, when it is determined that an exercise program should be run, decision block 314 being in the affirmative and so decision block 306 indicating that a program is to be run, an exercise program is selected, as represented by block 316. Selection of an exercise program may be either automatic or in response to user input. For example, upon determining that a user intends to run an exercise program, processors 192, 214 (FIGS. 7 and 8), may access memory card 13 through interface 190 (FIG. 8) and determine the exercise programs stored thereon. If only a single exercise program is stored on memory card 13, processor 192 or 214 (FIGS. 7 and 8) may automatically determine that the program is to be accessed and delivered to the user.

In another embodiment, memory card 13 stores user information for multiple users, and treadmill 12 has previously determined which user in user list 262 (FIG. 9) intends to run an exercise program. In such a case, processor 192 or 214 (FIGS. 7 and 8), via interface 190 (FIG. 8), may access memory card 13 and determine which stored workouts a user is authorized to use. In one example, each exercise program specifies which users are authorized to access the workout (e.g. in an exercise profile), or user information 264a, 264b (FIG. 9) is updated to include which programs are accessible to the user. Treadmill 12 may, therefore, determine exercise programs the selected user is authorized to run. Treadmill 12 may then automatically select a workout such as, for example, where the user is authorized to run only a single exercise program. Alternatively, an extended workout schedule may be stored on memory card 13, such that when memory card 13 is accessed by treadmill 12, treadmill 12 may automatically determine which exercise program is next scheduled in the extended workout schedule, and can automatically run the next scheduled workout. Optionally, user confirmation of the next scheduled workout may be requested.

In yet another embodiment, an exercise program is selected in response to input from the user. For example, FIG. 14 displays an exemplary process for selecting an exercise program, as represented by block 316, in response to user input. In this embodiment, treadmill 12 accesses the one or more exercise programs stored on memory card 13 in any previously described manner, as represented by block 370. As detailed earlier, each exercise program stored on memory card 13 (or each exercise program accessible to a selected user) may include an exercise profile 254a, 254b (FIG. 9) which includes information about a corresponding exercise program 252a, 252b (FIG. 9). To facilitate selection of an exercise by a user, exercise profiles 254a, 254b (FIG. 9) may then be read by treadmill 12. Exercise profile 254a, 254b (FIG. 9) may include a variety of information which may helpful in allowing a user to select a desired exercise program. Exemplary information which may be provided in the profile includes, but is not limited to: program name or other identifier, program type, fitness level, duration, distance, elevation climb, estimated calories burned, speed information, incline information, resistance information, graphical representation of the program, motivational content information, and the like.

In one embodiment, and as illustrated with reference to FIGS. 14 and 15, display of the profile data, as represented by block 372 is performed in a browser 390 displayed on visual output device 94 (FIG. 6). For example, in this embodiment, browser window 390 displays textual information 392a, 392b representative of a corresponding exercise program. In one embodiment, textual information 392a, 392b is obtained from an exercise profile saved in memory card 13. In another embodiment, processors 192, 214 (FIGS. 7 and 8) and/or program translator 211 (FIG. 8) calculate all or part of textual information 392a, 392b based on a stored exercise profile and/or based on the program definition of the stored program. For example, it is contemplated that the exercise profile defines only some of textual information 392a, 392b and that treadmill 12 calculates additional information provided in textual information 392a, 392b. For instance, limited program information such as the program duration and speed and incline information may be stored in the exercise profile. Based on this limited information, other information such as the distance and climb may be calculated. Similarly, the process may be reversed such that average speed or incline can be calculated based on a specified distance, duration, and climb. In yet another embodiment, treadmill 12 reads program definitions 256a, 256b (FIG. 9) and calculates all or part of textual information 392a, 392b.

Browser 390 may also display visual information 394a, 394b representative of an exercise program. In this embodiment, for example, visual information 394a, 394b is graphical or chart information representative of the exercise program. In particular, visual information 394a, 394b, may chart various operating parameters of treadmill 12 as they will be controlled during the workout. In the illustrated embodiment, for example, the anticipated speed of treadmill 12 is illustrated by bar data while the incline of treadmill 12 is illustrated by overlapping line data.

As noted previously, visual information 394a, 394b may be supplied in an exercise profile stored on memory card 13. In an alternative embodiment, visual information 394a, 394b and/or textual information 392a, 392b may not be specified, whether in whole or in part, by an exercise profile. For example, program translator 211 (FIG. 8) may obtain the program definition for a workout from memory card 13. Based on the segments defined in the program definition, program translator 211 and/or processors 192, 214 (FIGS. 7 and 8) may create visual information 394a, 394b. Additionally, the program definition may be read and thereafter used to obtain textual information 392a, 392b such as, for example, program duration, distance, climb, speed, incline, resistance, or other information.

Figure 15:
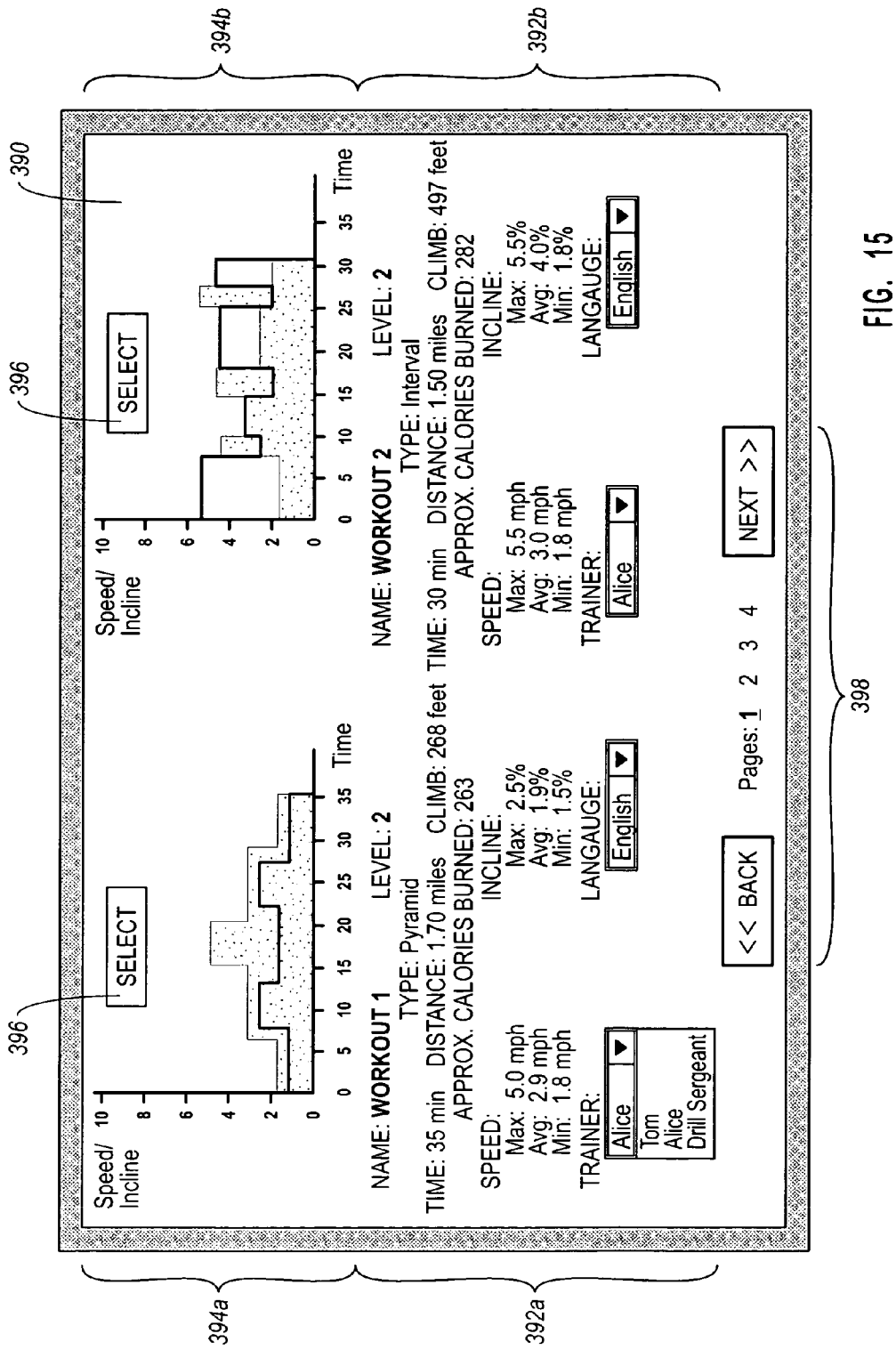
FIG. 15 is an illustration of the visual output device of FIG. 6 displaying exercise profiles representative of exercise programs stored on the portable data storage device of FIG. 1.
Figure 16:
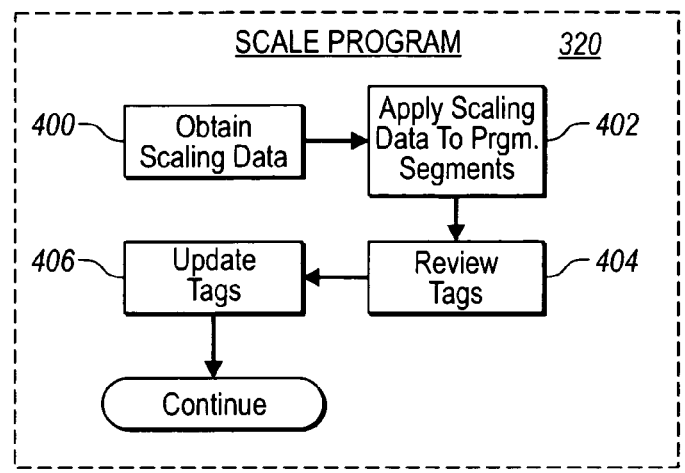
FIG. 16 is a flow diagram illustrative of the process of scaling an exercise program selected in the process of FIG. 14.

As is further illustrated in FIG. 15, browser 390 displays, in one embodiment, motivational content information for an exercise program. For instance, in the illustrated embodiment, textual information 392a, 392b includes information about the voice and language in which motivational content is provided. Such information may be defined by the exercise program on memory card 13 or, in another embodiment, based on a user's preference. For instance, content library 258 (FIG. 9) may include a content category containing motivational content files specific to particular workout. The content category may include only a single set of motivational content files, with one voice and language. Accordingly, textual information 392a, 392b may be pre-set to indicate what trainer and/or language corresponds to the motivational content.

In another embodiment, personalized user information 264a, 264b (FIG. 9) stores preferences and treadmill 12 displays motivational content information according to these preferences. For instance, the user may set a preference for a desired voice and/or language for motivational content. Accordingly, where multiple voices and/or languages are available for motivational content, a voice and language corresponding to those preferences may be presented. Further, in some embodiments, motivational content information may be selected and changed by the user with the browser. For example, the user may select a desired voice or language from a combo box that contains various options. According to this selection, a corresponding content category 260a-c (FIG. 9) in content library 258 (FIG. 9) may be identified for use with content tags received during delivery of the exercise program. It may be appreciated, however, that inasmuch as content categories 260a-c (FIG. 9) are optional or may correspond merely to a workout on memory card 13, user selection of motivational content is only one embodiment, and not a limiting feature of the present invention.

In another aspect of the present invention, a user may review saved exercise programs using navigational tools 398 which are optionally displayed within browser 390. For instance, a pre-set number of exercise programs (e.g. 2, 4, 6, etc.) may be displayed on a single page with options to navigate between the various pages. Optionally, navigational tools 398 include options to change between pages, change views of workouts (e.g. to display more or less programs at one time), to search for exercise programs, and other similar options.

In yet another embodiment, it will be appreciated that all exercise programs are displayed on a page, or programs are presented to the user individually (i.e. one at a time). Accordingly, more or less extensive information about an exercise program can be presented to the user than previously described. For example, in one embodiment, only limited information such as a program name is displayed in a list of all available exercise programs. A user may then identify and select a single program, or may request additional information on the program. If additional information is requested, treadmill 12 may then retrieve profile information or program definitions from memory card 13, calculate program profile information, and/or present the requested information to the user.

Once the exercise program information is displayed, as represented by block 372, a displayed program may be selected by any suitable means, as represented by block 374. For instance, as described previously, processor 214 (FIG. 7) may connect to various input devices 216 (FIG. 9) such as, for example, mouse 100, keyboard 108, camera 92, microphone 90, game controllers, a touch-screen on visual output device 94, and the like. Using such input devices, a user may select a desired exercise program. For example, in the embodiment illustrated in FIG. 15, selection buttons 396 may be selected for a corresponding program, although other suitable means, including double-clicking, voice recognition systems, and the like may be used to identify the desired workout. Once a workout is selected, process 300 continues to decision block 318 (FIG. 10), as will be described in more detail hereinafter.

Figure 14:
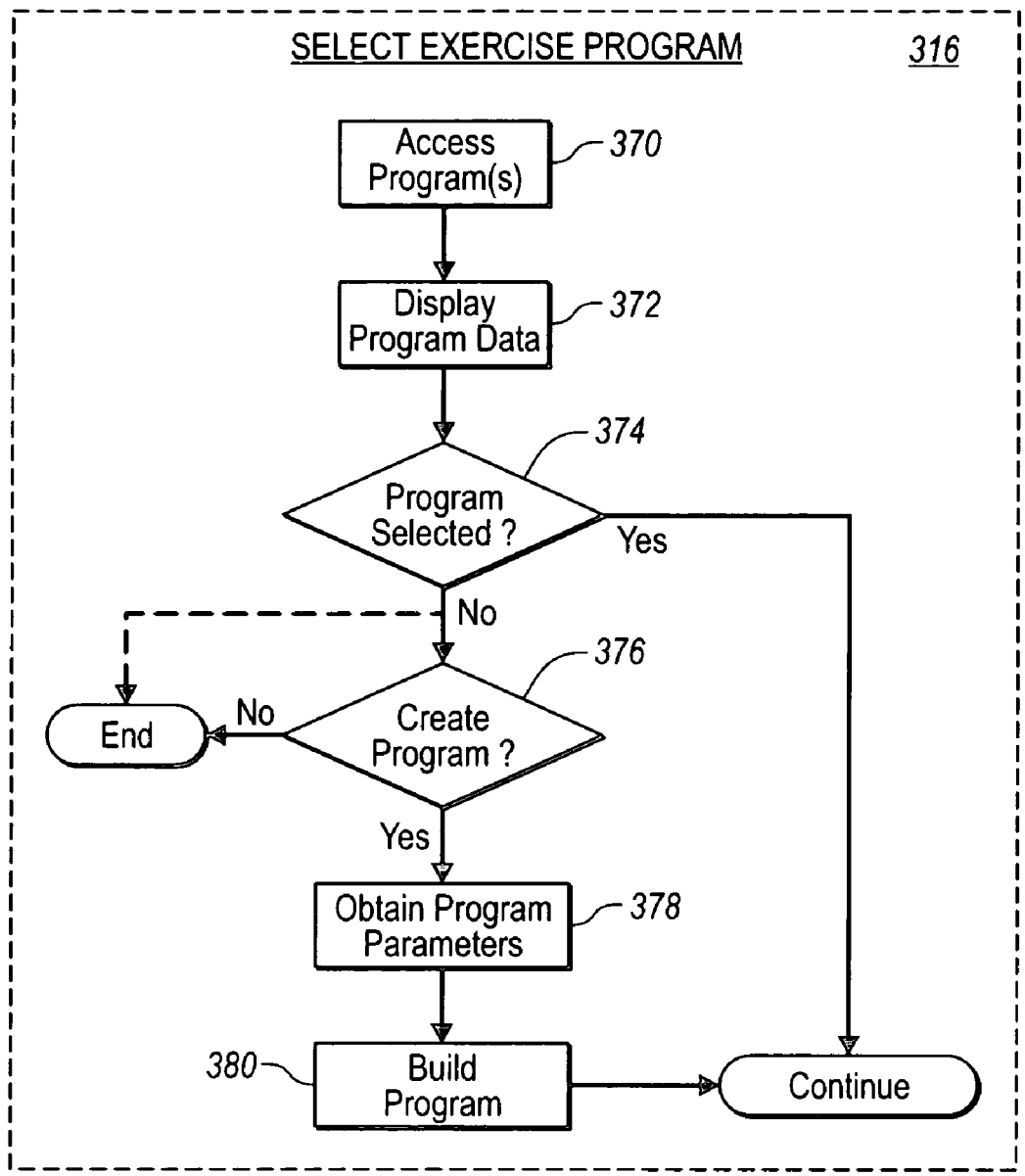
FIG. 14 is a flow diagram illustrative of the process of selecting an exercise program stored on the portable data storage device of FIG. 1.

In the event that a user does not find a desired exercise program, such as when decision block 374 is in the negative, a user may optionally end process 300, as represented by the dotted line in FIG. 14. As represented by decision box 376, however, an optional step in selecting an exercise program may allow a user to create an exercise program. Creation of an exercise program may be done by a workout generation module such as workout generator 270 (FIG. 9) on data storage device 250 (FIG. 9). It may be appreciated, however, that workout generator 270 (FIG. 9) may similarly be contained within more than one module on memory card 13, or within one or more modules in control panel 22 or otherwise within treadmill 12, computer 14, or communication system 18.

Upon deciding to create an exercise program, such as when decision block 376 is in the affirmative, workout generator 270 (FIG. 9) may obtain program parameters for the desired exercise program, as represented by block 378. Program parameters may include, for example, one or more of the information previously described as within an exercise profile, including program duration, distance, intensity level, climb, speed information, incline information, and the like. In one exemplary embodiment, the program parameters are obtained from personalized user information 264a, 264b (FIG. 9). For instance, personalized user information may include a user's workout preferences. Alternatively, when a workout is completed on treadmill 12, treadmill 12 may update user information 264a, 264b (FIG. 9) with statistical information about a user's tendencies or preferences. In still another alternative, workout generator 270 (FIG. 9) reviews workout history 266 (FIG. 9) for a user to obtain such statistical information.

In yet another embodiment, a user may expressly specify the workout parameters. For example visual output device 94 (FIG. 7) may prompt a user to enter one or more parameters to be included in the created exercise program. Workout generator may then, according to one or more algorithms, create one or more program definitions by building segments and control signals or control signal instructions to operate treadmill 12 in a manner such that the operating parameters correspond to the parameters input by the user, as represented by block 380. For instance, a user may specify a program duration, distance, maximum or minimum speed/incline, average speed/incline, and the like.

In addition, user input or the user's personalized information 264a, 264b (FIG. 9) may also be used to insert tags to motivational content within a created program. As noted previously, in reference to FIG. 9, motivational content library 258 may include one or more content categories 260a-c, each having one or more motivational content files. According to the user preferences or input, workout generator 270 may select an appropriate category for content tags inserted into the created exercise program. Optionally, the user instead specifies the type of motivational content at the time other parameters are specified.

One manner of associating content tags with a generated workout is described previously. In particular, each motivational content file may also have one or more associated attributes. For instance, in a simplified manner, a motivational content file may have an "Up" or "Fast" attribute indicating that the content file is appropriate for use when a treadmill incline or speed, respectively, is to increase. Similarly, a "Down" or "Slow" attribute indicates the file is appropriate for respective decreases in incline and speed. Attributes of "Begin" and "End" may likewise identify files appropriate for initiating or ending an exercise program, while a "Sustain" attribute may indicate a corresponding file is appropriate in the middle of long segments or rigorous stretches in an exercise program.

It will be appreciated that additional attributes are also available for association with content files, and that attributes may be more or less complex. For example, attributes may be indicative of specific operating parameters of treadmill 12. For instance, an "s4" attribute might indicate that a content file is appropriate when treadmill 12 receives a control signal for, or has an operating parameter of, 4 mph. Similarly, an "i4" attribute provides a similar indication for a four degree incline. In another alternative, an attribute such as "transition s2-5" might be used to indicate an associated file is appropriate at a transition between segments in which speed increases from 2 to 5 mph. As may be appreciated by those of ordinary skill in the art in light of the teachings herein, a variety of attributes of varying complexities may be identified and associated with motivational content files. For instance, attributes might specify whether a file is appropriate at a particular time within a program, at a particular distance, etc. Content categories might also, for example, be eliminated by providing information within the motivational content files themselves, such as, for example, by using a "name," "voice," "language," or other attribute that may identify, for example, the program name or the voice and language in which the motivational content is presented. Further still, it will be appreciated that a single attribute may be associated with multiple files and that each file may have various associated attributes.

As workout generator 270 builds an exercise program, multiple segments may be created. In one embodiment, for example, an exercise program is created to be run on treadmill 12. Workout generator 270 may create a workout by defining a specified speed and/or incline for each segment or for control signals defining operating parameters indicative of speed or incline to be generated at specific times. When such a program definition is created and segments defined, or thereafter, workout generator 270 may, accordingly, associate the desired operating parameters of treadmill 12 with the appropriate control signals as well as with content file attributes. In this manner, as or after segments are built, workout generator 270 can query content library 258 to identify one or more appropriate content files and insert content tags which reference or call any or all appropriate files.

Thereafter, the created exercise program may be stored on memory card 13, treadmill 12, and/or computer 14, and optionally displayed to the user in any suitable manner, such as described above. Thereafter, the user may select the program for use with treadmill 12. Alternatively, the user may reject the exercise program, and create one or more additional programs by using the same or different parameters.

Returning again to FIG. 10, it will be seen that after a program has been selected, process 300 includes an optional step of determining whether the selected program should be scaled, as represented by decision block 318. A description of an exemplary method for scaling an exercise program is described in U.S. Pat. No. 6,458,060 which is herein incorporated by reference in its entirety. In particular, U.S. Pat. No. 6,458,060 describes a method in which a user may activate scaling control button 86 and vary the intensity of an exercise program. For example, in one embodiment, a user may select a value representative of a proportional change to be made to each segment of an exercise program. In this manner, and as an example, if a scaling factor of two-thirds is selected, each control signal or all the control signal information within a program definition may be decreased by one third such that the intensity of the exercise program is two-thirds that of the originally selected program. For example, a segment with a speed of 6 mph and incline of 15 degrees will be scaled such that the control signals modify treadmill 12 to have reduced and scaled operating parameters of 4 mph and 10 degrees, respectively. Optionally, the a scaling factor may change the timing of a segment or exercise program, such that a 3 minute segment may then be changed to only 2 minutes and a 30 minute program may be reduced to 20 minutes.

It may be appreciated that a user may scale all operating parameters of treadmill 12 in the selected workout, may scale only a single operating parameter, or may scale any combination of one or more operating parameters of treadmill 12. Accordingly, a user may select a scaling value to be applied to one or more operating parameters, or may select a maximum, minimum, or average value to be applied to any or all operating parameters and exercise program parameters. Similarly, a user may select a program duration and/or distance and scale the program accordingly. In this manner, a user may vary a selected exercise program to suit the user's particular abilities so as to obtain the beneficial effects of exercising. It may also be appreciated that program may be scaled automatically, or without user input. For instance, system 10 may include a heart rate monitor (not shown) attached to a user for determining that a user maintains a target heart rate. In such a case, an exercise program may be scaled to increase or decrease one or more operating parameters of treadmill 12 to assist the user in maintaining a desired heart rate.

It may also be appreciated in light of the teachings herein, that in the event an exercise program is scaled or otherwise modified, it may be desirable to modify the motivational content to more appropriately reflect the modified exercise program. For instance, a stored exercise program may include a tag to motivational content which is set specifically for the operating parameters contemplated when the segment was created. For example, a content file with a "transition s4-6" attribute may be tagged at the beginning of a segment which is designed to change the speed from 4 to 6 mph. In the event the segment is scaled and the speed changed such that the speed of the scaled program changes from, for example, 2 to 4 mph, such a tag may no longer be appropriate. In contrast a content file having a "Fast" attribute may still be appropriate inasmuch as the speed of treadmill 12 still increases in the scaled program.

Accordingly, when decision block 318 is the affirmative, the process 300 can include scaling the exercise program, as represented by block 320. Further, and as illustrated in more detail in FIG. 16, scaling the exercise program can include obtaining scaling information, as represented by block 400 and applying such scaling to the control signals or program definitions of an exercise program, as represented by block 402. In addition, and as represented by blocks 404 and 406, tags to motivational content files may thereafter be reviewed and updated as necessary. In one embodiment, the review and updating of content tags is performed by workout scaling module 272 (FIG. 9) stored on memory card 13. It will be appreciated, however, that processors 192, 214 (FIGS. 7 and 8), program translator 211 (FIG. 9), and other components of treadmill 12 or computer 14 may perform the operations of scaling module 272 (FIG. 9), or that scaling module 272 (FIG. 9) may be included within control panel 22 or otherwise within treadmill 12 or computer 14.

In one embodiment, workout scaling module 272 (FIG. 9) caches a scaled version of the selected exercise program, such that the scaled version includes scaled segments within the program definition. Thereafter, scaling module 272 (FIG. 9) reads the content tags within the cached exercise program. The files associated with each content tag may be found within content library 258 (FIG. 9) and the file attributes read. If the content file attributes are consistent with the operating parameters of treadmill 12 at the time of the tag or during the segment in which the tag is referenced, the tag may be left unmodified. In contrast, if the file attributes are inconsistent with the scaled operating parameters of treadmill 12, scaling module 272 (FIG. 9) may find an appropriate tag and replace the content tag in the cached version with the updated tag. As will be appreciated, in one embodiment, finding an appropriate tag includes querying content library 258 (FIG. 9) for content files having appropriate attributes.

As may also be appreciated, caching an exercise program is only one embodiment of the present invention and is not limiting of the present invention. In particular, another embodiment is also contemplated in which scaling module 272 (FIG. 9) dynamically controls treadmill 12 according to scaling parameters. For instance, during delivery of an exercise program, scaling module 272 (FIG. 9) may review tags by monitoring and intercepting function calls for content files. As a function call is placed, scaling module 272 (FIG. 9) reviews the attributes associated with the associated content file and determines if the attributes match the current operating parameters of treadmill 12 or an associated exercise program segment. If the file attributes do not match the operating parameters, scaling module 272 (FIG. 9) may then find a more appropriate content file and deliver the second content file in response to the function call. Accordingly, it can be seen that scaling module 272 (FIG. 9) may allow for dynamic delivery of content files in response to current operating parameters of treadmill 12. Thus, scaling module 272 (FIG. 9) may begin scaling an exercise program at any point during the exercise program. In addition, in the event a user manually overrides operating parameters of treadmill 12, scaling module may also dynamically monitor the operating parameters and deliver appropriate motivational content to the user.

Again returning to FIG. 10, it will be seen that process 300, in which treadmill 12 interacts with memory card 13, further includes delivering an exercise program, as represented by block 322. As described previously, a user may select an exercise program from among one or more such programs saved on memory card 13. Delivering the workout to the user may require that signals associated with the program be transmitted from memory card 13 to treadmill 12. In one embodiment of the present invention, this may be accomplished by processor 214 (FIG. 7) in a control panel 22 of treadmill 12 and which, through communication interface 210 (FIG. 7), adopts appropriate protocols such that treadmill 12 can read data stored on card 13.

Figure 17:
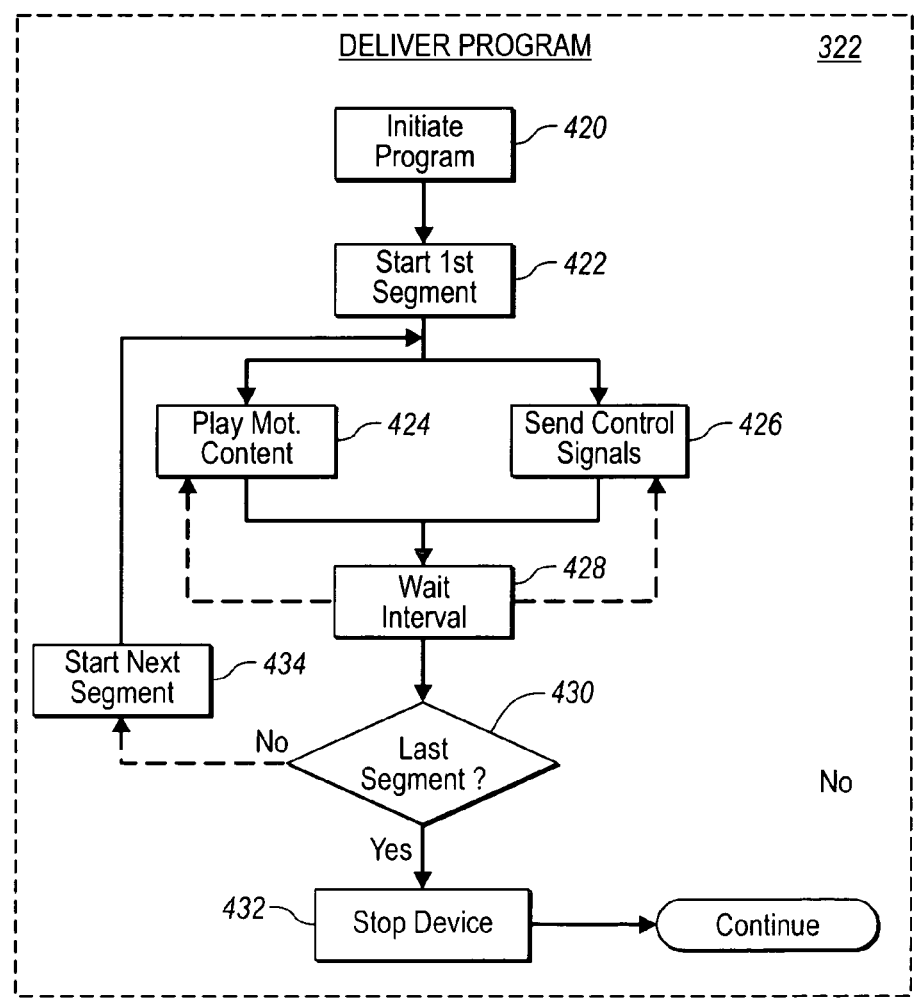
FIG. 17 is a flow diagram illustrative of the process of delivering an exercise program to a user of the exercise system of FIG. 1.

In one embodiment, and as shown in more detail in FIG. 17, control panel 22 delivers a program to a user by initiating the program, as represented by block 420. The exercise program may be initiated in any of a variety of manners. For example, the stored exercise program may include program definitions that are stand alone executables. Accordingly, control panel 22 may initiate execution of the executable, and the stored exercise program may execute the program definition and send appropriate control signals to begin the exercise program, as represented by block 420.

In another embodiment, the program definition in the selected exercise program is in the form of computer-executable instructions. Processors 192, 214 (FIGS. 7 and 8) may read memory card 13 to obtain the instructions which treadmill 12 then executes. Accordingly, initiating the program includes treadmill 12 receiving program instructions such that they can then be executed by a module within treadmill 12 (e.g. communication interface 210 (FIG. 7), processor 214 (FIG. 7), or program translator 211 (FIG. 7)).

Regardless of whether the exercise program is a stand-alone executable which generates control signals and transmits control signals and motivational content to treadmill 12, or whether the exercise program is computer-executable instructions which are then executed by a module on treadmill 12, once the program is initiated, a first segment may begin, as represented by block 422. Further, any content tags may be executed, or control signals generated, such that they are transmitted to treadmill 12, as represented by blocks 424 and 426, respectively. In the illustrated embodiment, playing motivational content and sending control signals are illustrated in parallel to emphasize that motivational content may be synchronized with the control signals, and thus the operating parameters of treadmill 12. Nevertheless, it will be appreciated, that playing motivational content and sending control signals may also be performed serially, such that motivational content may be tagged and played before or after control signals are generated and sent to treadmill 12.

As discussed above, system 10 may play motivational content, at appropriate times in the delivery of the exercise program. In one embodiment, the motivational content is stored independently of the exercise program or exercise program definition, such as in motivational content library 258 (FIG. 9). The exercise program may, therefore contain tags operating as function calls. In this manner, as the exercise program is being executed, a function call is sent to content library 258 (FIG. 9) with a reference for an appropriate content file. If the referenced file is found within library 258 (FIG. 9), the file is delivered to treadmill 12 through communication interface 210 (FIG. 7). Communication interface 210 (FIG. 7) thereafter delivers the information to processor 214 (FIG. 7) which distributes the information such that it can be played. For example, processor 214 (FIG. 7) distributes audio or visual content to audio/video controller 212 (FIG. 7) which then may configure the content for display on visual output device 94 (FIG. 7) and/or delivery through speaker 96 (FIG. 7) and, thus, be perceived by the user during his or her exercise program.

In another embodiment of the present invention, a user may selectively limit or eliminate motivational content from a selected exercise program. For instance, while using an exercise program, a user may be watching or listening to educational or entertainment programming on an output device of treadmill 12, on computer 14, or on any other device. If the motivational content is audio, for example, and a user wants to avoid disruption of the educational or entertainment programming, a user may mute the audio motivational content. Accordingly, the user may, in one embodiment, turn off the volume of speaker 96 (FIG. 7). In another embodiment, the user may select a mute button (not shown) on control panel 22. Upon selecting the mute button, treadmill 12 may maintain the volume of speaker 96 (FIG. 7), but ignore any content tags or motivational content.

Additionally, generation and transmission of control signals may be calculated to control treadmill controller 56 or other mechanisms having or controlling a movable element. As noted previously, control signals may be created by an exercise program stored on memory card 13, and transmitted to treadmill 12. For example, computer-executable instructions within a stand-alone executable may be used such that control signals are generated by the exercise program and control signals sent from memory card 13 to treadmill 12 via communication interface 210 (FIG. 7). The control signals may then be routed to processors 214, 220 or signal decoder 224 (FIG. 7). In this manner, treadmill processor 220 may then receive and interpret the received control signals indicative of desired operating parameters of treadmill 13 and control speed motor 226 (FIG. 7) and/or incline motor 228 (FIG. 7) to obtain the desired operating parameters.

Similarly, where a selected exercise program is computer-executable instructions executed by treadmill 12, control signals may be generated to control movable elements of treadmill 12. For instance, the computer-executable instructions may include a program definition which defines various operating parameters of treadmill 12, including segment timing or interval timing to determine when changes in operating parameters are made. These instructions are transmitted from memory card 13 to processors 192, 214 and/or program translator 211 (FIGS. 7 and 8). Processors 192, 214 and/or program translator 211 are configured to interpret the instructions and generate control signals at the appropriate times. Upon generation, the control signals are similarly transmitted to treadmill processor 229 (FIG. 7) and/or control signal decoder which thereafter control speed motor 226 (FIG. 7) and/or incline motor 228 (FIG. 7) to obtain the desired operating parameter specified in the computer-executable instruction. Therefore, memory card 13 may be a structure capable of performing the functions of: (1) communicating means, communicating with the interface means; (2) means for controlling operating parameters of an exercise mechanism; and (3) means for driving the movable element operating in response to decoded control signals.

As noted previously, motivational content may or may not be synchronized with control signals. For instance, motivational content may be synchronized with an operating parameter of the treadmill, but not sent at or near the same time as a control signal. As illustrated in FIG. 17, after a control signal is sent, treadmill 12 may not receive changed signals until the segment interval (i.e. time during which one or more operating parameters are to remain constant) has ended. As the exercise program on memory card 13 is being run, the exercise program may initiate a timing sequence within the exercise program on treadmill 12, as represented by block 428. As the timing sequence ends, a determination is made as to whether there is an additional segment, as illustrated in decision block 430. If no segments remain because the exercise program has ended, and decision block 430 is in the affirmative, treadmill 12 is stopped by sending an appropriate control signal, as represented by block 432. In contrast, if another segment remains, and decision block 430 is in the negative, the new segment is initiated, as represented by block 434, and any corresponding control signals and motivational content are received by treadmill 12.

As illustrated by the dashed line between blocks 428 and 424, however, motivational content may optionally be played during a segment interval, and before a new segment is initiated. In other words, the delivery of motivational content need not correspond with the transmission of control signals. For instance, a motivational content tag within an exercise program may call a content file during the middle of a segment interval. The motivational content may be synchronized, for example, with the then current operating parameters of the treadmill, or other aspects of the exercise program. Thus, motivational content may be synchronized with operating parameters without necessarily being synchronized with control signals.

Optionally, and as illustrated in FIG. 17, control signals may be retransmitted during a segment interval, as represented by the dotted line extending from block 428 to block 424. In one embodiment, for example, retransmission of control signals occurs at regular intervals and is used as an error correction device. In particular, by retransmitting signals, in the event a control signal is corrupted or incorrectly interpreted such that an operating parameter is not changed or is incorrectly changed, the retransmission of the control signal can correct the operating parameter.

According to one aspect of the present invention, a user may also maintain an exercise log that keeps a history of the workouts and exercise programs completed by the user. Accordingly, the present invention optionally includes, as represented by decision block 310 in FIG. 10, an option of updating user information. For instance, upon completion of a workout, browser 390 (FIG. 15) and/or visual output device 94 and speaker 96 (FIG. 7) may request an indication from the user whether information stored on treadmill 12 or memory card 13 or treadmill 12 should be updated to include information about the completed workout. In one embodiment, for example, memory card 13 includes workout history 266 (FIG. 9) which records information about one or more completed workouts. For instance, workout history 266 may include any combination of the name of a completed workout, completion date and time, duration, distance, elevation climbed, calories burned, and the like. Optionally, the workout history may also be stored on treadmill 12 or computer 14 where, for example, memory card 13 is write-access restricted.

After completion of an exercise program, if the user indicates his or her desire to add the new information, treadmill 12 may then access the new information to be added. The new information may be obtained from, for example, an exercise profile stored on memory card 13. Alternatively, measurable data of the exercise program may be stored in treadmill 12 (e.g. memory 222). Processor 220 or 214 may thus access the information and, in one embodiment, save the information to memory card 13 through communication interface 210.

By storing workout history 266 on memory card 13, treadmill 12, or a connected computer 14, a user is enabled to keep an accurate history of workouts without the need to manually enter information into a separate log. Where workout history 266 is on memory card 13, it may also easily be transported between exercise devices. This can be beneficial for a user who does not consistently use the same exercise device or who does not have access to a computer. For instance, a user may exercise on a device at a commercial gym and may avoid entering personal information on each device, or can review his or her workout history to make a decision on which exercise program to choose. Additionally, the user may insert memory card 13 and the user information may automatically update the treadmill. Alternatively, the user may review his or her workout history 266 on an output device of the exercise device. Thereafter, a stored workout can be chosen, executed, and the updated information stored to workout history 266. As still another alternative, the user may later upload stored workout history 266 to a personal computer.

Alternatively, or in addition, upon completion of an exercise program, treadmill 12 may automatically determine that personal information on memory card 13 should be updated. For instance, personalized user information 264*a*, 264*b* may keep statistical information on a user's tendencies or workout history. Accordingly, using personalized user information 264*a*, 264*b*, treadmill 12 can review distances, durations, difficulty levels, etc. of available exercise programs and assign a probability that the user will select any given exercise program. This may be useful, for example, when a user is selecting an exercise program as saved programs may be presented to the user in an order of the probability that a user will select the specific workout.

It should also be appreciated that a user may choose to update the information. For example, upon completion of an exercise program, a user may desire to enter the completed workout information manually and/or input one or more other, unlogged workouts. For example, a user may select an option to manually enter his or her workout information. Alternatively, after the recently completed program is entered, a user may be asked if any other workouts should be added, at which time the user can specify the exercise information for the unlogged workouts. In a similar fashion, a user may view his or her personal information 264*a*, 264*b* and input updates at control panel 22. Accordingly, updates to a user's name, age, weight, fitness level, workout preferences, and the like can be input and, thereafter, the updated information can be saved to, and potentially replace, his or her personal information stored on the memory card, treadmill, and/or computer. As previously discussed, information stored on a memory card may then be accessed on another exercise device. In some cases the information may be accessible only by an authorized exercise device (e.g. data on a DataFlash card), or it may be transferable or accessible by a general purpose computer (e.g. data on an SD card).

Once the user data or information has been updated, where applicable, the process 300 continues through the methods associated with blocks 310, 312, and 314, until the program ends. Once the program ends the exercise device can be stopped.

As will be appreciated, particularly, in light of the discussion herein, the present invention includes a variety of novel aspects and features. For instance, one embodiment is contemplated relating to a computer program product for use with an exercise device configured to enable a user to perform an exercise program, in which the computer program product comprises: one or more computer-readable media connected to the exercise device, the one or more computer-readable media having computer-executable instructions for: (i) retrieving first fitness data from a portable memory card connected to the exercise device; (ii)-delivering the first fitness data to a user of an exercise device; and (iii) saving second fitness data on the portable memory card, the second fitness data being personalized to the user.

Further, the first fitness data may be one or more exercise programs and, in other embodiments, may include one or more exercise program parameters corresponding to the one or more exercise programs, and wherein the computer-readable media have computer-executable instructions for displaying the one or more exercise program parameters to the user for selection of a corresponding exercise program for delivery to the user. Further still, in such a computer program product, the second fitness data can include one or more of the user's name, age, weight, sex, fitness level, exercise preferences, exercise device type, or exercise program history.

Optionally, computer-executable instructions are included for: (i) receiving input from the user indicative of the second fitness data; (ii) obtaining the second fitness data upon delivering the first fitness data to the user; (iii) determining a format of the portable memory card; and/or (iv) communicating with the portable memory card, wherein the portable memory card is any of a plurality of formats. As noted previously, the plurality of formats can include at least Secure Digital and DataFlash.

In another embodiment, in an exercise device having access to pre-programmed exercise programs, a method is disclosed for writing user information to a portable memory card, the method comprising: (i) in a communication port configured to access a portable memory card, receiving a portable memory card of a first format or a second format; (ii) determining that the portable memory card is of the first format; (iii) selectively accessing protocols on the exercise device, the protocols being associated with the first format, wherein the protocols include access protocols to write information to the portable memory card; and (iv) writing to the portable memory card using the selectively accessed protocols. The method may further include wherein writing to the portable memory card includes writing user data to the portable memory card using the selectively accessed protocols.

As described previously, such a method may include receiving the user data at a user interface of the exercise device. Further determining that the portable memory card is a first format may comprise determining that the portable memory card is a DataFlash card. Optionally, the method further comprising reading user data stored on the portable memory card, where such user data may be an exercise program or one or more personal indicators.

In another embodiment, for use with an exercise device having a moveable element for movement in performance of exercise by a user, the moveable element being controlled by one or more operating parameters, a method for delivering an exercise program to a user of an exercise device is disclosed, the method comprising: (i) accessing an exercise program, the exercise program comprising: (a) a plurality of program segments, wherein each of the plurality of program segments defining one or more operating parameters, the one or more operating parameters being constant during each of the plurality of program segments; and (b) one or more motivational content tags corresponding to one or more motivational content files, wherein the one or more motivational content files are stored independent of the plurality of program segments, and wherein the one or more motivational content tags are delivered to a user at predetermined locations within the exercise program; (ii) controlling the moveable element of the exercise device according to the one or more operating parameters defined by the plurality of program segments; and (iii) providing, at the predetermined locations within the exercise program, motivational content corresponding to the motivational content files and the motivational content tags.

As indicated previously, the motivational content files may be stored in a manner that substantially reduces the size of the exercise program and, in some embodiments, are stored in a database. Optionally, the motivational content files are stored separate from the exercise program.

A step of providing motivational content may further include providing one or more of the one or more motivational content files a plurality of times during the exercise program. For example, the one or more motivational content tags can include at least two tags corresponding to a single motivational content file. Moreover, the exercise program may be stored on a computer-readable medium communicatively connected to the exercise device, including a portable memory card received by an input device of the exercise device. Further still, the one or more motivational content files are stored on the portable memory card, and/or are audio or video.

In still other embodiments, the motivational content files are personalized for the user of the exercise device, or the method includes accessing motivational content files corresponding to a user preference. Moreover, the method for delivering an exercise program may include dynamically modifying the exercise program.

As noted previously, a method for building an exercise program to be delivered to a user of an exercise device, is provided herein, the method comprising: (i) defining one or more program segments, each of the one or more segments defining: (a) a segment interval; and (b) one or more operating parameters for controlling a moveable element of an exercise device, the one or more operating parameters remaining constant during the segment interval, and (ii) inserting one or more motivational content tags, the one or more motivational content tags corresponding to one or more motivational content files stored independent of the one or more program segments.

In such a method a plurality of one or more motivational content tags refers to a single motivational content file and/or one or more motivational content files are optionally synchronized with the one or more operating parameters of the exercise device. Further, such content files can include music or video.

In some embodiments, the method for building an exercise program further includes packaging the exercise program; and providing the packaged exercise program to a user of the exercise device. Packaging the exercise program can also include saving the exercise program on a computer-readable medium such as, for example, a portable memory card and/or saving the one or more motivational content files on a computer-readable medium.

The previously disclosed method, in which a packaged exercise program is transferred to a user, may also include transferring the packaged exercise program to a user by: the user downloading the packaged exercise program over a network; or storing the packaged exercise program on a physical computer-readable medium and delivering the physical computer-readable medium to the user. Further, the method may include obtaining program parameters representative of the exercise program. Additionally, steps of defining one or more program segments and inserting one or more motivational content tags are, in some implementations, performed by user executable instructions in response to obtaining the program parameters representative of the desired exercise program. Moreover, program parameters representative of the exercise program can include at least one of: distance; duration; maximum speed; maximum incline; maximum resistance; minimum speed; minimum incline; minimum resistance; average speed; average incline; average resistance; climb; or exercise program type.

In yet another embodiment, a computer program product is contemplated for use with an exercise device having a moveable element being controllable by one or more operating parameters, the computer program product comprising a computer-readable medium comprising computer-executable instructions having: (i) a plurality of program segments, each of the plurality of program segments defining one or more operating parameters for controlling a moveable element of an exercise device; and (ii) one or more motivational content tags corresponding to one or more motivational content files, wherein the one or more motivational content files are accessible by the exercise device and stored independent of the plurality of program segments.

As may be appreciated, in light of the disclosure herein, the computer-readable medium further comprises a database of the one or more motivational content files. Optionally, the computer-readable medium is a portable memory card which may be in, for example, one of a Secure Digital or DataFlash format.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An exercise device configured to enable a user to perform an exercise program, the exercise device comprising:
a movable element for movement in performance of exercise by a user; and
a console operatively connected to said movable element, said console comprising a data port configured to receive a portable memory card having any of a plurality of formats, wherein said console is configured to communicate with said portable memory card having any of said plurality of formats so as to control one or more operating parameters that control said movable element, such that a first memory card having a first format of said plurality of formats can be selectively received in said data port to communicate with said console to control said one or more operating parameters, and such that, when said first memory card is not received in said data port, a second memory card having a second format of said plurality of formats can be selectively received in said data port to communicate with said console to control said one or more operating parameters.

2. An exercise device as recited in claim 1, wherein said portable memory card having an of a plurality of formats is selected from the grouped consisting of Secure Digital and DataFlash cards.

3. An exercise device as recited in claim 1, further comprising means for accessing user data stored on a portable memory card received by said data port, wherein said means for accessing user data comprises access protocols for each of said plurality of formats.

4. An exercise device as recited in claim 3, wherein said user data includes at least one of an exercise program and personal indicators.

5. An exercise device as recited in claim 3, wherein said user data includes at least an exercise program, said exercise program having data indicative of motivational content and instructions for at least one control signal for changing one or more operating parameters controlling said movable element.

6. An exercise device as recited in claim 3, wherein said means for accessing user data selectively applies said access protocols upon determining the type of portable memory card received by said data port.

7. An exercise device as recited in claim 6, wherein said access protocols allow said console to write information to said portable memory card.

8. A method as recited in claim 6, wherein said one or more motivational content files are stored on said portable memory card having any of a plurality of formats.

9. An exercise system configured to enable a user to perform an exercise program, the exercise system comprising:
an exercise mechanism comprising a moveable element for movement in performance of exercise by a user, the exercise mechanism having one or more operating parameters that control the moveable element; and
a data port operatively connected to said exercise mechanism, said data port being adapted to receive and communicate with a portable memory card having any of a plurality of formats, and wherein said data port facilitates control of said exercise mechanism by an exercise program stored on said portable memory card by facilitating communication between said portable memory card and said exercise mechanism, wherein said exercise program comprises:
a plurality of program segments, each of said plurality of program segments defining one or more operating parameters for controlling the moveable element during said exercise program; and
one or more motivational content tags corresponding to one or more motivational content files, said one or more motivational content files being stored independent of said plurality of program segments, and one or more motivational content tags being provided in predetermined intervals within said exercise program.

10. An exercise system as recited in claim 9, further comprising:
a communication module operatively connected to said exercise mechanism and said data port, said communication module being capable of accessing said exercise program stored on said portable memory card.

11. A system as recited in claim 9, wherein said plurality of formats includes at least Secure Digital and DataFlash.

12. A system as recited in claim 10, further comprising:
a processor in communication with said exercise mechanism and said communication module, wherein said processor delivers a control signal to said exercise mechanism, and wherein said control signal is indicative of changing said one or more operating parameters of said exercise mechanism.

13. A system as recited in claim 12, wherein said motivational content files are stored in a database separate from said exercise program.

14. A system as recited in claim 10, wherein said data port is integrated into a control panel of the exercise system.

15. A system as recited in claim 10, wherein said portable memory card has user data stored thereon, and wherein said communication module is configured to access said stored user data.

16. A system as recited in claim 10, wherein said communication module is configured to write user data to said portable memory card.

17. A system as recited in claim 16, wherein said user data is representative of at least one measurable parameter of at least one of: (i) said user; or (ii) said exercise mechanism.

18. A system as recited in claim 13, further comprising:
a user interface connected to said processor, said user interface allowing a user to selectively control one or more of said one or more operating parameters; and
an output device connected to said processor, said output device being adapted to deliver data representative of motivational content.

19. A system as recited in claim 18, wherein said output device is an audio output device and wherein said data indicative of motivational content is audio, and wherein a user of said user interface can selectively determine whether said audio data representative of motivational content is delivered to said user by said audio output device.

20. A system as recited in claim 9, wherein said communication module includes protocols for communicating with said portable memory card in any of said plurality of formats.

21. A system as recited in claim 12, wherein the exercise system further comprises:
a program generation module in communication with said processor, said generation module being adapted to create an exercise program in response to user data.

22. A system as recited in claim 9, wherein said plurality of formats includes a first format of restricted access by a general purpose computing system, and a second format having unrestricted access by said general purpose computing system.

23. An exercise system as recited in claim 9, wherein said motivational content files are stored in a manner that substantially reduces the size of said exercise program.

24. An exercise system as recited in claim 23, wherein providing said motivational content includes providing one or more of said one or more motivational content files a plurality of times during said exercise program.

25. A method as recited in claim 24, wherein said one or more motivational content tags include at least two tags corresponding to a single motivational content file.

26. An exercise device configured to enable a user to perform an exercise program, the exercise device comprising:
a movable element for movement in performance of exercise by a user; and
a control panel operatively connected to said movable element, said control panel comprising a data port configured to receive a memory card following any of a plurality of industry standard protocols, said memory card being adapted to store one or more exercise programs, said one or more exercise programs comprising:
a plurality of program segments, each of said plurality of program segments defining one or more operating parameters for controlling said moveable element of said exercise device; and
one or more motivational content tags corresponding to one or more motivational content files, said one or more motivational content files being accessible by said exercise device and stored independent of said plurality of program segments.

27. An exercise device configured to enable a user to perform an exercise program, the exercise device comprising:
a movable element for movement in performance of exercise by a user; and
a console operatively connected to said movable element, said console comprising a data port configured to receive at least one portable memory card having at least one control signal to control movement of the movable element and one or more motivational content tags corresponding to one or more motivational content files, wherein said one or more motivational content files:
(i) include motivational content presentable to the user in performance of exercise
(ii) are accessible by said exercise device; and
(iii) are stored independent of said at least one control signal.

28. An exercise device as recited in claim 27, wherein said at least one portable memory card includes either a Secure Digital card or a DataFlash card.

29. An exercise device as recited in claim 27, further comprising means for accessing user data stored on a portable memory card received by said data port.

30. An exercise device as recited in claim 29, wherein said user data includes at least one of an exercise program and personal indicators.

31. An exercise device as recited in claim 29, wherein said user data includes said one or more motivational content files and at least an exercise program, said exercise program having data indicative of instructions for at least one control signal for changing one or more operating parameters controlling said movable element.

32. An exercise device as recited in claim 29, wherein said means for accessing user data selectively applies access protocols upon determining the type of portable memory card received by said data port.

33. An exercise device as recited in claim 32, wherein said access protocols allow said console to write information to said portable memory card.

* * * * *